United States Patent
Mayevsky et al.

(10) Patent No.: US 7,313,424 B2
(45) Date of Patent: Dec. 25, 2007

(54) DIAGNOSIS OF BODY METABOLIC EMERGENCY STATE

(75) Inventors: Avraham Mayevsky, Ramat-Gan (IL); Eliahu Pewzner, Modiin Ilit (IL); Assaf Deutsch, Moshav Tzafriya (IL); Tamar Manor, Yehud (IL)

(73) Assignee: CritiSense Ltd., Givat Shmuel (IL)

( * ) Notice: Subject to any disclaimer, the term of this patent is extended or adjusted under 35 U.S.C. 154(b) by 0 days.

(21) Appl. No.: 10/508,232

(22) PCT Filed: Mar. 6, 2003

(86) PCT No.: PCT/IL03/00188

§ 371 (c)(1), (2), (4) Date: May 23, 2005

(87) PCT Pub. No.: WO03/077746

PCT Pub. Date: Sep. 25, 2003

(65) Prior Publication Data

US 2005/0234315 A1 Oct. 20, 2005

(30) Foreign Application Priority Data

Mar. 20, 2002 (IL) ...................................... 148795

(51) Int. Cl.
*A61B 5/00* (2006.01)
(52) U.S. Cl. ........................................ 600/310; 600/322
(58) Field of Classification Search ................ 600/309, 600/310, 322, 317, 323, 324
See application file for complete search history.

(56) References Cited

U.S. PATENT DOCUMENTS

| | | | |
|---|---|---|---|
| 3,750,650 A | 8/1973 | Ruttgers | |
| 4,109,647 A | 8/1978 | Stern et al. | |
| 4,449,535 A | 5/1984 | Renault | |
| 4,569,354 A * | 2/1986 | Shapiro et al. | 600/476 |
| 4,703,758 A | 11/1987 | Omura | |
| 4,711,245 A * | 12/1987 | Higgins et al. | 204/403.1 |
| 4,945,896 A | 8/1990 | Gade et al. | |
| 5,201,318 A | 4/1993 | Rava et al. | |
| 5,318,022 A | 6/1994 | Taboada et al. | |
| 5,348,003 A * | 9/1994 | Caro | 600/310 |
| 5,551,422 A | 9/1996 | Simonsen et al. | |
| 5,579,763 A | 12/1996 | Weil et al. | |
| 5,685,313 A | 11/1997 | Mayevsky | |

(Continued)

FOREIGN PATENT DOCUMENTS

EP 0 392 897 10/1990

(Continued)

OTHER PUBLICATIONS

International Search Report for corresponding PCT application (3 pages).

(Continued)

*Primary Examiner*—Eric F Winakur

(57) ABSTRACT

An apparatus, system and method are provided for diagnosing the degree of body metabolic emergency state. A non-vital organ with respect to the metabolic emergency state is first chosen. One or more tissue viability parameters including at least one of NADH and Flavoprotein (Fp) concentration are monitored in the non-vital organ, whereupon the degree of body metabolic emergency state may be determined based on the monitored tissue viability parameters.

60 Claims, 26 Drawing Sheets

U.S. PATENT DOCUMENTS

| | | | |
|---|---|---|---|
| 5,770,454 | A | 6/1998 | Essenpreis et al. |
| 5,916,171 | A | 6/1999 | Mayevsky |
| 6,071,237 | A | 6/2000 | Weil et al. |
| 6,083,156 | A * | 7/2000 | Lisiecki .................. 600/301 |
| 6,212,424 | B1 * | 4/2001 | Robinson ................ 600/475 |
| 6,216,024 | B1 | 4/2001 | Weil et al. |
| 6,216,032 | B1 | 4/2001 | Griffin et al. |
| 6,258,046 | B1 | 7/2001 | Kimball et al. |
| 6,330,469 | B1 | 12/2001 | Griffin et al. |

FOREIGN PATENT DOCUMENTS

| | | |
|---|---|---|
| EP | 0 442 011 | 8/1991 |
| GB | 2311854 | 10/1997 |
| WO | WO 98/44839 | 10/1998 |
| WO | WO 99/02956 | 1/1999 |
| WO | WO 99/59464 | 11/1999 |
| WO | WO 02/07585 | 1/2002 |
| WO | WO 02/24048 | 3/2002 |
| WO | WO 03/026503 | 4/2003 |

OTHER PUBLICATIONS

Bloeche, C., Strate, T., Emmermann, A., Schneider, C., Mack, D., Wolf, M., Zornig, C., Broelsch, C.E., Izbicki, J.R. (1999). Gastric tonometry accurately predicts mortality in experimental peritonitis in both laparoscopic and conventional surgery. Langenbecks Arch. Surg.,384:76-83.

Boekstegers, P., Weidenhofer, S., Kapsner, T., Werdan, K. (1994). Skeletal muscle partial pressure of oxygen in patients with sepsis. Crit. Care Med., 22:640-650.

Bratslavsky, G., Kogan, B., Levin, R.M. (2001).Urethra is more sensitive to schemia than bladder: evidence from an in vitro rat study. J Urol., 165:2086- 2090.

Cairns, C.B., Moore, F.A., Haenel, J.B., Gallea, B.L., Ortner, J.P., Rose, S.J., Moore, E.E. (1997). Evidence for early supply independent mitochondrial dysfunction in patients developing multiple organ failure after trauma. J. Trauma, 42:532-536.

Chance, B. and Williams, G. R. (1955). Respiratory enzymes in oxidative phosphorylation (III- The steady state). J.Biol.Chem., 217:409-427.

Clavijo, J.A., Sims, C., Menconi, M., Shim, I., Ochoa, C., Puyana, J.C. (2002). Multiparameter monitoring of bladder wall mucosa as a surrogate of gut tissu perfusion in hemorrhagic shock. Paper in preparation.

Dubin, A., Estenssoro, E., Murias, G., Canales, H., Sottile, P., Badie, J., Baran, M., Palizas, F., Laporte, M., Rivas Diaz, M. (2001). Effects of hemorrhage on gastrointestinal oxygenation. Intensive Care Med., 27:1931-1936.

Fiddian-Green, R.G., Baker, S. (1987). Predictive value of the stomach wall pH for complications after cardiac operations: comparison with other monitoring. Crit. Care Med. 15:153-156.

Fink, M.P. (1991). Gastrointestinal mucosal injury in experimental models of shock, trauma, and sepsis. Crit. Care Med., 19:627-641.

Hasibeder, W., Germann, R., Wolf, H.J., Haisjackl, M., Hausdorfer, H.,Riedmann, B., Bonatii, J., Gruber, E., Schwarz, B., Waldenberger, P., Friesenecker, B., Furtner, B. (1996). Effects of short-term endotoxemia and dopamine on mucosal oxygenation in porcine jejunum. Am. J. Physiol., 270:G667-G675.

Hotchkiss, R.S., Karl, I.E. (1992). Reevaluation of the role of cellularhypoxia and bioenergetic failure in sepsis. JAMA, 267:1503-1510.

Ince, C., Sinaasappel, M. (1999). Microcirculatory oxygenation and shunting in sepsis and shock. Crit. Care Med., 27:1369-1377.

Guery, B.P., Mangalaboyi, J., Menager, P., Mordon, S., Vallet, B., Chopin, C. (1999). Redox status of cytochrome a,a3: a noninvasive indicator of dysoxia in regional hypoxic or ischemic hypoxia. Crit. Care Med., 27:576-582.

Jakob, M., Takala, J. (2001). Variability of splanchnic blood flow measurements in patients with sepsis—physiology, pathophysiology or measurement errors? Intensive Care Med. 27:1692-1695.

Knichwitz, G., Rotker, J., Mollhoff, T., Richter, K.D., Brussel, T. (1998) . Continuous intramucosal PCO2 measurement allows the early detection of intestinal malperfusion. Crit. Care Med., 26:1550-1557.

Koivisto, T., Vapalahti, M., Parviainen, I., Takala, J. (2001). Gastric tonometry after subarachnoid hemorrhage. Intensive Care Med., 27:1614-1621.

Lang, J.D., Evans, D.J, deFigueiredo, L.P., Hays, S., Mathru, M., Kramer,GC. (1999). A novel approach to monitor tissue perfusion: bladder mucosal PCO2, PO2, and pHi during ischemia and reperfusion. J. Crit. Care, 14:93-98.

Marik, P.E. (2001). Sublingual capnography: a clinical validation study. Chest, 120:923-927.

Marik, P.E., Varon, J. (1998). The hemodynamic derangements in sepsis:implications for treatment strategies. Chest, 114:854-860.

McKinley, B.A., Butler, B.D. (1999). Comparison of skeletal muscle PO2, PCO2, and Ph with gastric tonometric PCO2 and pH in hemorrhagic shock. Crit. Care Med. 27:1869-1877.

McKinley, B.A., Marvin, R.G., Cocanour, C.S., Moore, F.A. (2000). Tissue hemoglobin O2 saturation during resuscitation of traumatic shock monitored using near infrared spectrometry. J. Trauma, 48:637-642.

McKinley, B.A., Parmley, C.L., Butler, B.D. (1998). Skeletal muscle PO2, PCO2, and pH in hemorrhage, shock, and resuscitation in dogs. J. Trauma, 44:119-127.

McKinley, B.A., Ware, D.N., Marvin, R.G., Moore, F.A. (1998). Skeletal muscle pH, PCO:, and PO2 during resuscitation of severe hemorrhagic shock. J. Trauma, 45:633-636.

Meier-Hellmann, A., Reinhart, K. (1995). Effects of catecholamines on regional perfusion and oxygenation in critically ill patients. Acta Anaesthesiol. Scand. Suppl., 107:239-248.

Morgan, T.J., Venkatesh, B., Endre, Z.H. (1997). Continuous measurement of gut luminal PCO2 in the rat: responses to transient episodes of graded aortic hypotension. Crit. Care Med., 25:1575-1578.

Nordin, A., Makisalo, H., Mildh, L., Hockerstedt, K. (1998). Gut intramucosal pH as an early indicator of effectiveness of therapy for hemorrhagic shock. Crit. Care Med. 26:1110-1117.

Pernat, A., Weil, M.H., Tang, W., Yamaguchi, H., Pernat, A.M., Sun, S., Bisera, J. (1999). Effects of hyper- and hypoventilation on gastric and sublingual PCO2. J. Appl. Physiol., 87:933-937.

Povoas, H.P., Weil, M.H., Tang, W., Moran, B., Kamohara, T., Bisera, J. (2000). Comparisons between sublingual and gastric tonometry during hemorrhagic shock. Chest, 118:1127-1132.

Povoas, H.P., Weil, M.H., Tang, W., Sun, S., Kamohara, T., Bisera, J. (2001). Decreases in mesenteric blood flow associated with increases in sublingual PCO2 during hemorrhagic shock. Shock, 15:398-402.

Powell, C.C., Schultz, S.C., Burris, D.G., Drucker, W.R., Malcolm, D.S. (1995). Subcutaneous oxygen tension: a useful adjunct in assessment of perfusion status. Crit. Care Med., 23:867-873.

Puyana, J.C., Soller, B.R., Parikh, B., Heard, S.O. (2000). Directly measured tissue pH is an earlier indicator of splanchnic acidosis than tonometric parameters during hemorrhagic shock in swine. Crit. Care Med. 28:2557-2562.

Rosser, D.M., Stidwill, R.P., Millar, C.G., Singer, M. (1995). The effect of norepinephrine and dobutamine on bladder epithelial oxygen tension. Chest, 108:1368-1372.

Rozenfeld, R.A., Dishart, M.K., Tonnessen, T.I., Schlichtig, R. (1996). Methods for detecting local intestinal ischemic anaerobic metabolic acidosis by PCO2. J. Appl. Physiol., 81:1834-1842.

Ruffolo, D.C. (1998). Gastric tonometry: early warning of tissue hypoperfusion. Crit. Care Nurs. Q., 21:26-32.

Sakka, S.G., Reinhart, K., Wegscheider, K., Meier-Hellmann, A. (2001). Variability of splanchnic blood flow in patients with sepsis. Intensive Care Med., 27:1281-1287.

Sato, Y., Well, M.H., Tang, W., Sun, S., Xie, J., Bisera, J., Hosaka, H.. (1997). Esophageal PCO2 as a monitor of perfusion failure during hemorrhagic shock. J. Appl. Physiol., 82:558-562.

Schlichtig, R. Heard, S.O. (1999). Sublingual PCO2 measurement: the nitroglycerin of monitoring? Crit. Care Med., 27:1380-1381.

Shoemaker, W.C., Fink, S., Ray, C.W., McCartney, S. (1984). Effect of hemorrhagic shock on conjunctival and transcutaneous oxygen tensions in relation to hemodynamic and oxygen transport changes. Crit. Care Med.,12:949-952.

Sims, C., Seigne, P., Menconi, M., Monarca, J., Barlow, C., Pettit, J.,Puyana, J.C. (2001). Skeletal muscle acidosis correlates with the severity of blood volume loss during shock and resuscitation. J. Trauma, 51:1137-1146.

Singer, M., Millar, C., Stidwill, R., Unwin, R. (1996). Bladder epithelial oxygen tension—a new means of monitoring regional perfusion? Preliminary study in a model of exsanguination/fluid repletion. Intensive Care Med., 22:324-328.

Singer, M., Rosser, D., Stidwill, R. (1995). Bladder epithelial oxygen tension as a marker of organ perfusion. Acta Anaesthesiol. Scand. Suppl., 107:77-80.

Soller, B.R., Heard, S.O., Cingo, N.A., His, C., Favreau, J., Khan, T.,Ross, R.R., Puyana, J.C. (2001). Application of fiberoptic sensors for the study of hepatic dysoxia in swine hemorrhagic shock. Crit. Care Med., 29:1438-1444.

Third European Consensus Conference in Intensive Care Medicine (1996). Tissue hypoxia: how to detect, how to correct, how to prevent? Am. J. Crit. Care Med., 154:1573-1578.

Vallet, B., Lund, N., Curtis, S.E., Kelly, D., Cain, S.M. (1994). Gut and muscle tissue P02 in endotoxemic dogs during shock and resuscitation. J. Appl. Physiol., 76:793-800.

Venkatesh B. Clutton Brock TH, Hendry SP. (1994). A multiparameter sensor for continuous intra-arterial blood gas monitoring: a prospective evaluation. Crit. Care Med., 22:588-594.

Venkatesh, B., Morgan, T.J., Lipman, J. (2000). Subcutaneous oxygen tensions provide similar information to ileal luminal CO2 tensions in an animal model of haemorrhagic shock. Intensive Care Med., 26:592-600.

Walley, K.R., Friesen, B.P., Humer, M.F., Phang, P.T. (1998). Small bowel tonometry is more accurate than gastric tonometry in detecting gut ischemia. J. Appl. Physiol., 85:1770-1777.

Weil, M.H. (2000). Tissue PCO2 as universal marker of tissue hypoxia. Minerva Anestesiol. 66:343-347. Minerva Anestesiol. 66:343-347.

Weil, M.H., Nakagawa, Y., Tang, W., Sato, Y., Ercoli, F., Finegan, R.,Grayman, G., Bisera, J. (1999). Sublingual capnometry: a new noninvasive measurement for diagnosis and quantitation of severity of circulatory shock. Crit. Care Med., 27:1225-1229.

Lund, C., Kuller, J., Lane, A., Lott, J.W., Raines, D.A.. (1999). Neonatal skin care: the scientific basis for practice. Neonatal Netw., 18(4); JOGNN: p. 241-254.

C.L. Waltemath, Oxygen, uptake, transport and tissue utilization, Anesth.Analog. 49 (1970), pp. 184-203.

Centers for disease control: increase in national hospital discharge survey rates for septicemia- United States 1979-1987 JAMA. 1990, 263:937-938.

D.C. Angus, W.T. Linde-Zwirble, G. Clermont, J. Carcillo, M. R. Pinsky, Epidemiology of severe sepsis in the United States:Analysis of incidence, outcome, and associated costs of care. 2001, Crit. Care Med., 29:1303-1310.

A. Barber et al., Shock. In:Principles of surgery. 1994, S.I. Schwartz et al. (Eds.), 7th edition. McGraw-Hill, NY, pp. 101-122.

W.F. Ganong, Review of Medical Physiology. 1991, pp. 578-579, 588-589 Appelton & Lange Medical book.

G. Clerici, R. Luzietti and G.C. Di Renzo, Monitoring of Antepartum and intrapartum fetal hypoxemia: pathophysiological basis and available techniques. Biology Neonate, 2001, 79:246-253.

J.A. Kruse, Searching for the perfect indicator of dysoxia, Crit. Care Med. 1999, 27:469-470.

M.P. Fink, Cytopathic Hypoxia: Mitochondrial dysfunction as mechanism contribution to organ dysfunction in Sepsis, Critical Care Clinics. 2001, 17: 219-237.

A. Mayevsky & B. Chance, Intracellular Oxidation-Reduction State Measured in Situ by a Multichannel Fiber-Optic Surface Fluorometer. Science, 1982, 217: 537-540.

T. Manor, A. Meilin, & A. Mayevsky. Monitoring different areas of the rat cortex in response to fluid percussion trauma. Israel J Med Sci, 1996, 32, Supplement, S39.

A. Mayevsky, A. Kraut, T. Manor, J. Sonn, & Y. Zurovsky, Optical monitoring of tissue viability using reflected spectroscopy in vivo. Tuchin, V. V. Optical technologies in biophysics and medicine II. Proceeding of SPIE, 2000, 4241: 409-417saratov, Russia.

A. Mayevsky, A. Meilin, G.G. Rogatsky, N. Zarchin, & J. Sonn, Multiparametric monitoring of the awake brain exposed to carbon monoxide. Journal of Applied Physiology, 1995, 78, 1188-1196.

Jobsis, F., et al; "Intracellular Redox Changes in Functioning Cerebral Cortex I. Metabolic Effects of Epileptiform Activity"; 1971; Neurophysiology; vol. 3465; pp. 735-749.

Stern, M.D.; "In Vivo Evaluation of Microcirculation by Coherent Light Scattering"; Mar. 6, 1975; Nature; vol. 254; pp. 56-58.

Kramer R.S. et al; "Cerebral Cortical Microfluorometry at Isobestic Wavelengths for Correction of Vascular Artifact"; Aug. 17, 1979; Science; vol. 205; pp. 693-696.

Pologe, J.; "Pulse Oximetry: Technical Aspects of Machine Design"; 1987; Int. Anesthesiol. Clin.; vol. 25(3); pp. 137-153.

Rampil, I., et al; "Correlated, Simultaneous, Multiple-Wavelength Optical Monitoring In Vivo of Localized Cerebrocortical NADH and Brain Microvessel Hemoglobin Oxygen Saturation"; Jul. 1992; Journal of Clinical Monitoring; vol. 8; pp. 216-225.

Kessler,M.; Frank,K. The Erlangen micro—light guide spectrophotometer EMPHO I. In: Frank,K.; Kessler,M., eds. Quantative Spectroscopy in Tissue. Germany: Die Deutschen Bibliothek—CIP—Einheitsaufnahme.; 1992: 61-74.

Kobayashi, S. et al; "Optical Consequences of Blood Substitution on Tissue Oxidation-Reduction State Microfluorometry"; Jun. 1971; J. Appl. Physiol.; vol. 31; No. 1; pp. 93-96.

Renault, G. et al; "In situ Double Beam NADH Laser Fluorimetry: choice of a reference wavelength"; Copyright 1984; American Physiological Society; pp. H491-H499.

Mayevsky, A. et al; "Repetitive Patterns of Metabolic Changes During Cortical Spreading Depression of the Awake Rat"; 1974; Brain Research; vol. 65; pp. 529-533.

Harbig, K., et al; "In vivo Measurement of Pyridine Nucleotide Fluorescence from Cat Brain Cortex"; Oct. 1976; J. Appl. Physiol.; vol. 41; No. 4; pp. 480-488.

Taitelbaum, H.; "Optical Penetration Depth in Layered Tissues"; 1994; OSA Proceeding on Advances in Optical Imaging and Photon Migration; vol. 21; pp. 305-309.

Eggert, H., et al; "Optical Properties of Human Brain Tissue, Meninges, and Brain Tumors in the Spectral Range of 200 to 900 nm"; Copyright 1987; Neurosurgery; vol. 21; No. 4; pp. 459-464.

American National Standard; "American National Standard for Safe Use of Lasers"; 2000; ANSI Z136.1; pp. i., ii., 41-51.

International Standard; "Safety of Laser Products"; 2001; IEC 60825-1; Edition 1.2; 5 pages.

Kobayashi, S., et al; "Microfluorometry of Oxidation-Reduction Rate of the Rat Kidney in situ"; Nov. 1971; J. Appl. Physiol.; vol. 31; No. 5; pp. 693-696.

Anderson, R. et al; "Microvasculature Can be Selectively Damaged Using Dye Lasers: A Basic Theory and Experimental Evidence in Human Skin"; 1981; Lasers in Surgery and Medicine; vol. 1; pp. 263-276.

* cited by examiner

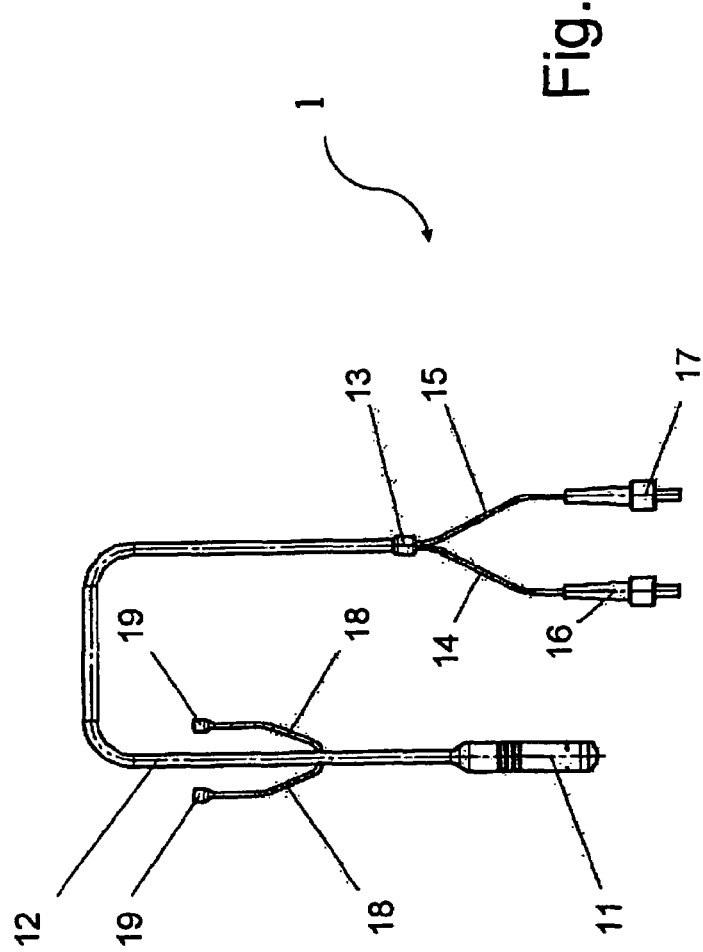
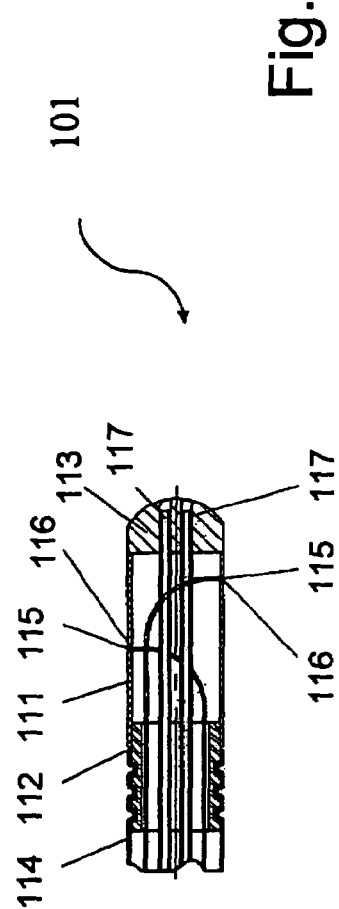

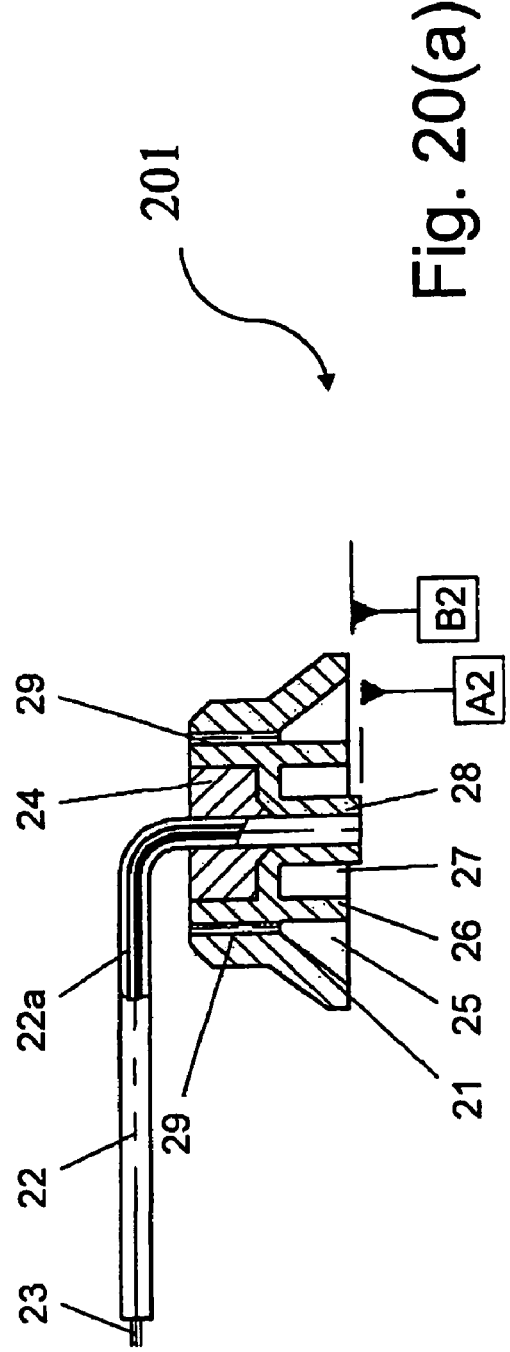
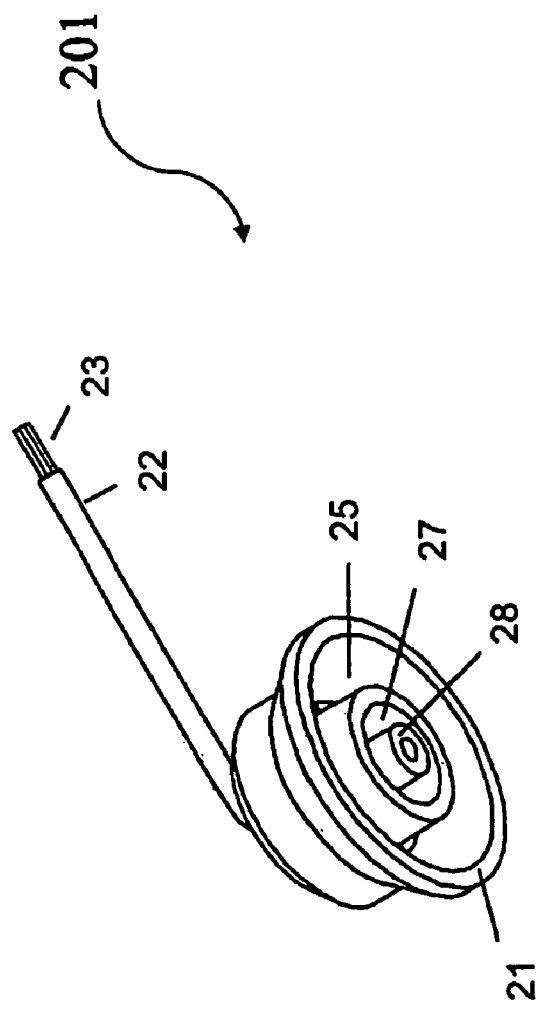
Fig. 20(a)
Fig. 20(b)

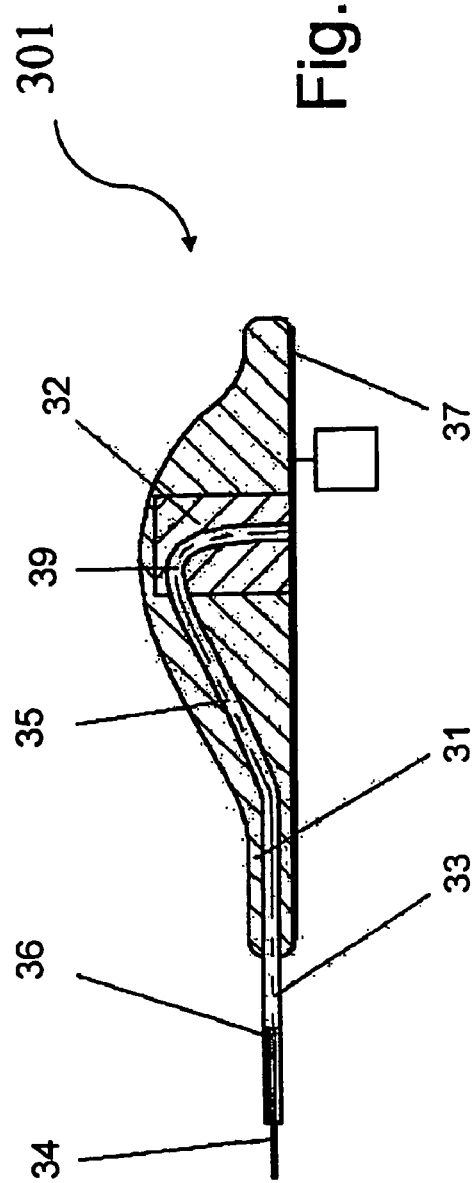
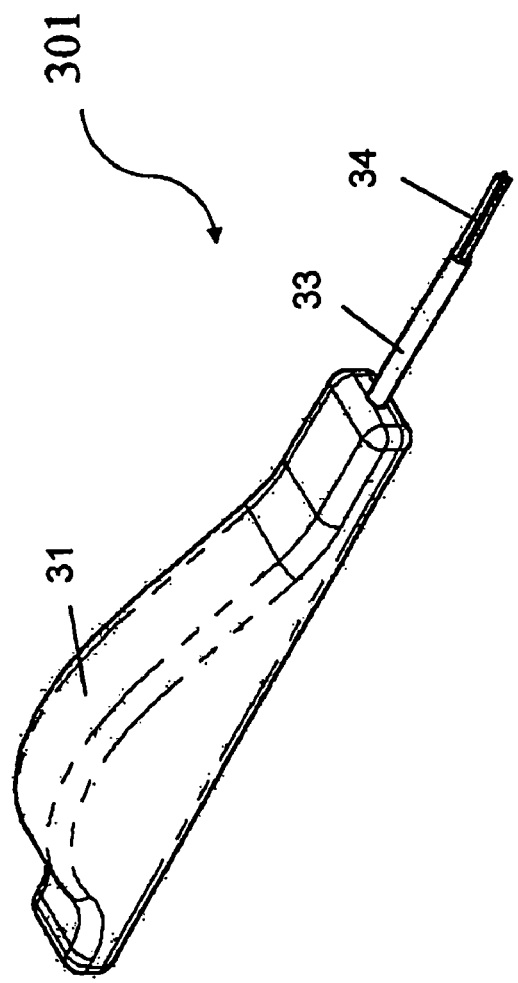
Fig. 21(a)
Fig. 21(b)

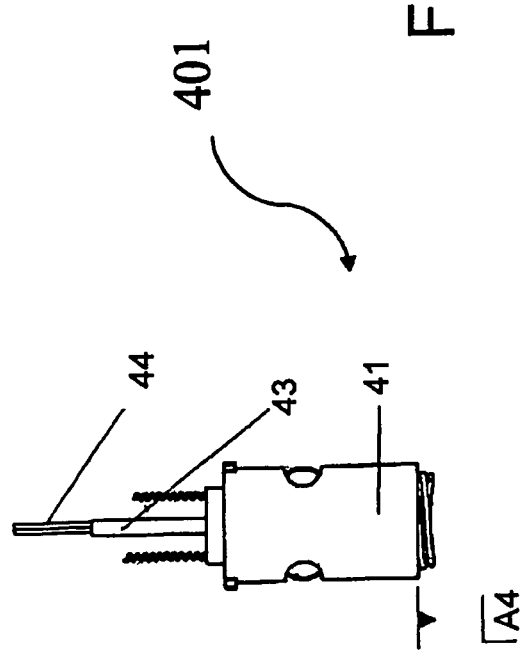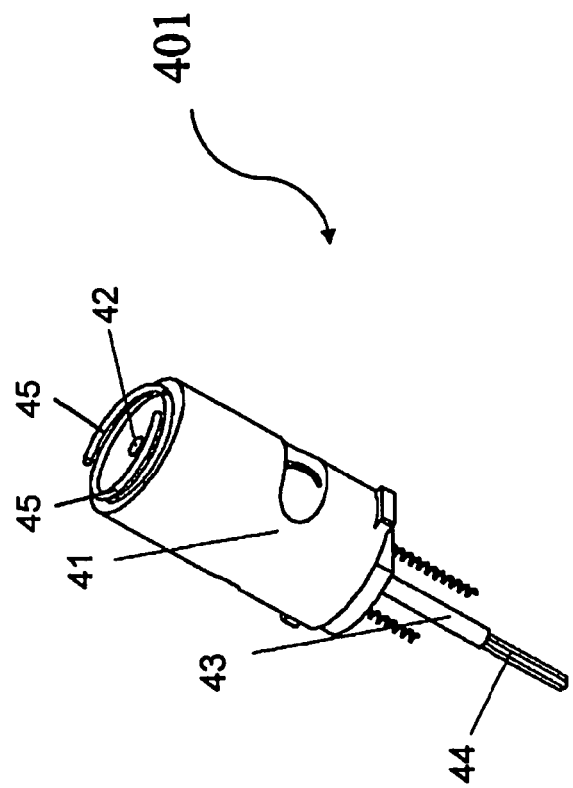
Fig. 22(a)
Fig. 22(b)

DIAGNOSIS OF BODY METABOLIC EMERGENCY STATE

FIELD OF THE INVENTION

The present invention relates to the early diagnosis of body metabolic emergency state that may develop in many acute or chronic clinical conditions. In particular, the invention is directed to a multiparametric method, system and apparatus for the monitoring of tissue blood flow, tissue reflectance, tissue oxy-deoxy hemoglobin saturation and mitochondrial (NADH) Nicotin-amide adenine dinucleotide and Flavoproteins (Fp) redox state. More particularly, the invention is concerned with measuring such parameters in real time for the most sensitive tissue or organ in the body to stress situations and sympathetic stimulation, in order to enable early diagnosis of emergency metabolic state of the body, particularly useful in facilitating formulation and navigation of the treatment given to the patient.

BACKGROUND OF THE INVENTION

The human body is totally dependent upon continuous supply of Oxygen ($O_2$) utilized by various tissues and cells in order to transfer energy from food components into the high-energy phosphate molecules named ATP (Adenosine-Tri-Phosphate). Most of the $O_2$ absorbed in the body (>95%) is utilized by the mitochondria (C. L. Waltemath, Oxygen, uptake, transport and tissue utilization, Anesth.Analog. 49 (1970), pp. 184-203), which produces 95% of the ATP in normal tissues, as illustrated in FIG. 1. When $O_2$ supply will be restricted or limited the production of ATP will decrease and as a result, cellular functions will be affected (inhibition of pumping activity for example).

In general terms, when the balance between $O_2$ supply and $O_2$ demand is negative the function of the tissue or organ will be affected and a pathological state is developed. Typical examples to a severe negative $O_2$ balance are heart attack or stroke where due to occlusion of blood vessel in the heart or the brain the supply of $O_2$ to a specific region in the vital organ will be limited and the function will be inhibited. These two examples represent dramatic and acute pathological events and the diagnosis of such conditions is relatively easy and fast. In a large segment of critically ill patients the changes in $O_2$ balance is a slow process developed in one or more areas of the body and may end up in morbidity and mortality in large number of patients. A typical example of such a pathological state is sepsis, which is a major cause of death in many patients hospitalized in intensive care units (ICUs) or even in regular hospital departments.

The Centers for Disease Control (CDC) published data about the dynamic of the population size suffered from sepsis. In 1990 they estimated, in the USA, 450,000 cases of sepsis per year with more than 100,000 deaths (Centers for disease control: increase in national hospital discharge survey rates for septicemia—United States 1979-1987 JAMA. 1990, 263:937-938). In 2001, Angus et al estimated that the number of sepsis patients will grow to 934,000 in 2010, and to 1,110,000 in 2020 (D. C. Angus, W. T. Linde-Zwirble, G. Clermont, J. Carcillo, M. R. Pinsky, demiology of severe sepsis in the United States:Analysis of incidence, outcome, and associated costs of care. 2001, Crit. Care Med., 29:1303-1310). They concluded that "Severe sepsis is a common, expensive and frequently fatal condition, with as many deaths annually as those from acute myocardial infarction".

Sepsis represents a large group of patient illnesses in which the deterioration of $O_2$ balance is very hard to identify and the consequences in many cases are fatal. The various groups of "slow killing" pathologies (like sepsis) are very hard to diagnose due to lack of specific and sensitive enough techniques or methods. Other examples include hypotension, systemic hypoxemia, or acute Respiratory Distress Syndrome (ARDS). The same problem of $O_2$ imbalance may develop in preterm or full term infants hospitalized in the neonatal ICU or even in the newborn during delivery. The total number of patients suffer annually from shock, trauma and sepsis is 1.5 million with costs above US$50 billion (Ruffolo, 1998).

Body Homeostatic Compensatory Mechanisms

Under mild emergency situations, where body $O_2$ is interrupted, some mechanisms of preserving body homeostasis may take place and may return the body to its steady state conditions. Under moderate or severe $O_2$ imbalance or the development of emergency pathological state, such as sepsis or severe hypotension for example, the body will not be able to compensate completely the deficit of $O_2$.

It is well known and documented that the Autonomic Nervous System (ANS) and mainly its sympathetic branch, including the adrenal gland (secretion of Adrenaline), dominate the compensatory mechanisms of the body related to $O_2$ deficiency. The rapid compensatory reaction to decrease in blood volume (hypovolemia for example), appears in all textbooks of physiology (i.e. W. F. Ganong, Review of Medical Physiology. 1991, pp 578-579, 588-589 Appelton & Lange Medical book). This includes redistribution of blood flow to various organs and giving preference to the most vital organs in the body, namely to the, brain, heart and adrenal glands (A. Barber et al., Shock. In: Principles of surgery. 1994, S. I. Schwartz et al. (Eds.), $7^{th}$ edition. McGraw-Hill, N.Y., pp. 101-122).

In order to demonstrate the significance of the present invention a typical emergency $O_2$ imbalance in a clinical situation is demonstrated hereinafter. The field of fetal distress or hypoxemia including the monitoring approaches during delivery were reviewed in 2001 by Clerici et al (G. Clerici, R. Luzietti and G. C. Di Renzo, Monitoring of Antepartum and intrapartum fetal hypoxemia: pathophysiological basis and available techniques. Biology Neonate, 2001, 79:246-253.) As they summarized "Due to the limitations of cardiotocography, additional information is required for appropriate decision making during labor. Current evidence suggests that modern technology applied to fetal surveillance can provide useful additional information that can improve our capacity to interpret fetal reaction to labor events".

Based on Clerici et al and other publications, including the inventors' own research activities, FIG. 2 illustrates the sequence of events that occur under fetal hypoxemia.

Thus, referring to FIG. 2, Placental hypoxia (I) can lead to changes in the delivery of $O_2$ to the fetus and as a result fetal hypoxemia may develop (II). Under this condition (limitation in $O_2$ supply), glycolysis (anaerobic metabolism) will be stimulated and the resulting increased production of lactic acid will be recognized as acidosis (decrease in blood pH). It is well known that under hypoxic conditions the fetus responds to acute or chronic lack of $O_2$ using various mechanisms.

In the acute phase of hypoxia, the fetus will decrease its biophysical activity in order to reduce total body $O_2$ consumption. This may increase $O_2$ supply to vital organs such as brain, adrenals and heart. The activated mechanism of vascular redistribution (III) will decrease blood flow to the kidneys, G-I tract as well as to the peripheral vasculature such as cutaneous and skeletal muscle vessels. This mechanism of redistribution of blood to various organs of the body, called "Brain Sparing Effect", may lead to "Fetal hemodynamic centralization". The involvement of higher levels of noradrenaline, due to the increased sympathetic activity (IV), will increase the oxygen delivery to the brain in order to avoid brain damage.

At this point in time there are two possible developments:
A. An appropriate response of the "brain sparing effect" to minimize the effect of hypoxemia on the fetus. If the cause for this condition will be resolved, the fetus will return to so call normal conditions and no damage to the brain will be recognized.
B. The development of a vicious cycle response or cascade of events. Under such conditions the centralization of blood will affect cardiac hemodynamics so that more blood will flow to the brain. During this phase the fetus will present an extreme response to the increasing hypoxemia and the fetal heart function will be impaired. This stage, known as the decompensatory phase may lead to brain damage including edema. The damage may be permanent.

In order to evaluate, in real time, the hemodynamic and metabolic state of the fetus, during labor, several approaches were developed and applied to clinical usage:
1. Doppler velocitometry of the major arteries, namely, aorta, femoral artery, renal artery or the main arteries supplying the brain. During the initial phase the Doppler technique is not a sensitive tool for detecting changes in the uteroplacental vascular bed or gas exchange and metabolites. It is important to note that Doppler velocitometry is more meaningful during the progression of fetal hypoxemia.
2. Fetal Heart Rate, which may be monitored externally by placing sensors on the mother's abdomen or internally by an electrode attached to the fetal scalp.
3. Uterine Contraction pressure may be monitored by placing a sensor in the uterine cavity or by external monitor.
4. Pulse Oximetry can provide real time values of fetal arterial blood saturation with oxygen ($SpO_2$). The probe is placed between the uterine wall and fetal cheek. The level of $SpO_2$ could be used as a warning signal to fetal hypoxemia.
5. Sampling of scalp blood for the measurement of pH is done whenever fetal hypoxemia is suspected as indicated by the scalp heart rate monitor.

The disadvantage of this approach is that the information obtained is not in real time mode.

The right side of FIG. 2 shows typical directional changes recorded in the various organs after the sympathetic stimulation. As seen, the blood flow to the brain and the heart increased while the energy state of the non-vital organs is deteriorated. All the possible monitored parameters will indicate this trend although in practice only few parameters were monitored.

Pathophysiology of Critically Ill Patients

The same pattern of pathophysiological cascade of events may occur in many emergency clinical situations in adult patients and may lead to morbidity and mortality. Such situations may include tissue hypoxia, which was discussed in detail during the consensus conference (1996). As shown in FIG. 3, various pathological states may lead to metabolic disturbances and may end up in cellular energy derangement (Hotchkiss and Karl, 1992; Marik and Varon, 1998; Ince and Sinaasappel, 1999; Meier-Hellmann and Reinhart, 1995).

The six pathological states, shown in the left side of FIG. 3, are the most common events that may develop in clinical practice. The states may develop due to specific clear event, such as a major operation such as heart bypass, brain operation, organ transplant, during the operation as well as during the post-operative period, or during slow process of body deterioration, such as in sepsis or shock. The definition of each of those 6 states is not so well established and some overlapping may exist. Under all those situations the metabolic state of the body will be deteriorated and energy failure will develop. In the right side of FIG. 3 the list of clinical situations given include most of the major clinical situations, such as trauma, perinatal, intra-operative period, post-operative period, and internal medicine, typically treated by major hospitals.

As a central protection mechanism, blood flow redistribution will occur and the three protected organs (brain, heart and adrenal gland) will receive more blood and $O_2$, while the peripheral organs or areas (skin and muscles), as well as other non vital visceral organs, will undergo vasoconstriction and a decrease in blood flow and $O_2$ supply will occur.

Monitoring of Critically Ill Patients in Medical Practice

As shown in FIG. 2 and FIG. 3, under various severe pathophysiological conditions the compensatory mechanisms of blood flow redistribution is taking place and as a result the sympathetic stimulation will induce significant decrease in tissue oxygenation in non-vital organs and tissues. Under these conditions the vital organs of the body are protected by preserving high blood flow and $O_2$ supply.

The search for a significant or perfect indicator as well as the most representative organ or tissue in the body to be monitored is an ongoing process. Ince and Sinaasappel (1999) concluded that "To evaluate the severity of microcirculatory distress and the effectiveness of resuscitation strategies, new clinical technologies aimed at the microcirculation will need to be developed. It is anticipated that optical spectroscopy will play a major role in the development of such tools". In a recent published paper Kruse summarized the effort done, by various investigators regarding the perfect indicator of dysoxia, which could be defined as a state of supply-dependent oxygen consumption (J. A. Kruse, Searching for the perfect indicator of dysoxia, Crit. Care Med. 1999, 27:469-470). It is possible to divide the various existing monitoring devices or parameters according to the monitoring site as shown in FIG. 4. The systemic monitoring site is defined as a parameter represents the cardiovascular, respiratory systems or the circulated blood.

The list of parameters in the local monitoring site is divided into the two groups according to its significant value in keeping the organism alive under severe emergency situations. The monitored parameters listed under low or non vital organs, are divided to those published already in the literature, and the group of parameters included in the MPA (Multi Parametric Approach) which is part of the present invention.

Kruse (1999) suggests that during systemic insults that result in globally diminishing $DO_2$ (Delivery of $O_2$), dysoxia probably manifested in the splanchic region before it can be detected by systemic measurements. In another paper M. P. Fink reviewed the possible involvement of mitochondrial dysfunction in organ failure developed in sepsis (M. P. Fink, Cytopathic Hypoxia: Mitochondrial dysfunction as mechanism contribution to organ dysfunction in Sepsis, Critical Care Clinics. 2001, 17: 219-237). He came to a very important conclusion regarding the type of parameter to be monitored in septic patients. Fink wrote that the effort to improve outcome in patients with sepsis by monitoring and manipulating cardiac output, systemic $DO_2$, and regional blood flow are doomed to failure; instead, the focus should be on developing pharmacological strategies to restore normal mitochondrial function and cellular energetics. Nevertheless, Fink does not suggest that any particular parameters should be monitored to achieve such a goal, less so how to monitor such parameters The search for an early indication for multiorgan failure is an ongoing process for the last 10 years. Most of the studies were performed in animal experiments. Shoemaker et al. (1984) compared tissue $PO_2$ in conjuctival and transcutaneous areas. Most of the effort was directed toward the development of real time monitoring device for the spelnchnic metabolic state (Fink, 1991; Fiddian-Green and Baker, 1987; Hasibeder et al., 1996). The most recent papers will be cited as follows. Rozenfeld et al. (1996) used $PCO_2$ electrode attached to the mucosal side of the intestine. Sato et al. (1997) measured the same parameter in the esophagus during hemorrhagic shock. They found that esophageal tonometry may serve as a practical alternative to gastric tonometry suggested by various investigators (i.e. Ruffolo, 1998 and Bloechle et al., 1999).

In a rat model Morgan et al. (1997) monitored $PCO_2$ in the ileum during reduction in aortic pressure. In a pig model Knichwitz et al used the intramucosal $PCO_2$ as an indicator to intestinal hypoperfusion.

In order to simplify the monitoring approach Weil et al. (1999), Povas et al. (2001), Marik, (2001), Weil (2000), Schlichtig and Heard (1999), suggested monitoring $PCO_2$ in the sublingual area, which is the most proximal area of the G-I tract. They found that such a measurement could serve as a good indicator to the severity of circulatory shock.

Pernat et al. (1999) and Povas et al. (2000) compared the gastric and sublingual $PCO_2$ as indicators for impaired tissue perfusion. They found similar changes under hemorrhagic shock. In a pig model Puyana et al. (2000) measured abdominal wall muscle. They concluded that pH was the most sensitive site as compared to the stomach or the abdominal wall muscle. Vallet et al. (1994) compared gut and muscle $PO_2$ in endotoxemic dogs. Sakka et al. (2001) assessed the variability of spalachnic blood flow during stable global hemodynamics in septic patients and compared it to gastric tonometry. Boekstegers et al. (1994) measured skeletal muscle $PO_2$ in patients with sepsis. Nordin et al. (1998), Walley et al. (1998) and Dubin et al. (2001) measured intramucosal pH in different segments of the gastrointestinal tract under hemorrhagic shock. The same approach of monitoring gastric $PCO_2$ was used in patients after subarachnoid hemorrhage by Koivisto (2001). The next step was to compare various tissue parameters monitored simultaneously in the skeletal muscle under hemorrhagic shock. Mckinley et al. (1998) monitored $PO_2$, $PCO_2$ and pH in dogs under hemorrhagic shock and also in a patient. Mckinley and Butler (1999) used a fiber optic probe and compared gastric tonometry ($PCO_2$, pH) to muscle $PO_2$, $PCO_2$ and pH in hemorrhagic shock. They concluded that muscle monitoring was more sensitive as compared to gastric tonometry on systemic parameters. To evaluate the changes and severity of blood loss as well as the efficacy of the resuscitation process, Sims et al. (2001) used skeletal muscle monitoring of $PO_2$, $PCO_2$ and pH and found the correlation with the severity of blood loss and resuscitation. The same approach was used in the liver by Soller et al. (2001). In 1995 Powell et al. measured subcutaneous oxygen tension in rats as an indicator of peripheral perfusion. Using the same idea, Venkatesh et al. (1994, 2000) compared subcutaneous $PO_2$ to ileal luminal $PCO_2$ in animal model of hemorrhagic shock, subcutaneous $PO_2$ was more sensitive parameter.

Another approach to monitor organ perfusion outside the G-I tract was described by Rossen et al. (1995). They found that the epithelial $PO_2$ in the bladder was responsive to norepinephrine in a rat model. Rosser et al. (1995) and Singer et al. (1995) used $PO_2$ electrodes in the bladder exposed to sepsis or hemorrhage. Singer et al. (1996) repeated those studies in a model of fluid repletion. Lang et al. (1999) monitored $PO_2$, $PCO_2$ and pH in the bladder during ischemia and reperfusion. Clavijo et al. (2002) monitored pH and $PCO_2$ in the gut as well as in the bladder wall mucosa and found comparable changes in the two organs under shock in a pig model.

Studies in vitro had shown that the urethra was more sensitive to ischemia as compared to the bladder. (Bratslavsky et al., 2001).

Other approaches to monitor $HbO_2$ saturation and cytochrome aa3 redox state were done by various groups in animals as well as in patients (Cairns et al., 1997; Guery et al., 1999 and Mckinley et al., 2000). In patients, Jakob and Takala evaluated the variability of spalanchnik blood flow in patients with sepsis.

In U.S. Pat. Nos. 6,258,046, 6,216,024, devices and methods are described for assessing perfusion failure, by measuring the partial pressure of carbon dioxide ($PCO_2$) in the gastrointestinal tract, or the upper digestive and/or respiratory tract of a patient. In U.S. Pat. Nos. 6,071,237 and 5,579,763 devices and methods are described for assessing perfusion failure, by measuring the partial pressure of carbon dioxide in the lower respiratory tract or the digestive system of a patient. In U.S. Pat. Nos. 6,330,469 and 6,216,032, a method and apparatus are described for early diagnosis of a potentially catastrophic illness in a premature newborn infant, in which the heart rate variability in the infant is monitored continuously, and in which at least one characteristic abnormality in the heart rate variability that is associated with the illness. None of these patents discloses or suggests the parametric monitoring for determining early diagnosis of body metabolic emergency state that may develop in many acute or chronic clinical conditions.

FIG. 5 shows the Hemodynamic and Metabolic responses of 4 different organs to norepinephrine injection, intravenously administered during experiments by Applicant. Measurements were done in the Brain (B), Kidney (K), Liver (L) and Testis (T) by placing a surface optical probe on each one of the 4 organs of a rat. Four different monitored parameters are presented for each organ, namely, Reflectance (Ref), Fluorescence (Flu), Corrected NADH fluorescence (NADH) and microcirculatory blood flow (TBF). The monitoring was done by a 4 channel fluorometer reflectometer (A. Mayevsky & B. Chance, Intracellular Oxidation-Reduction State Measured in Situ by a Multicannel Fiber-Optic Surface Fluorometer. Science, 1982, 217: 537-540) and 4 laser Doppler flowmeters (T. Manor, A. Meilin, & A. Mayevsky. Monitoring different areas of the rat cortex in response to fluid percussion trauma. Israel J Med Sci, 1996, 32, Supplement, S39; A. Mayevsky, A. Kraut, T. Manor J. Sonn, & Y. Zurovsky, Optical monitoring of tissue viability using reflected spectroscopy in vivo. Tuchin, V. V. Optical technologies in biophysics and medicine II. Proceeding of SPIE, 2000, 4241: 409-417 saratov, Russia; A. Mayevsky, A. Meilin, G. G. Rogatsky, N. Zarchin, & J. Sonn, Multiparametric monitoring of the awake brain exposed to carbon monoxide. Journal of Applied Physiology, 1995, 78, 1188-1196). As seen in FIG. 5, the injection of norepinephrine gave a clear preference to brain oxygenation as compared to the "non vita" organ, namely the kidney, liver and the testis. The blood flow (TBF) was dramatically increased while in the other organs TBF decreased significantly. The reflectance showed a clear decrease in the brain due to a vasodilatation response. The fluorescence and the corrected fluorescence (NADH) showed an oxidation in the brain while in the other 3 organs NADH became reduced (increased signal) due to the lack of $O_2$. It is important to note that all parameters were monitored simultaneously in the same animal.

FIG. 6 shows a comparison of the hemodynamic and metabolic responses to ischemia (left side of figure) and adrenaline injection (right side of figure) in the rat brain (B) and skin (S) in the scalp area. Three parameters are presented for each organ, namely, Reflectance (R-B, R-S), NADH redox state (NADH-B, NADH-S) and microcirculatory blood flow (TBF-B, TBF-S). Ischemia was induced by occlusion of the two carotid arteries which provide blood to the two monitored areas. The monitoring devices were used as in FIG. 5 although only two channels were used.

Under occlusion of the two carotid arteries, complete ischemia was induced in the two locations as expected. Under adrenaline, the preference was given to the brain, thus blood flow increased while NADH became more oxidized (decreased signal). In the skin, blood flow decreased to very low values and NADH increased significantly.

In FIG. 7 and FIG. 8 the comparison between brain and the small intestine is shown under anoxia and norepinephrine injection IV. Here again, when the massive insult was affecting the $O_2$ availability in the two locations, at the same time, the responses were similar in terms of mitochondrial function. Under anoxia (FIG. 7), NADH increased in the intestine and the brain while blood flow changes were completely reversed in the two organs. This is a result of the autoregulatory mechanism trying to protect the brain under anoxia by increasing blood flow. When norepinephrine was injected, the preference of the brain was clear as compared to the shut down of blood flow and $O_2$ to the intestine.

The same relationship between brain and small intestine are shown in FIG. 9 and FIG. 10 but the probe was located on the serosal side (outside) of the intestine, while in FIG. 7 and FIG. 8, the measurements were taken in the mucosal side (inside) of the small intestine.

The Significance of Multiparametric Monitoring of Tissue's Pathophysiological State.

It is important to note that the diagnostic value of a real time monitoring system in patients is dependent upon the following criteria:
A. The anatomical site in the body where the monitoring probe is located.
B. The compartment of the tissue of which the monitored parameter is originated, i.e. vascular, extracellular, cytosolic space or intra mitochondrial space. A combination of more than one compartment is also possible.
C. The type of the monitored parameter and its significance in terms of physiological and biochemical processes.

Criteron A

The following monitored anatomical sites were published in various publications:
1. Skin—Transcutaneuous, Sub Cutaneuous, and Conjuctiva.
2. Muscle—Skeletal Muscle, Abdominal wall muscle.
3. Gastro-Intestinal tract—Sublingual, Stomach and Small intestine.
4. Urogenital System—Bladder, Urethra. The difference between various organs is significant in the easiness of anchoring the probe to the tissue and the stability of the measurement. Also, in clinical application of the probe, it is important to attach the probe to other devices.

Criterion B

Most of the parameters monitored and published represent an average of number of tissue compartment mentioned. Tissue $PO_2$, $pCO_2$ or pH are monitored by insertion of the probe to the tissue or by locating the probe on the surface of the tissue. As a result, those three parameters represent the various compartments without any information regarding the relative contribution of each on the compartments. Therefore the results of $PO_2$, $PCO_2$ or pH could be sensitive to other factors in tissue physiology such as blood flow. The measurement of microcirculatory blood flow provides information on the intravascular compartment. This parameter together with the oxygenation level of the $HbO_2$ (Hemoglobin Saturation), that could be measured by visible or NIR spectroscopy, represent the supply of $O_2$ to the examined tissue. Therefore, it is possible to describe the relationship between $O_2$, Supply and Demand in a different but a parallel way as compared to Ruffolo (1998).

Referring to FIG. 11, in A, under normal conditions, the supply of $O_2$ is adequate and meet the demand as that mitochondrial function can be in the normal range (state 4-state 3 range) as described by chance & Williams in 1955. When the supply is diminished to a level that both flow and $O_2$ extraction reached its maximal compensation the critical point reached will induce a decrease in $O_2$ consumption and inhibition of oxidative phosphorylation (B). When the metabolic activity of the tissue/organ is stimulated, both demand and supply will increase (C) and mitochondrial activity will be stimulated to supply the extra ATP needed.

Under hypoxic conditions some organs, like the brain and heart that are autoregulated, supply will increase but mitochondrial activity is partially inhibited (D). Under those conditions, blood flow to the non-vital organs will be diminished and as a result the mitichondrial function will be inhibited. This process of blood flow redistribution is the basic concept, which is the theoretical basis to the current invention.

Criterion C

The various monitored parameters present in FIG. 11 represent various biochemical and physiological processes therefore the significance of each one of them is not identical in terms of early warning of emergency state developed in the body.

The most advanced technology is the monitoring of $PCO_2$ in various organs and mainly in the sublingual location. It is important to note the $CO_2$ is a by-product of the tricarboxlic acid cycle, which generates the NADH, which is later utilized by the mitochondria. The level of $CO_2$ is connected to various other processes, including the body acid-base balance and therefor the interpretation of the changes is dependent on various cellular and tissue activities.

Monitoring of pH has the same problematic disadvantage due to the various processes taking place in the acid-base balance. Two other parameters, $PO_2$ and $HbO_2$ are sensitive to blood flow and are not regulated processes. Both of them are dependent parameters and therefore are less sensitive to the significant metabolic processes. The other two parameters, TBF and mitochondrial NADH (Fp) are the most regulated processes and the relationship between them can vary in different pathological situations. Therefore monitoring each one of them alone is not sufficient due to coupling or uncoupling processes between the two parameters. Under decrease perfusion developed under hemorragic shock will always lead to an increases in the NADH levels in the mitochondria due to the lack of $O_2$. But those two parameters may behave differently during recovery processes, which are the most significant stages in diagnosis of the prognosis of the patient after acute emergency state.

In many instances blood flow will recover to the large blood vessels as well as to the microcirculation but the mitochondria will still be inhibited. Such conditions may be recorded under the development of pathological states such as sepsis or during recovery from hemorragic shock.

Therefore, and according to the present invention, for good diagnosis of a patient, multiparametric monitoring of the most regular processes in the tissue is necessary. Also, the quantification of the metabolic state of the organ, using optical techniques, namely, TBF and mitochondrial redox state, is practical under the multiparametric monitoring.

Due to the regulation of blood flow to various organs and the redistribution of TBF to the vital organs versus the non-vital organs, it is very clear that the entire organ will be regulated and the responses will be very similar in each part of the organ. Therefore it is not necessary to monitor all the parameters from the same volume of tissue. For this reason the various probes that monitor the various parameters could be separated from each other and the diagnosis will be valid.

As can be seen in FIG. 12, the urethra is very sensitive to sympathetic stimulation. Adrenaline was injected at time 0 and TBF decreased immediately to very low levels, together with an increase in NADH levels, due to a significant decrease in $O_2$ supply. The recovery to the normoxic level was very slow and a clear correlation between TBF and NADH can be seen.

Multiparametric Monitoring

Mammalian tissues are dependent upon the continuous supply of metabolic energy (such as ATP and phosphocreatine) in order to perform their various vital activities such as biosynthesis, ion transport and the like. Because the changes in tissue energy metabolism may have a transient nature or may be permanent, to assess the tissue energy-state, it is necessary to monitor the events continuously using a real-time system.

There is a direct correlation between energy metabolism of the cellular compartment and the blood flow in the microcirculation of the same tissue. In a normal tissue, any change in the $O_2$ demand will be compensated by a corresponding change in the blood flow to the tissue. By this mechanism, the $O_2$ supply remains constant if there is no change in the $O_2$ consumption. A change in blood flow will change the apparent energy state, so there is a significant correlation between the decrease in flow (increased ischemia) and the increase in NADH levels.

The parameters commonly used in the art for the assessment of tissue vitality include: A—Blood Flow Rate; B—Mitochondrial Redox State or the NADH Level; C—Blood Oxygenation State; D—Blood Volume; and E—Flavoprotein Concentration A—Blood Flow Rate The blood flow rate relates to the mean volume flow rate of the blood and is essentially equivalent to the mean velocity multiplied by the number of moving red blood cells in the tissue. This parameter may be monitored by a technique known as Laser Doppler Flowmetry, which is based on the fact that light reflected off moving red blood cells (RBC) undergoes a small shift in wavelength (Doppler shift) in proportion to the cell's velocity. Light reflected off of stationary RBC or bulk stationary tissue, on the other hand, does not undergo a Doppler shift.

By illuminating with coherent light, such as a laser, and converting the intensities of incident and reflected light to electrical signals, it is possible to estimate the blood flow from the magnitude and frequency distribution of those signals (Stern 1975, U.S. Pat. No. 4,109,647).

B—Mitochondrial Redox State or the NADH Level

The level of NADH, the reduced form of NAD, is dependent both on the availability of oxygen and on the extent of tissue activity. Referring to FIG. 13(*a*), whilst NADH absorbs UV light at wavelengths of about 310-400 nm and fluoresces at wavelengths of about 430-490 nm, the NAD does not fluoresce. The NADH Level can thus be measured using Mitochondrial NADH Fluorometry. The conceptual foundations for Mitochondrial NADH Fluorometry were established in the early 1950's and were published by Chance and Williams (Chance & Williams, 1955). They defined various metabolic states of activity and rest for in-vitro mitochondria.

An increase in the level of NADH with respect to NAD and the resulting increase in fluorescence intensity indicate that insufficient Oxygen is being supplied to the tissue. Similarly, a decrease in the level of NADH with respect to NAD and the resulting decrease in fluorescence intensity indicate an increase in tissue activity.

C—Blood Oxygenation State

The blood oxygenation state parameter refers to the relative concentration of oxyhaemoglobin to deoxy-haemoglobin in the tissue. It may be assessed by the performance of photometry measurements. The absorption spectrum of oxy-haemoglobin HbO2 is considerably different from the absorption spectrum of deoxy-haemoglobin Hb (Kramer & Pearlstein, 1979). The measurement of the absorption at one or more wavelengths can thus be used to assess this important parameter. Blood oximeters are based on measurement of the haemoglobin absorption changes as blood deoxygenates (Pologe, 1987). Such oximeters generally use at least two light wavelengths to probe the absorption. In these devices one wavelength is at an isosbestic point while the another wavelength is at a point that exhibits absorption changes due to variation in oxygenation level.

For monitoring the oxygenation levels of internal organs, fiber-optic blood oximeters have been developed. These fiber-optic devices irradiate the tissue with two wavelengths, and collect the reflected light through the optical fibers. By analysis of the reflection intensities at several wavelengths the blood oxygenation is deduced. The wavelengths used in one such system were 585 nm (isosbestic point) and 577 nm (Rampil et al., 1992). Another blood oximeter measures and analyzes the whole spectrum band 500-620 nm (Frank and Kessler, 1992).

The commercial pulse oximeters measure oxygenation of arterial blood rather then blood oxygenation in the tissue. These instruments utilize artery pulsation in order to extract absorption changes originated in arterial blood.

The wavelengths used in commercial pulse oximeters are typically around 660 nm in the red region of the spectrum, and between 800 to 1000 nm in near-infrared region (Pologe, 1987).

D—Blood Volume

The blood volume parameter refers to the concentration of the blood in the tissue. When tissue is irradiated, the intensity of reflectance 'R', at the excitation wavelength, from the tissue is informative of the blood volume. The intensity of the reflected signal, R, also referred to as the total backscatter, increases dramatically as blood is eliminated from the tissue as a result of the decrease in haemoglobin concentration. Similarly, if the tissue becomes more perfused with blood, R decreases due to the increase in the haemoglobin concentration. The excitation wavelength for R parameter is preferably at an isosbestic point of the absorption spectrum of oxy-deoxy hemoglobin, otherwise the reflectance measurements are influenced by the oxy-deoxy changes and require correction therefor.

E—Flavoprotein Concentration

In order to determine the metabolic state of various tissues in-vivo it is possible to monitor the fluorescence of another cellular fluorochrome, namely, Flavoproteins (Fp). Referring to FIG. 13(b), Fp absorbs light at wavelengths of about 410 to about 470 nm and fluoresces at wavelengths of about 500 nm to about 570 nm. The Fp level can thus be measured using Fp Fluorometry. The conceptual foundations for Fp Fluorometry were established in the late 1960's and were published in several papers as will be referenced hereinafter. Simultaneous monitoring of NADH and Fp from the same tissue provides better interpretation of the changes in energy production and demand.

Chance et al., 1971 had used a time-sharing fluorometer to record intracellular Redox State of NADH and Fp. They showed a very clear correlation between the two Chromophores to changes in $O_2$ supply to the perfused liver. Using a time sharing fluorometer reflectometer we had shown the simultaneous monitoring of NADH and Fp from the surface of the rat's brain (Mayevsky, 1976). The kinetics of the responses to anoxia or decapitation were identical for the NADH and Fp indicating that the NADH signal comes from the same cellular compartment as the Fp—the mitochondrion.

The five tissue viability parameters described above represent various important biochemical and physiological activities of body tissues. Monitoring them can provide much information regarding the tissues' vitality. In general, the more parameters that are monitored from the tissue the better and more accurate an understanding of the functional state of the tissue that may be obtained.

There are several techniques that relate to the simultaneous in-vivo measuring of multiple parameters in certain tissues, which can be used for the various pathological situations arising in modern medicine.

The prior art teaches a wide variety of apparatuses/devices which monitor various parameters reflecting the viability of the tissue, for example, in U.S. Pat. Nos. 4,703,758 and 4,945,896.

A particular drawback encountered in NADH measurements is the Haemodynamic Artifact. This refers to an artifact in which NADH fluorescence measurements in-vivo are underestimated or overestimated due to the haemoglobin present in blood circulation, which absorbs radiation at the same wavelengths as NADH, and therefore interferes with the ability of the light to reach the NADH molecules. The haemoglobin also partially absorbs the NADH fluorescence. In particular, a reduction of haemoglobin in blood circulation causes an increase in fluorescence, generating a false indication of the true oxidation reduction state of the organ. U.S. Pat. No. 4,449,535 teaches, as means to compensate for this artifact, the monitoring of the concentration of red blood cells, by illuminating at a red wavelength (805 nm) simultaneously and in the same spot as the UV radiation required for NADH excitation and measuring the variation in intensity of the reflected red radiation, as well as the fluorescence at 440-480 nm, the former being representative of the intra-tissue concentration of red blood cells. Similarly Kobayashi et al (Kobayashi et al, 1971) used ultraviolet (UV) illumination at 366 nm for NADH excitation, and red light at 720 nm for reflectance measurements. However, U.S. Pat. No. 4,449,535 has at least two major drawbacks; firstly, and as acknowledged therein, using a single optical fiber to illuminate the organ, as well as to receive emissions therefrom causes interference between the outgoing and incoming signals, and certain solutions with different degrees of effectiveness are proposed. Additionally since the same optical fiber is utilized for transmission of excitation light and for transmission of the collected light the excitation and the collection point is the same one. This imposes relatively low penetration depth as can be learned from the paper of Jakobsson and Nilsson (Jakobsson and Nilsson, 1991).

Even though both radiation wavelengths are incident on the same spot, since detection is also at the same point, effectively two different elements of tissue volume are being probed since the different radiation wavelengths penetrate the tissue to different depths. This results in measurements that are incompatible one with the other, the blood volume measurement relating to a greater depth of tissue than the NADH measurement. Therefore, the device disclosed by this reference does not enable adequate compensation of NADH to be effected using the simultaneous, though inappropriate, blood volume measurement. There is in fact no recognition of this problem, much less so any disclosure or suggestion on how to solve it. Further, there is no indication of how to measure other parameters such as blood flow rate, Fp level or blood oxygenation level using the claimed apparatus.

In two earlier patents which have a common inventor with the present invention, U.S. Pat. Nos. 5,916,171 and 5,685,313, the contents of which are incorporated herein in their entirety, a device is described that is directed to the monitoring of microcirculatory blood flow (MBF), the mitochondrial redox state (NADH fluorescence) and the microcirculatory blood volume (MBV), using a single source multi-detector electro-optical, fiber-optic probe device for monitoring various tissue characteristics to assess tissue vitality. During monitoring, the device is attached to the fore-mentioned tissue. The probe/tissue configuration enables front-face fluorometry/photometry.

Although U.S. Pat. Nos. 5,916,171 and 5,685,313 represent an improvement over the prior art, they nevertheless have some drawbacks:

(i) The oxidation level of the blood will introduce artifacts, affecting the microcirculatory blood volume (MBV) since these patents do not specify how to compensate for the oxygenation state of the blood in the tissue, i.e., the relative quantities of oxygenated blood to deoxygenated blood in the tissue. As disclosed in International Patent Application PCT/IL01/00906 filed by Applicants, this problem may be overcome by performing the NADH and blood volume measurements at an isosbestic point of the oxyhaemoglobin—deoxyhaemoglobin absorption spectrum.

(ii) There is no facility included for measurement of the oxyhaemoglobin—deoxyhaemoglobin level, i.e. the Blood Oxygenation State, which is also an important tissue viability parameter, worthy of monitoring.

(iii) In these two US patents, the same tissue volume needs to be monitored for all parameters, and the same light source and wavelength is used for the illumination needed for monitoring all three parameters. To measure both the NADH level and the blood flow rate, a relatively powerful UV laser is used having an illuminating wavelength close to the peak of the NADH excitation spectrum. Using a relatively high intensity UV laser illumination source as proposed raises safety issues, especially for long-term monitoring. An additional problem of NADH photobleaching arises since high intensity UV laser is used.

(iv) The blood flow measurements impose several requirements on the UV laser source. In particular, the UV laser needs to have a high coherence length and very low optical noise. As discussed in more depth below such lasers at these wavelengths have intrinsic properties which tend to discourage their use in such a device, and are in any case quite rare to come by in the first place.

International Patent Application PCT/IL01/00906, the contents of which are incorporated herein, filed by Applicants further addresses these problems by using two separate illumination radiation sources, one for determination of blood flow rate, and the other for determination of at least one tissue viability parameter such as NADH, blood volume and blood oxygenation state. By separating the light sources, the problem of having a single source capable of satisfactorily enabling the determination of blood flow rate as well as the other three tissue vitality parameters is avoided. This Patent application provides means for simultaneous measuring of tissue oxygenation by reflectometry rather than by measurement of the skew of the NADH or the Fp fluorescence spectra. This method of oxygenation measurement may be of limited use while the fluorescence signals are fading.

In any case, apparatuses that incorporate a laser light source are generally required to comply with relevant laser safety standards, since there is some possibility of harm to tissue from exposure to extensive radiation. The two relevant standards which deal with exposure of human tissue to laser radiation are the ANSI Z136.1-2000 "American National Standard for Safe Use of Lasers" and the IEC60825-1-1994 International Standard called "Safety of laser products".

These standards define the Maximum Permissible Exposure (MPE) values. These standards relate to laser irradiation of external tissues such as skin and eye and not of the internal organs, in contrast to typical applications of the present invention. Still they are the only known, well established references to safe irradiation values for tissues, and any laser device that is intended to perform nondestructive measurements should comply with these in the absence of a more appropriate full damage test being performed on specific tissue type with specific light irradiation.

Both the above standards permit a maximum of 1 $mW/cm^2$ irradiance at UVA spectral region (315-400 nm) for exposure time larger then 1000 sec. This requirement implies a severe limitation on the light intensity emitted by the distal tip of the fiber optic probe, particularly when shorter wavelength, higher intensity radiation is used. Both these standards address eye and skin exposure. Due to the fact that no specific standard exists for laser exposure to internal organs, these standards have been adopted herein as the applicable standards. This approach was supported by the American FDA (Premarket Notification K992529).

There has been a tendency to reduce the total amount of light sources that are incorporated in medical devices designed for tissue vitality measurements, which generally results in a simplified design, lower costs and increased reliability. Therefore this has led to the search for a special light source that may be used for as many parameters as possible, and resulted in the evolution of special expensive low noise UV light sources for Doppler measurement. Measurement of Laser Doppler at UV wavelengths raise additional safety aspects that significantly complicate the device. On the other hand, recent developments in solid state light sources enable improved design of compact and inexpensive medical devices which may be based on multiple light sources.

In PCT/IL 01/00900 to Applicant, the contents of which are incorporated herein, an apparatus is described for monitoring a plurality of tissue viability parameters of a substantially identical tissue element, in which a single illumination laser source provides illumination radiation at a wavelength such as to enable monitoring of blood flow rate and NADH or flavoprotein concentration, together with blood volume and also blood oxygenation state. In preferred embodiments, an external cavity laser diode system is used to ensure that the laser operates in single mode or at else in two or three non-competing modes, each mode comprising a relatively narrow bandwidth. A laser stabilisation control system is provided to ensure long term operation of the laser source at the desired conditions.

In the desire to avoid unnecessary complication of the device due to multiple light sources, the developers search for a single light source that would provide adequate excitation light for all parameters. This resulted in the evolution of a special expensive low noise UV light sources for Doppler measurement.

Measurement of Laser Doppler at UV wavelengths raises additional safety aspects that significantly complicate the device. However, recent developments in solid state light sources now enable embedding several light sources in a relatively simple device without imposing excess complications to the device.

In these prior art publications in which multiparametric measurements are conducted, the illuminating radiation is provided at a single location, and great care is taken that the same tissue volume, or at least the same tissue layer is the subject of the monitoring, and thus one or more detection fibers have to be strategically located in relation to the illuminating fiber to achieve this goal. In the present invention, there is no imperative need for the same tissue volume or layer to be monitored, and in fact each parameter may be monitored separately on a different part of the same organ. This is because the entire organ is affected substantially equally by the pathological condition, that is the body compensatory mechanism is affecting the organ in substantially the same way thus, the apparatuses, systems and methods used in the prior art for multiparametric monitoring according to the present invention are not necessarily suitable for the purposes of the prior art apparatuses, systems and methods.

It is an aim of the present invention to overcome the above deficiencies in the prior art.

It is another aim of the present invention to provide a multiparametric apparatus, system and method for the diagnosis of metabolic emergency state based on multiparametric monitoring.

It is another aim of the present invention to provide such a device or apparatus that conforms to the relevant laser safety standards.

It is another aim of the present invention to provide such a device or apparatus that is of a convenient size, weight and power consumption such as to enable the same to be portable and/or installable within regular operating theaters.

Other purposes and advantages of the invention will appear as the description proceeds.

SUMMARY OF THE INVENTION

The present invention relates to an apparatus for monitoring in a non-vital organ at least one tissue viability parameter including at least one of NADH and Flavoprotein (Fp) concentration corresponding to said organ being monitored, for the early diagnosis of body metabolic emergency state, wherein the state of said at least one tissue viability parameter of said non-vital organ is indicative of degree of said body metabolic emergency state, the apparatus comprising:

illumination means for illuminating a first part of said organ with at least one illuminating radiation via at least one illumination location with respect to said tissue;

radiation receiving means for receiving a radiation from a second part of said organ as a result of an interaction between said illuminating radiation and said tissue;

correlating means adapted for correlating at least a part of said received radiation to said at least one tissue viability parameter; and indicating means for indicating the degree of body metabolic emergency state based on said at least one tissue viability parameter.

The at least one tissue viability parameter may be NADH concentration, wherein said radiation received by said radiation receiving means comprises an NADH fluorescence emitted by the tissue in response to illumination thereof by said illuminating radiation, said at least one tissue viability parameter being provided by the intensity of said NADH fluorescence. Additionally or alternatively, the said at least one tissue viability parameter is Fp concentration, wherein said radiation received by said radiation receiving means comprises an Fp fluorescence emitted by the tissue in response to illumination thereof by said illuminating radiation, said at least one tissue viability parameter being provided by the intensity of said Fp fluorescence The correlating means may be further adapted for correlating at least a part of said received radiation to at least one other tissue viability parameter including at least one of blood flow rate, blood volume and oxy-deoxy state tissue viability parameter. The illuminating means may comprise a plurality of illuminating radiation wavelengths corresponding to the number of different tissue viability parameters being monitored. The illuminating means may comprise an illuminating radiation of wavelength in the range of between about 315 nm to about 400 nm, and preferably about 366 nm, about 375 nm, about 380 nm or about 390 nm, for monitoring NADH tissue viability parameter. The illumination means may also comprise a suitable LED for providing an illuminating radiation of wavelength in the range of between about 315 nm to about 400 nm, and preferably about 366 nm, about 375 nm, about 380 nm or about 390 nm, for monitoring NADH tissue viability parameter. The illuminating means may also comprise an illuminating radiation of wavelength between about 430 nm and about 470 nm for monitoring flavoprotein concentration tissue viability parameter. The illuminating means may also comprise two illuminating radiations, one at an isosbestic wavelength, and the other at a non-isosbestic wavelength, for monitoring blood oxygenation tissue viability parameter, and the wavelengths thereof may be about 525 nm or about 585 nm, and about 430 nm or 577 nm, respectively. The illuminating means may also comprise an illuminating radiation of wavelength between about 550 nm and 800 nm, and preferably about 655 nm or 785 nm, for monitoring blood flow rate tissue viability parameter.

Typically, the illumination location is provided by at least one excitation optical fiber having a free end capable of being brought into registry with said first part of said tissue. The radiation receiving means comprises at least one suitable receiving optical fiber having a free end capable of being brought into registry with said second part of said tissue. The at least one excitation optical fiber and said at least one receiving optical fiber are preferably housed in a suitable probe head. The at least one excitation fiber may comprise a suitable first connector at an end thereof opposed to said free end thereof, said first connector capable of selectively coupling and decoupling said excitation fiber from the rest of the said apparatus. At least one collection fiber may comprise a suitable second connector at an end thereof opposed to said free end thereof, said second connector capable of selectively coupling and decoupling said collection fiber from the rest of the said apparatus.

Optionally, the probe may be disposable and/or sterilisable.

Typically, the blood flow rate tissue viability parameter is provided by applying a laser Doppler flowmetry technique to said radiation received by said radiation receiving means.

The apparatus also comprises first detection means for detecting said received radiation received by said radiation receiving means.

The at least one tissue viability parameter may further comprise blood volume within said organ, and said corresponding radiation received by said radiation receiving means comprises a reflectance from the organ in response to illumination thereof by said illuminating radiation, the said at least one tissue viability parameter being provided by the intensity of said reflectance.

The at least one tissue viability parameter may further comprise blood volume within said organ, and said corresponding radiation received by said radiation receiving means comprises a reflectance from the organ in response to illumination thereof by said illuminating radiation, the said at least one tissue viability parameter being provided by the intensity of said reflectance, wherein said illumination radiation is at an isosbestic wavelength.

The at least one tissue viability parameter further may comprise blood volume within said organ, and said corresponding radiation received by said radiation receiving means comprises two separate reflectance from the organ in response to illumination thereof by two different illuminating radiations, the said at least one tissue viability parameter being provided by the intensity of each said reflectance, wherein each said illuminating radiation is at a different isosbestic wavelength.

In one embodiment, the probe head is adapted for optical measurement in organs comprising tubular vessels. In particular, the probe head may be adapted for optical measurement in organs comprising tubular vessels, including the esophagus, urethra, blood vessels, the stomach and bladder. Optionally, the probe is incorporated in a suitable urethral catheter including a Folley catheter.

In another embodiment, the probe head is adapted for optical measurement on organs comprising skin, and the probe head may be attached to the skin via a suitable gel, or via a suitable adhesive.

In yet another embodiment, the probe head is adapted for fetal distress monitoring.

In another embodiment, the probe head is adapted for soft tissue insertion.

In said apparatus, the first part and said second part may be at the same location of said organ, or, the first part of said organ is different from said second part of said organ.

The body metabolic emergency state being diagnosed is typically sepsis.

The present invention also relates to a system for selectively monitoring in a plurality of organs at least one tissue viability parameter including at least one of NADH and Flavoprotein (Fp) concentration corresponding to each said organ being monitored, for the early diagnosis of body metabolic emergency state, said system comprising a plurality of monitoring probes, each said probe comprising an apparatus as defined herein. The different organs may be different organs within the same organism, or different organs within different organisms, or may include donor organs.

The present invention also relates to a system for selectively monitoring in a plurality of locations in the same organ at least one tissue viability parameter including at least one of NADH and Flavoprotein (Fp) concentration corresponding to each said location of the organ being monitored, for the early diagnosis of body metabolic emergency state, said system comprising a plurality of monitoring probes, each said probe comprising an apparatus as defined herein.

The present invention also relates to a method for diagnosing the degree of body metabolic emergency state, comprising:—
(a) choosing a non-vital organ with respect to the said metabolic emergency state;
b) monitoring in said non-vital organ at least one tissue viability parameter including at least one of NADH and Flavoprotein (Fp) concentration; and
(c) determining the degree of body metabolic emergency state based on said at least one tissue viability parameter monitored in (b).

In step (c), said determination is preferably correlated to the direction of change in the value of said at least one tissue viability parameter. Preferably, in step (c) said degree of body metabolic emergency state is correlated to the amplitude and duration of a change in said value of said at least one tissue viability parameter.

Optionally, the at least one tissue viability parameter is NADH concentration, and an increase in the value thereof is indicative of the presence of a said body metabolic emergency state.

Optionally or additionally, the at least one tissue viability parameter is Flavoprotein concentration, and a reduction in the value thereof is indicative of the presence of a said body metabolic emergency state.

Optionally or additionally, the at least one tissue viability parameter is Blood flow rate, and a reduction in the value thereof is indicative of the presence of a said body metabolic emergency state.

Optionally or additionally, the at least one tissue viability parameter is blood volume, and a reduction in the value thereof is indicative of the presence of a said body metabolic emergency state.

Optionally or additionally, the at least one tissue viability parameter is blood oxygenation level, and a reduction in the value thereof is indicative of the presence of a said body metabolic emergency state.

Typically, the non-vital organ is an organ chosen from among the skin, muscles, gastrointestinal tract and urogenital system.

Typically the body metabolic emergency state includes any one of sepsis, respiratory distress syndrome, hypoxemia, hypotension, dysoxia and cardiac arrest.

Typically, the body metabolic emergency state arises from at least one clinical situation including those that develop in a respiratory ICU, Neurosurgical ICU, delivery room both for a mother and her neonate, neonatal ICU, cardiac surgery operative room as well as post-operative period thereof, neuro surgery operative as well as post-operative period thereof, organ transplantation operative as well as post-operative period thereof, elderly and critical ill clinical situations. The method may also be used in situations wherein the body metabolic emergency state arises in patients hospitalized in various clinical wards.

BRIEF DESCRIPTION OF THE DRAWINGS

FIG. 18 illustrates schematically the main components of the probe of the present invention.

FIG. 19 illustrates, in transverse cross-sectional view, the main components of a first embodiment of the probe of the present invention.

FIG. 20(a) and FIG. 20(b) illustrate, in transverse cross-sectional view and perspective view, respectively, the main components of a second embodiment of the probe of the present invention.

FIG. 21(a) and FIG. 21(b) illustrate, in transverse cross-sectional view and perspective view, respectively, the main components of a third embodiment of the probe of the present invention.

FIG. 22(a) and FIG. 22(b) illustrate, in transverse cross-sectional view and perspective view, respectively, the main components of a fourth embodiment of the probe of the present invention.

DETAILED DESCRIPTION OF PREFERRED EMBODIMENTS

The present invention is defined by the claims, the contents of which are to be read as included within the disclosure of the specification, and will now be described by way of example with reference to the accompanying figures.

In the description to follow, the following illustrative apparatuses and methods are described, it being understood that the invention is not limited to any particular form thereof, and the following description being provided only for the purposes of illustration.

The present invention is directed to an apparatus for monitoring at least one tissue viability parameter chosen from NADH and Fp concentration corresponding to the non-vital organ being monitored, for the early diagnosis of body metabolic emergency state that may develop in many acute or chronic clinical conditions. Preferably, the apparatus is adapted for the simultaneous monitoring of such a parameter and the other tissue viability parameters including at least one of, and preferably more than one of, and most preferably all of, the set of parameters comprising blood flow rate, blood volume, tissue blood oxygenation state and either at least Fp concentration and at least NADH concentration respectively. Multiple light radiation sources provide appropriate illumination at each particular excitation wavelength that are optimally used for monitoring these parameters, as will be described in detail hereinbelow.

Thus, the present invention is directed to an apparatus for monitoring in a non-vital organ at least one tissue viability parameter including at least one of NADH and Flavoprotein (Fp) concentration corresponding to said organ being monitored, for the early diagnosis of body metabolic emergency state, wherein the state of said at least one tissue viability parameter of said non-vital organ is indicative of degree of said body metabolic emergency state, the apparatus comprising:— illumination means for illuminating a first part of said organ with at least one illuminating radiation via at least one illumination location with respect to said tissue;

radiation receiving means for receiving a radiation from a second part of said organ as a result of an interaction between said illuminating radiation and said tissue;

correlating means adapted for correlating at least a part of said received radiation to said at least one tissue viability parameter; and indicating means for indicating the degree of body metabolic emergency state based on said at least one tissue viability parameter.

Body Emergency Metabolic State (BEMS) is understood herein to refer to the physiological or initial stage of pathophysiological conditions leading to changes in the distribution of blood flow to various organs in the patient, and in which preference is given to the most vital organs in the body, namely the brain, heart and adrenal gland. As a result, the non vital organs such as the skin, muscle, G-I tract and the urogenital system, will enter into a hypoperfusion state.

Figure 1:
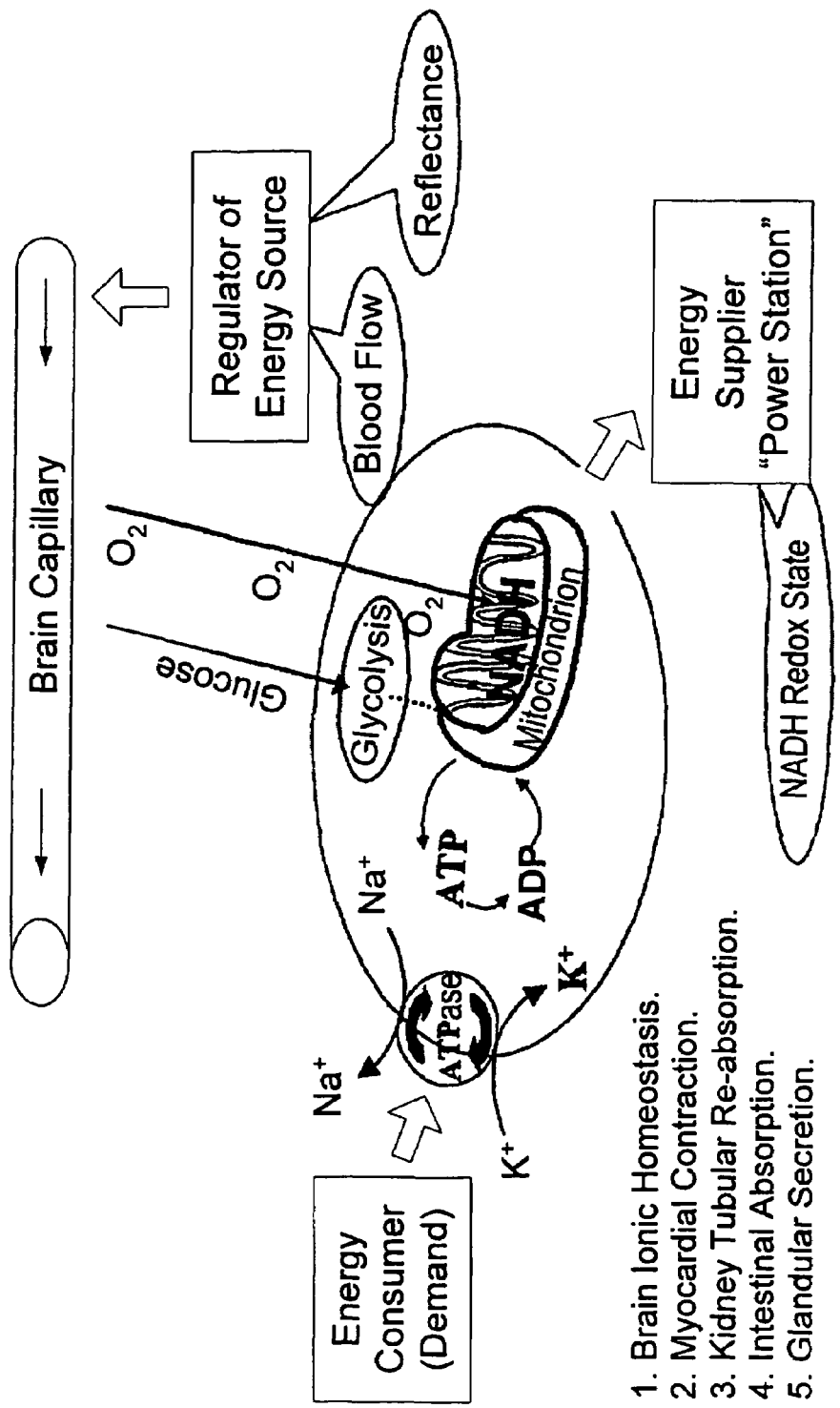
FIG. 1 illustrates the interrelation between energy demand, energy supply and regulation of the blood flow to a normal tissue. The list (1-5) in the left side of the figure demonstrates various energy demand processes in typical tissues.
Figure 2:
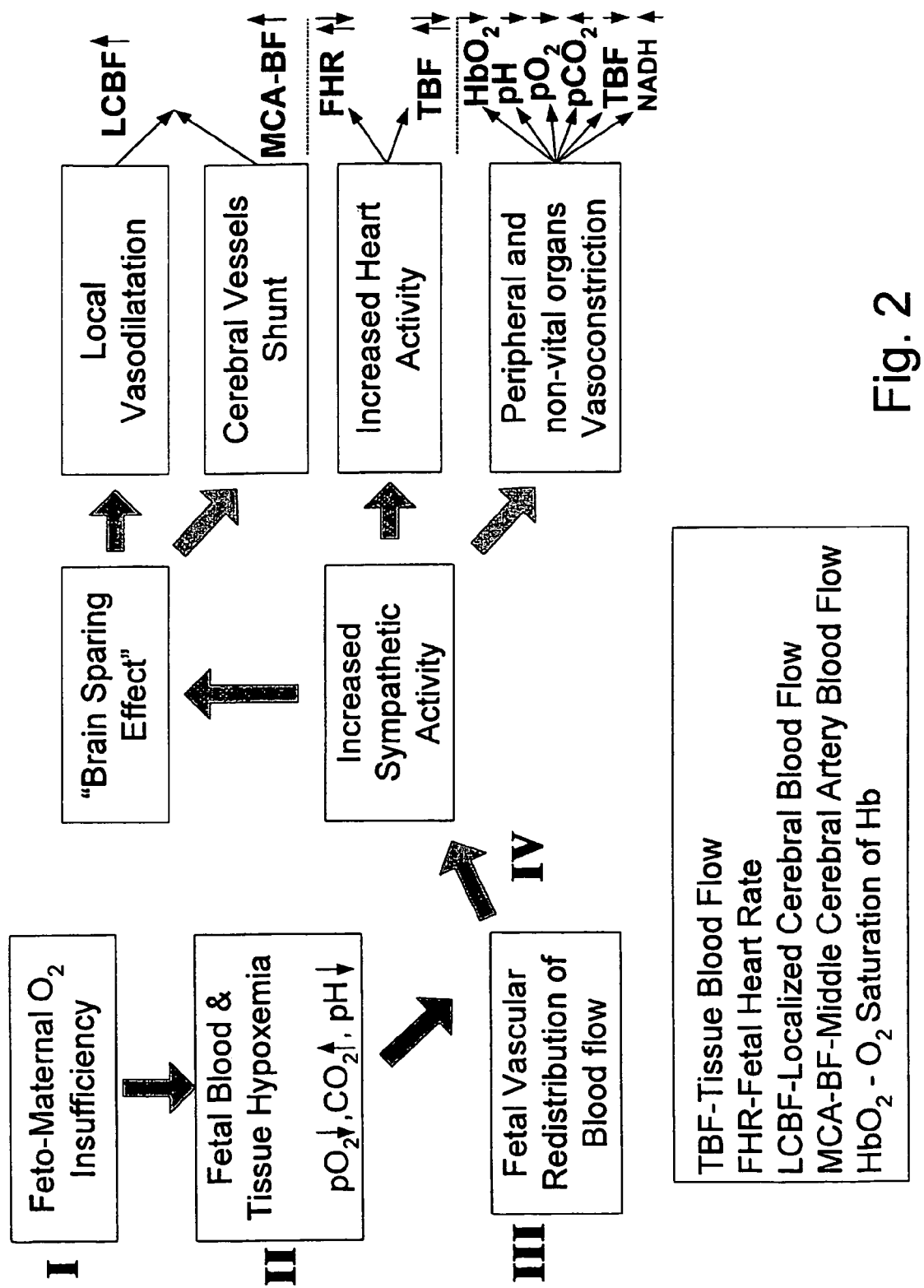
FIG. 2 schematically illustrates the sequence of events and responses taking place during fetal distress, during delivery. (TBF—Tissue Blood Flow; FHR—Fetal Heart Rate; LCBF—Localized Cerebral Blood Flow; MCA-BF—Middle Cerebral Artery Blood Flow; HbO2-O2 Saturation of Hb).
Figure 3:
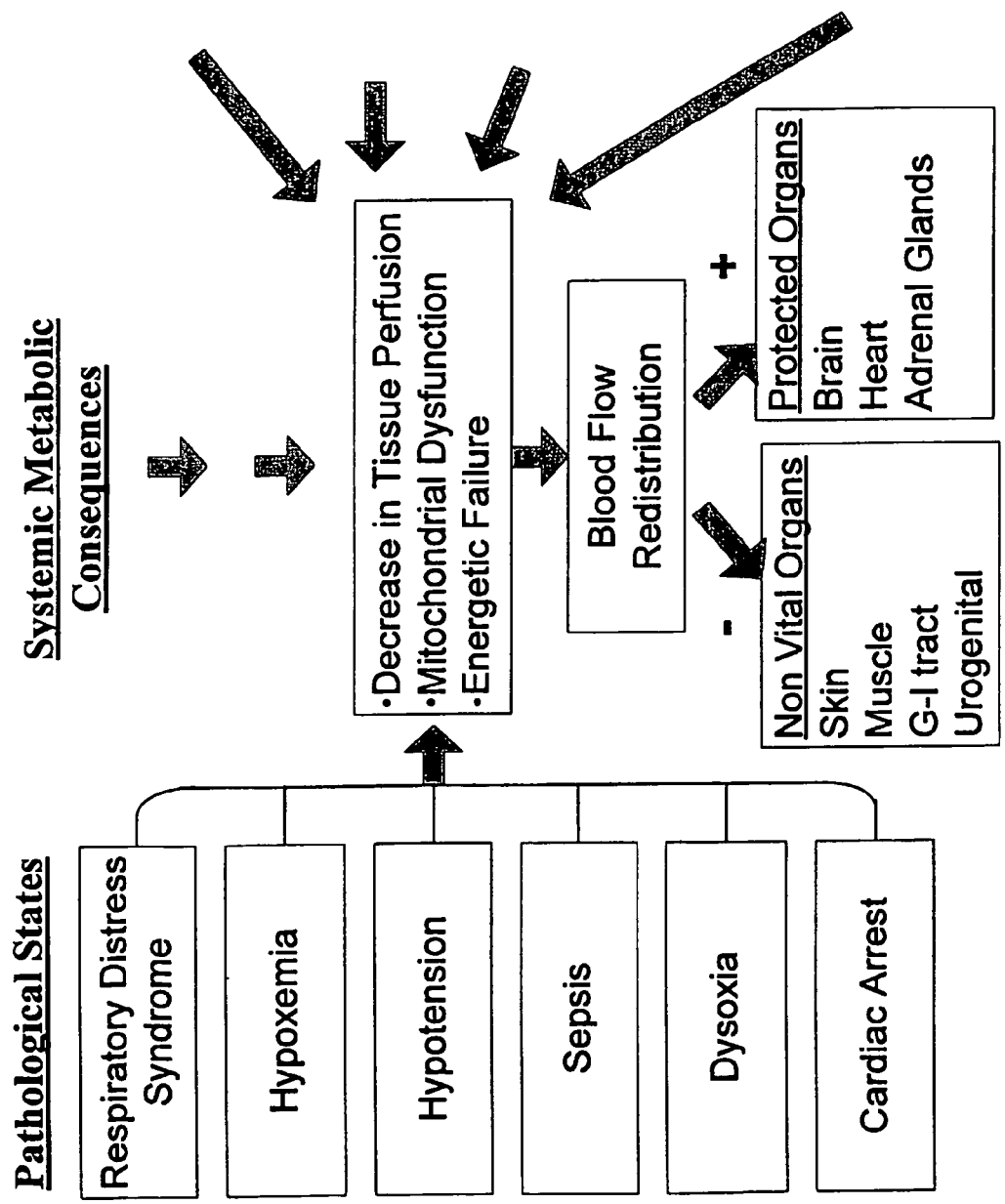
FIG. 3 shows a schematic presentation of various pathological states (left side of figure) developed under various clinical situations (right side of figure). The systemic metabolic consequences and the responses of the body to it are shown in the center of the figure. An increase in blood flow (+) will noticed in the protected organs and the decrease (−) in blood flow to the non vital organs will be proportional to the severity of the situation.
Figure 3:
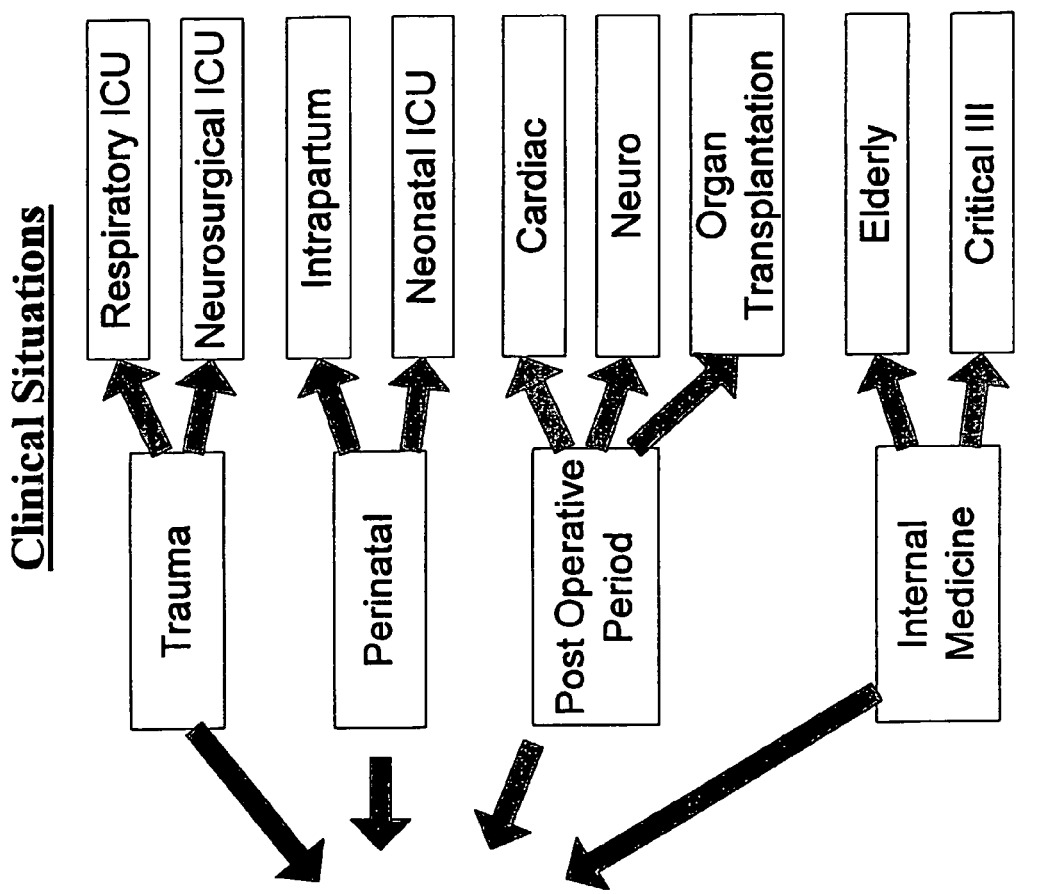
Figure 4:
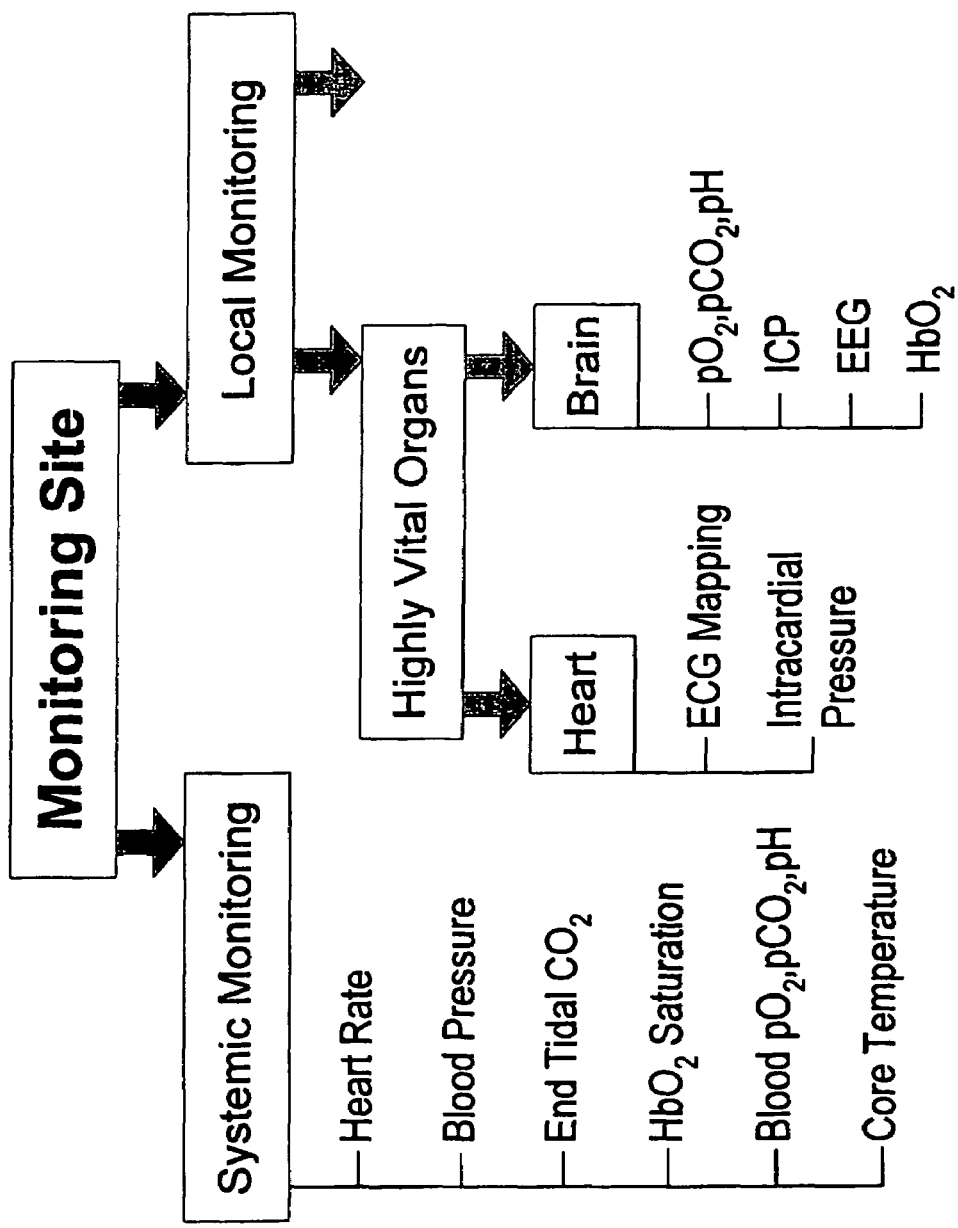
FIG. 4 shows a schematic presentation of the classification of monitoring approaches and type of parameters.
Figure 4:
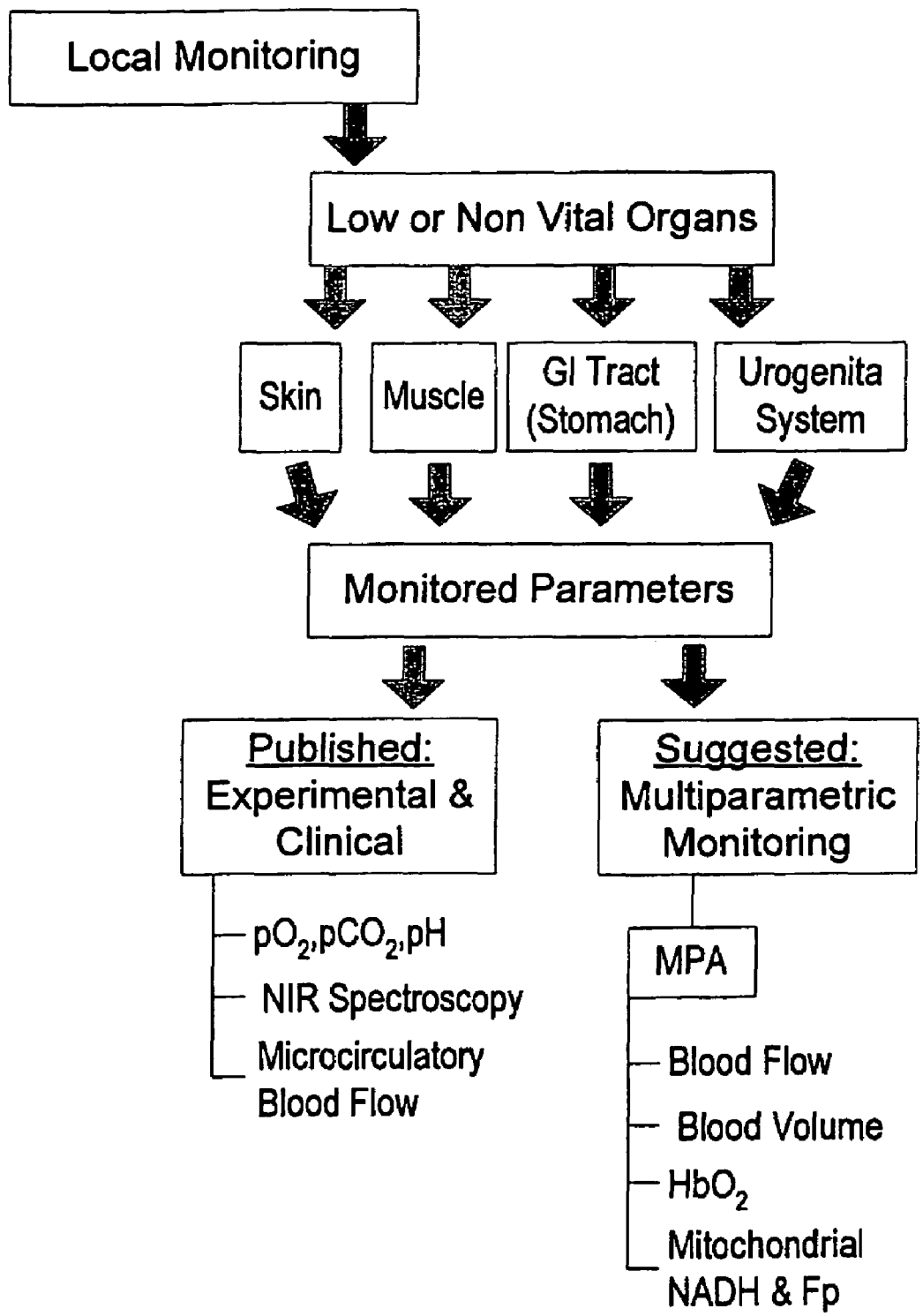
Figure 5:
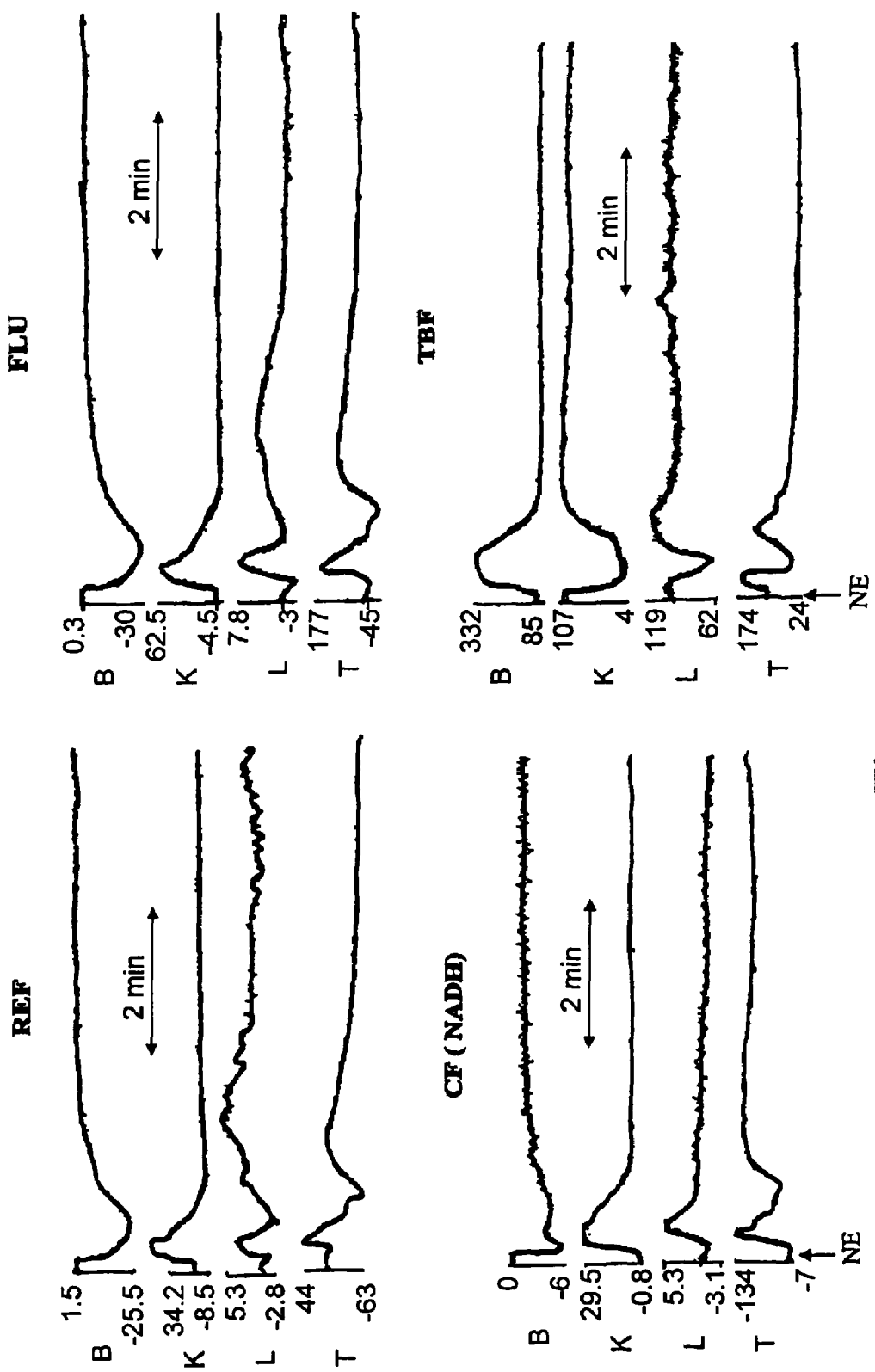
FIG. 5 shows the Hemodynamic and Metabolic responses of 4 different organs to norepinephrine injection, intravenuosly.
Figure 6:
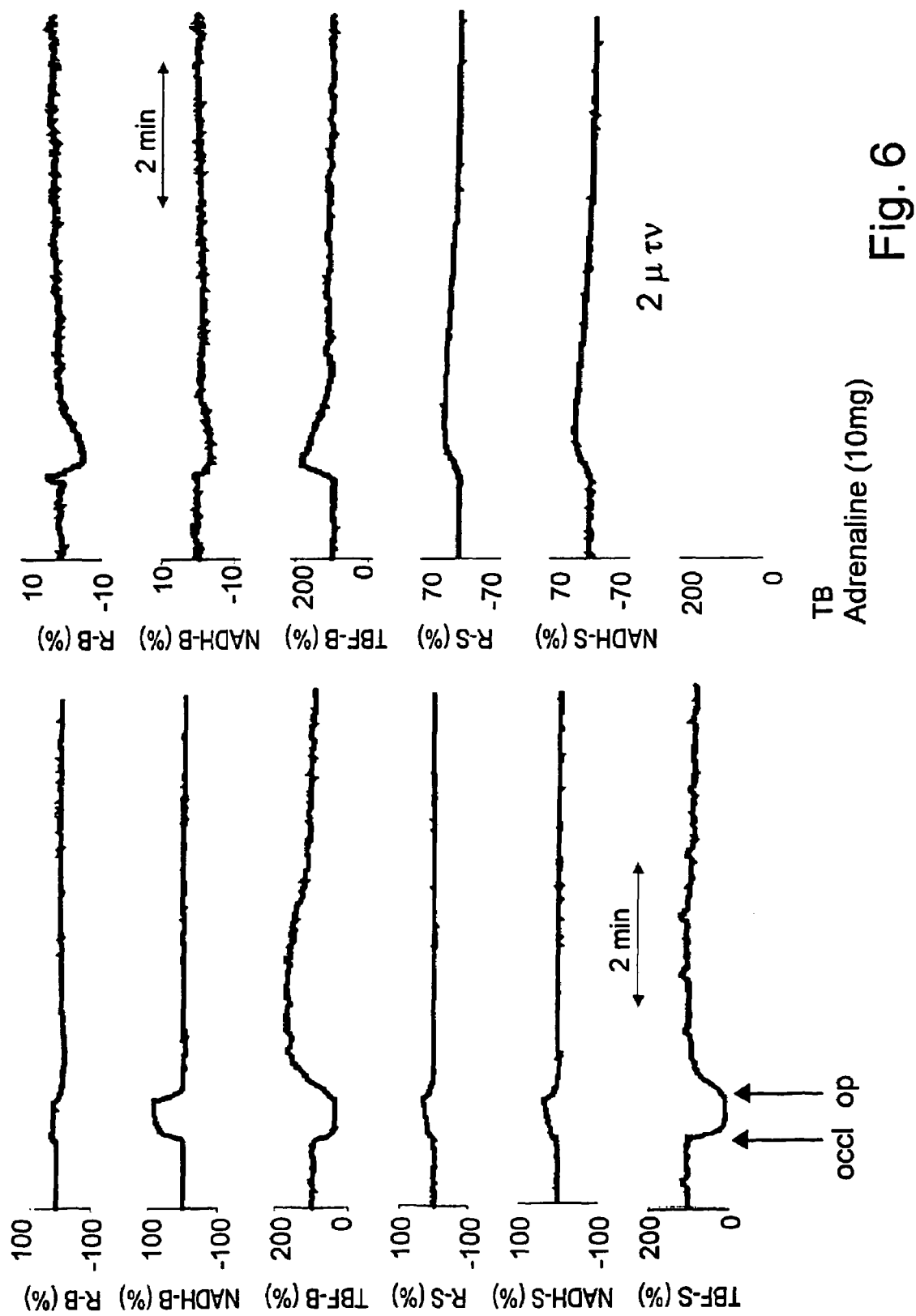
FIG. 6 shows a comparison of the hemodynamic and metabolic responses to ischemia and adrenaline injection both in the rat brain (B) and skin (S) in the scalp area.
Figure 7:
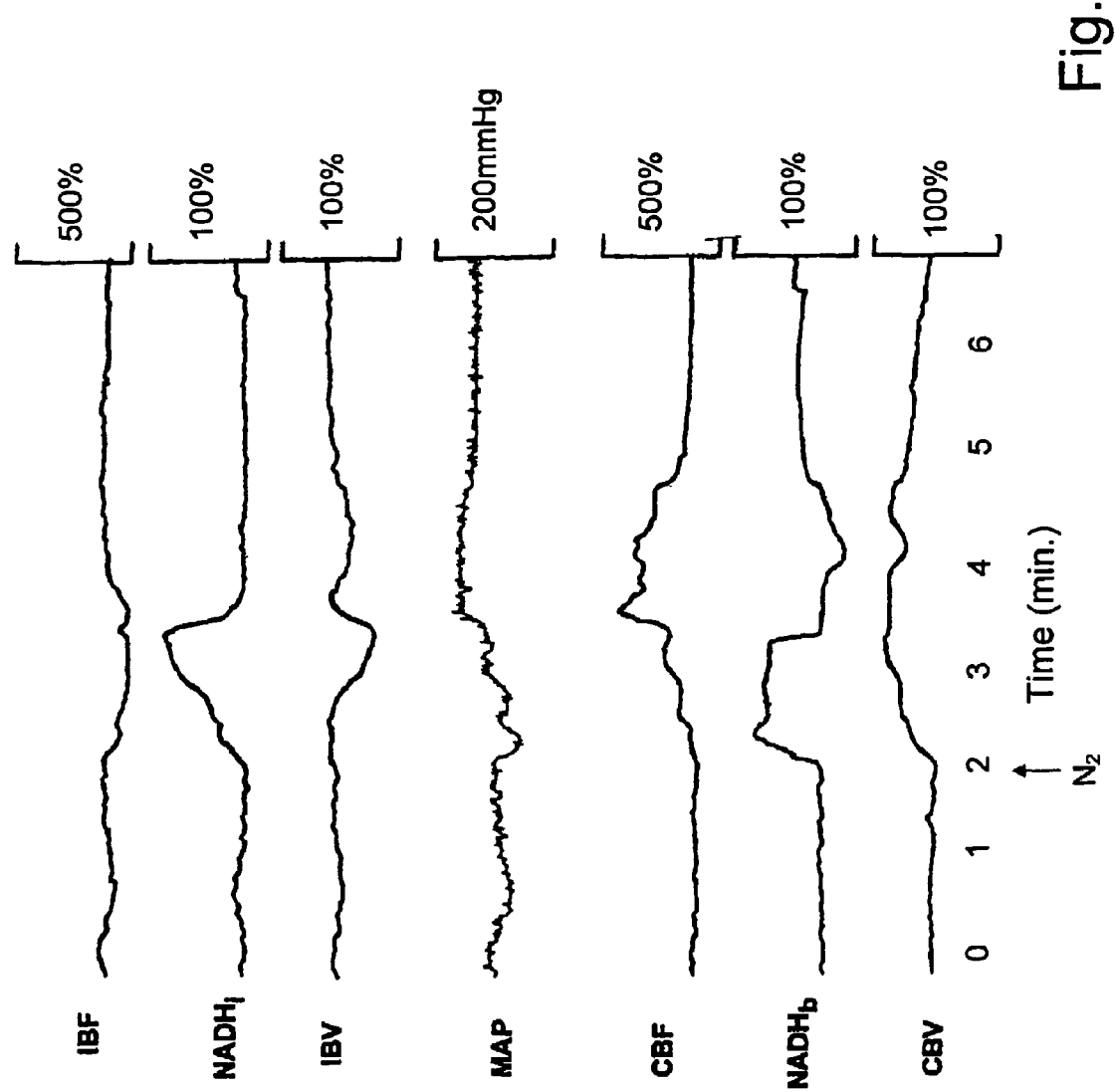
FIG. 7 illustrates the effect of anoxia (N2) on systemic blood pressure (MAP) as well as hemodynamic and metabolic activities in the serosal side of the small intestine (upper 3 channels) and brain cortex (lower 3 channels). IBF, CBF—intestinal and cerebral blood flow NADHI, NADHB—intestinal and cerebral mitochondrial NADH. IBV, CBV—intestinal and cerebral blood volume measured by tissue reflectance.
Figure 8:
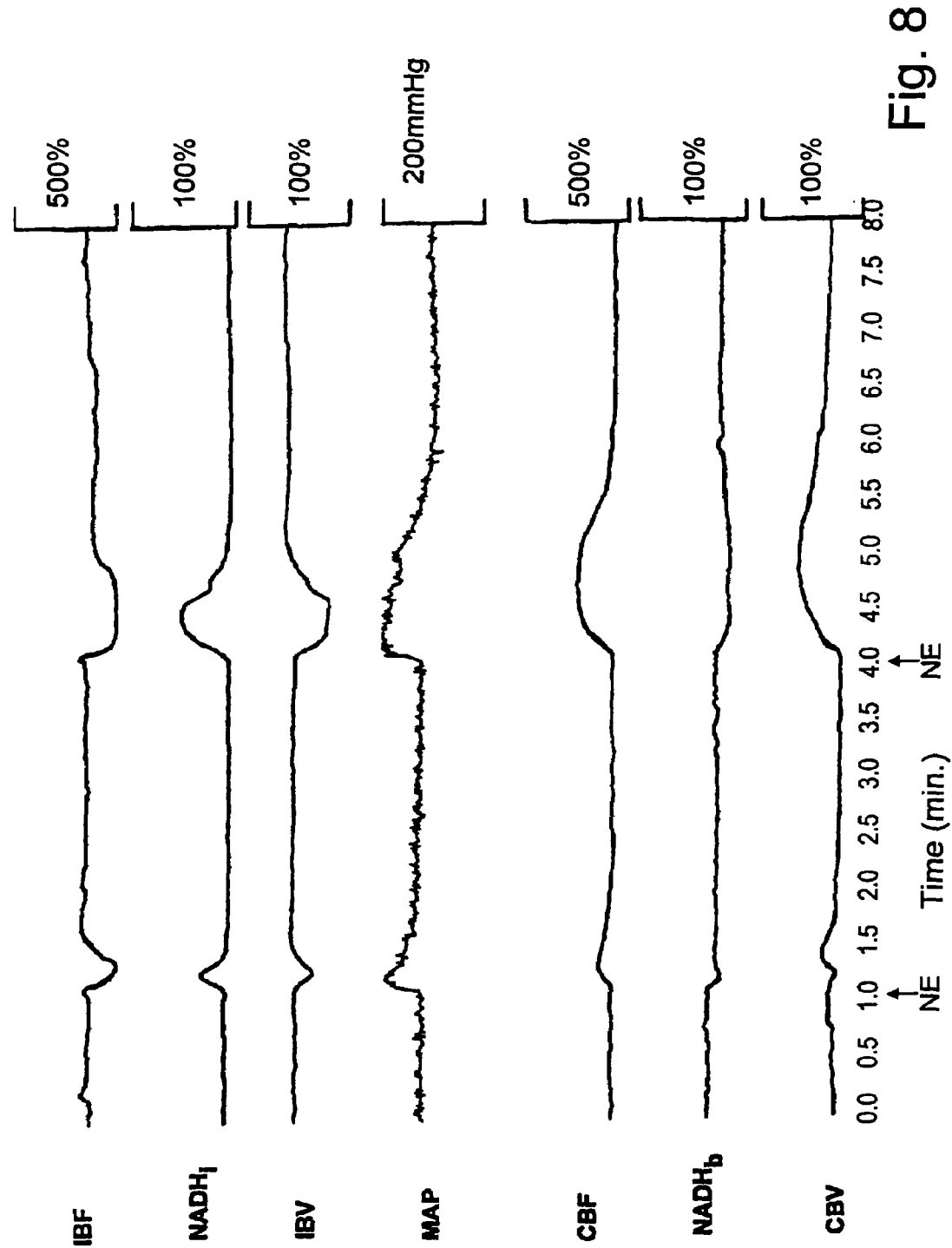
FIG. 8 illustrates the effects of noradrenaline IV injection (NE) on mean arterial pressure, small intestine (upper 3 traces) and brain (lower 3 traces) blood flow, volume and mitochondrial NADH redox state. Two levels on NE were injected to the same rat. The intestinal probe was located on the serosal side of the ileum. All abbreviations are as in FIG. 7.
Figure 9:
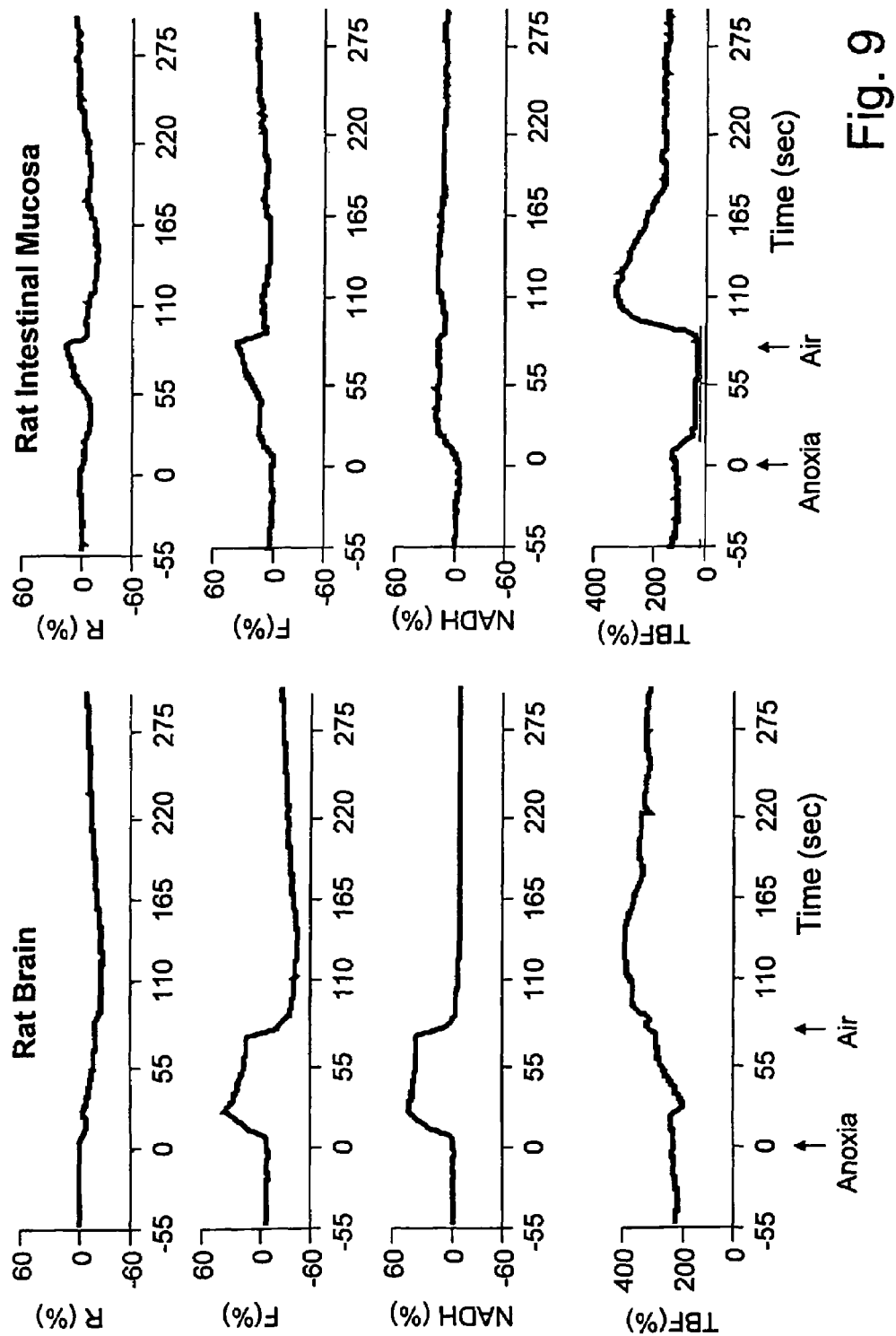
FIG. 9 illustrates the effects of anoxia on rat brain and intestine blood flow, tissue reflectance and mitochondrial NADH redox state monitored simultaneously. R, F, NADH: reflectance, fluorescence and corrected NADH fluorescence. TBF: Tissue blood flow.
Figure 10:
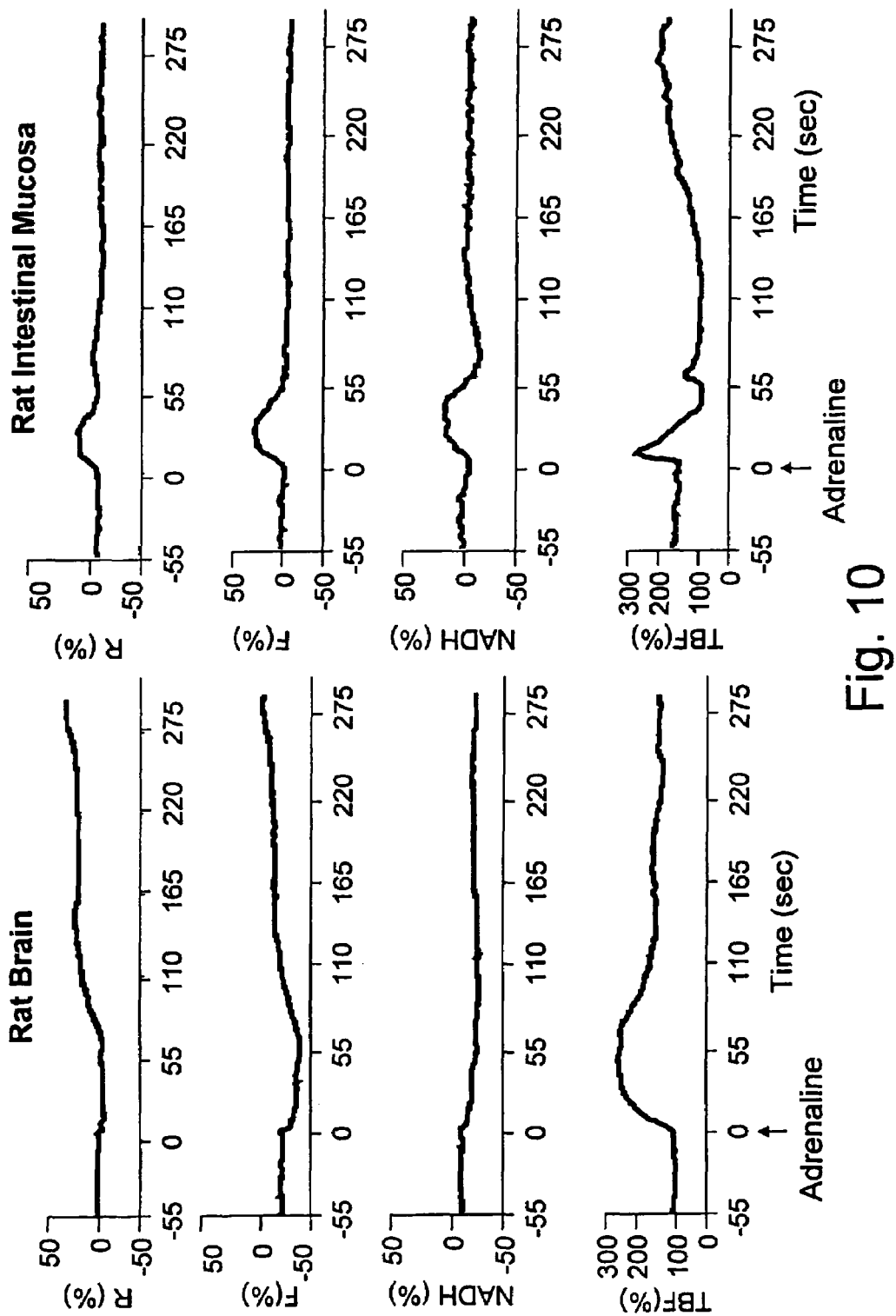
FIG. 10 illustrates the responses of the rat brain and small intestine to IV injection of adrenaline measured simultaneously. Abbreviations are as in FIG. 9.

According to the invention, the apparatus comprises indicating means, which comprises any suitable system by which the BEMS may be determined in real time. Thus, such a system is operatively connected to a multiparametric monitoring probes, particular as in the present invention that measure in real time various parameters shown in FIG. 4. In addition the apparatus includes a computerised unit for data acquisition and a special software for the analysis of the results in real time.

In a patient subjected to BEMS, the rate or intensity of blood flow redistribution will be dependent upon the insult that led to the development of the emergency state. The indicating means enables the determination of a scale or degree of emergency state according to the relative changes recorded by one or the various probes connected to the patient's non vital organ. The software will take into consideration two dynamic parameters:

1. The amplitude of the change.
2. The time duration of the change.

These two criteria will be tested in each one of the monitored parameters. The relationship between the amplitude and the duration of a change is not linear but rather asymptotic. This means that if the amplitude of the change is below a certain threshold level, then even a very long duration associated with it will not be effective. The same is true if the duration of the change is below the minimal threshold, then even a very high amplitude change will not be effective.

The mathematical model to be used in the software will define and use critical levels of each of the monitored parameters to be considered and weighted accordingly. The output of such an indicating mean will be a representative number ranging from 0-100, say. Normal tissue will have a very low value in this scale, and under the development of an emergency state the higher the number or index the more the severe is the situation is for the patient.

It is possible that a BEMS index will be created by various combinations of changes in the individual parameters. It is important to note that the change in the blood flow or HbO2 recorded in a non-vital organ represents the vascular compartment of the tissue while the NADH and the Fp signal is originating from the intracellular space—the mitochondrion which is under different kind of regulating mechanisms.

Figure 11:
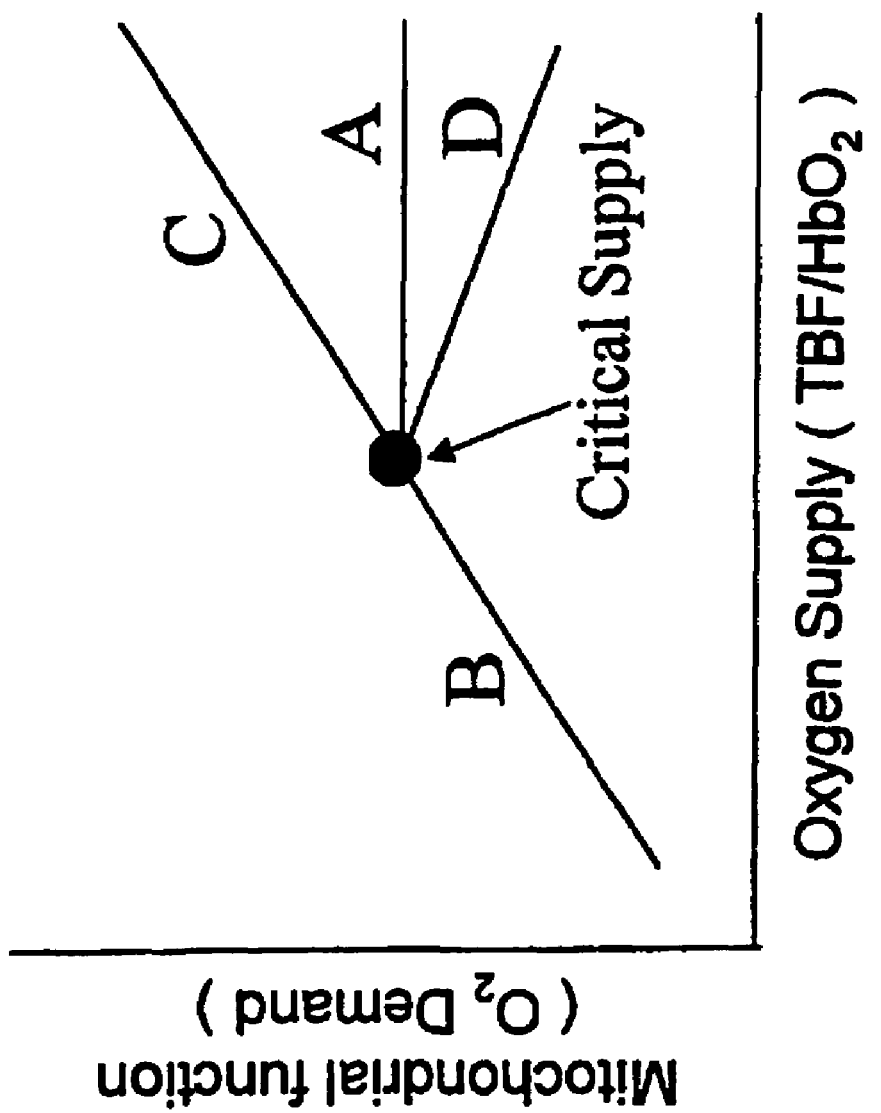
FIG. 11 illustrates schematically the relationship between O2 supply and demand under various situations.
Figure 12:
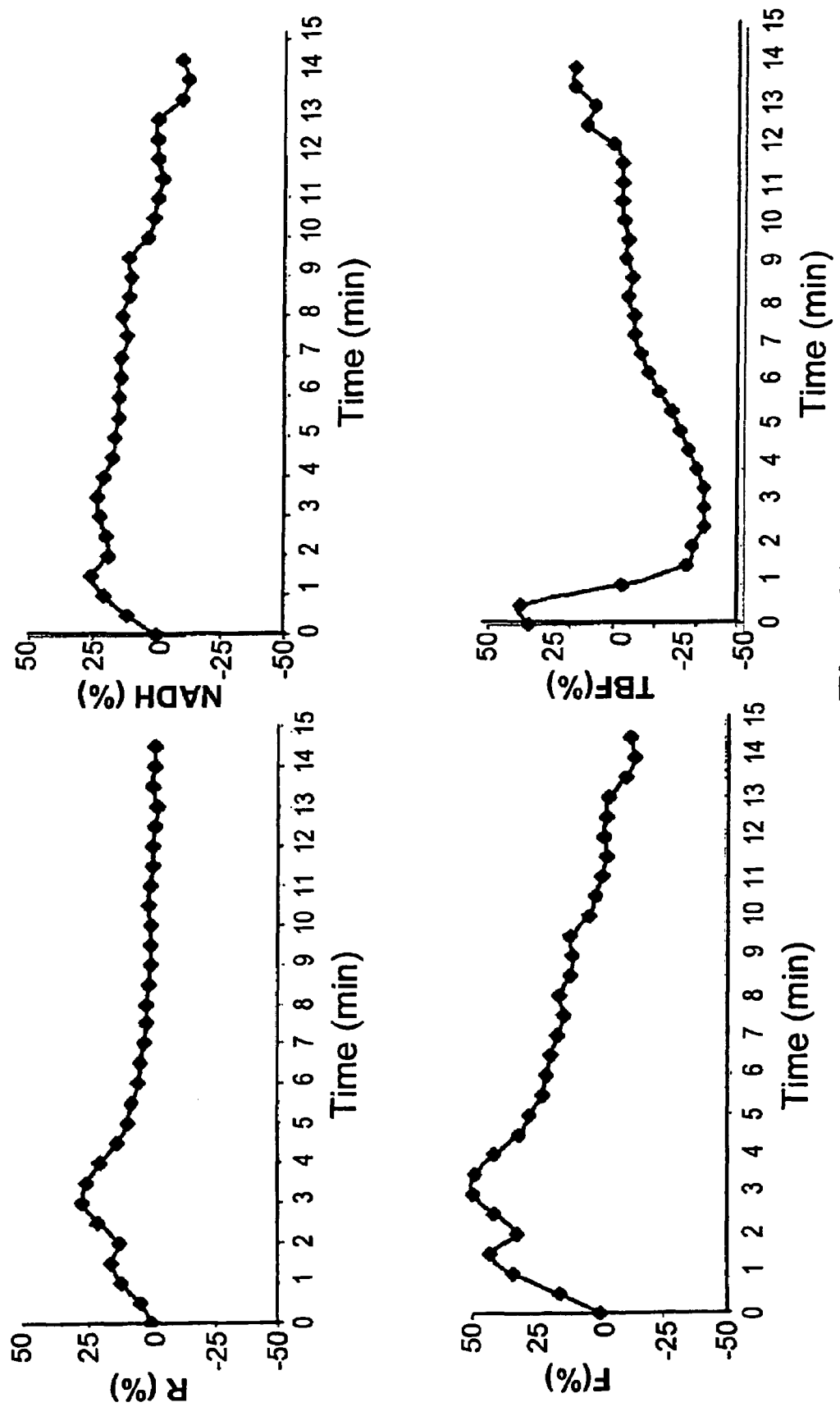
FIG. 12 illustrates the responses of rat's urethra to intravenous Adrenaline injection: TBF—Tissue Blood Flow; R, F—Reflectance and Fluorescence; NADH—Corrected NADH Fluorescence.

When such a BEMS index value increases above a certain level, this will suggest that a more severe situation developed. Various combinations of changes are shown in FIG. 11. It is clear that the change in blood flow alone is not sensitive enough to determine BEMS and only the intracellular consequences measured from the mitochondria will provide reliable picture of the situation.

The correlating means may be hardware or software based, though preferably they form part of the software comprised in the computing means or personal computer (5), described herebelow, and enables the data signals received from the probe to be translated into tissue vitality values.

Thus the NADH and/or Fp concentration measurement is conducted concurrently with the monitoring of the other tissue viability parameters, providing simplicity in terms of configuration and design of the monitoring apparatus, as well as in the method of use, as will be evident from the following description.

Figure 14:
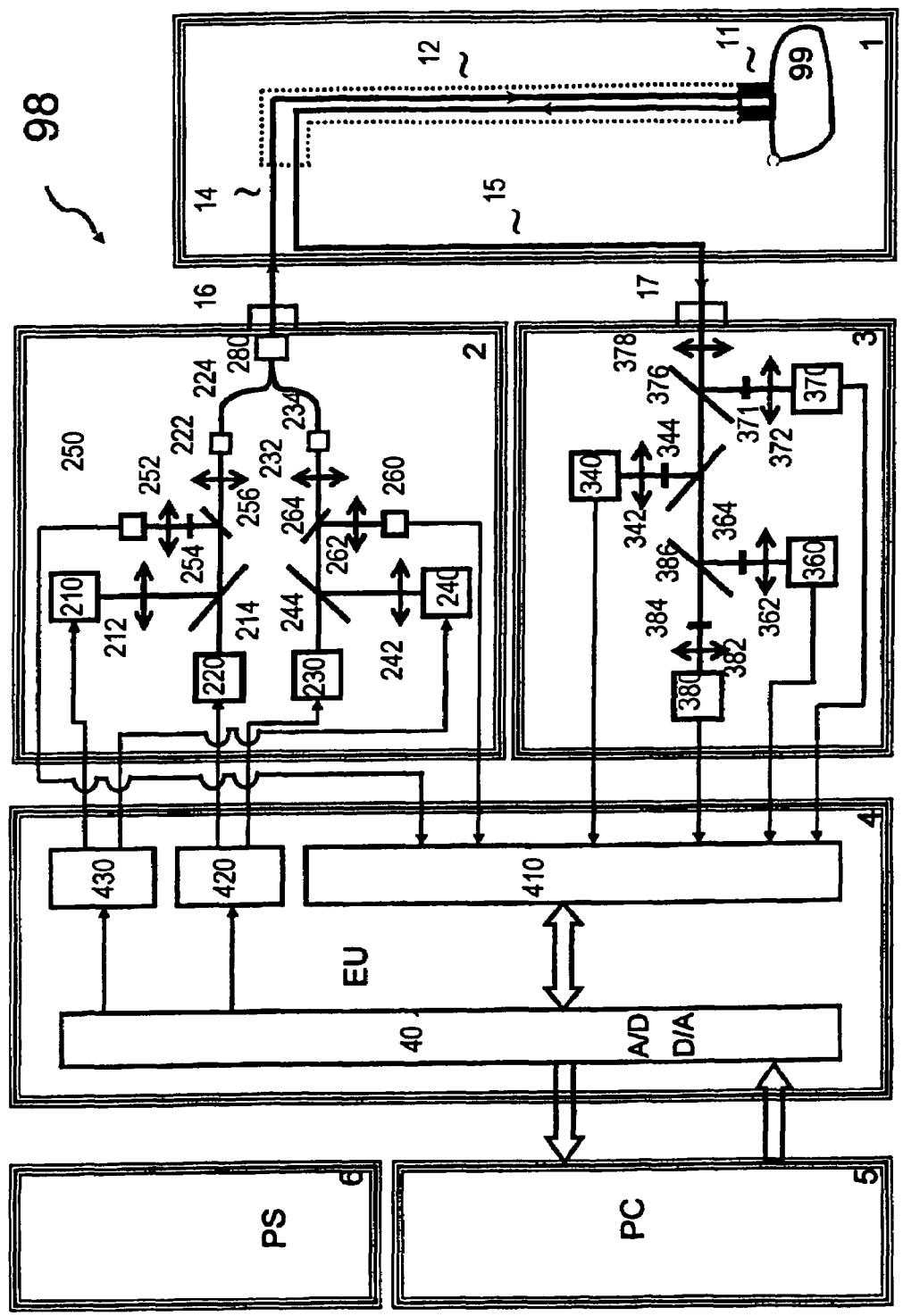
FIG. 14 illustrates schematically the main components of the first embodiment of the apparatus of the present invention.

Referring in particular to FIG. 14, in the preferred embodiment of the present invention the apparatus, generally designated (98), comprises several sub units, including Light Source Unit (LSU) (2), a Fiber Optic Probe (1), Detector Unit (DTU) (3), Electronics Unit (EU) (4), Personal Computer (PC) (5) and Power Supply (PS) (6). The Light Source Unit (LSU) (2) comprises multiple solid state emitters that provide the illumination source for measurement of the desired parameters. The Light Source Unit (LSU) (2) is optically coupled to a Fiber Optic Probe (1), which transmits the illumination light to the tissue, collects the light from the tissue and transmits it back to the Detector Unit (DTU) (3). The DTU (3) comprises several photodetectors that convert light signals to electrical signals. The electrical signals from the DTU (3) are transferred to the Electronics Unit (EU) (4) for processing and conversion to digital data that is then transferred to the dedicated microprocessor computing means, typically a Personal Computer (PC) (5). The apparatus (98) also incorporate appropriate Power Supply (PS) (6) that supply the electronic circuits of all sub units with appropriate electric current.

In this embodiment, the LSU (2) preferably comprises of four separate light sources. Each source is utilized for generation of light of specific wavelength appropriate for the measurement of one or more physiological parameters.

The first light source (210) is utilized for tissue blood oxygenation measurements, and may comprise a Light Emitting Diode (LED) that emits green light that peeks at a wavelength of around 525 nm. The BP280CWAG6K-3.5 Vf-050T LED from Ledtronics Inc. Torrance Calif. can be used for this purpose. This kind of LED has high luminous intensity of about 10000 mcd. Similar LEDs are readily available from several additional produces. The light from this LED is collimated with the lens (212) towards the dichroic mirror (214). This dichroic mirror reflects light at wavelengths shorter than 600 nm and transmits light at higher wavelengths. This dichroic mirror enables combining of the green light from the LED with the red light from the second light source or red Laser Diode (220). Alternatively, a wavelength of about 585 nm may be used for this light source.

The red laser diode (220) is utilized for laser Doppler measurements. This laser diode (220) can be any single longitudinal mode laser diode such as LD1350 from Power Technology Inc. Mabelvale, Ark., for example, which emits in continuous wave mode (CW) at 655 nm. The laser diode also preferably operates at single longitudinal mode. Typically a red free-running single longitudinal mode laser diode source emits laser radiation over a band of 10 to 15 MHz. This bandwidth is narrow enough for laser Doppler blood flowmetry. Many similar single mode laser diodes with various red wavelengths are available at the market. The laser diode is preferably incorporated in appropriate laser head that preferable also includes a Peltier thermoelectric cooler with closed loop feedback temperature controller. This temperature control can improve wavelength stability of the laser diode and also ensure noiseless output for long time periods. Any way general red single mode laser diode is good enough to serve as laser Doppler light source.

The light from the LED (210) and from LD (220) is combined by the dichroic mirror (214) and passes toward the fiber optic connector (224). In order to insert the light to the optical fiber the focusing lens (222) is used. In order to monitor the excitation intensity of the green light source small part of the green light is deflected towards the photodiode (250) by the dichroic beam splitter (256). The split light component then passes through additional optical filter (254) in order to eliminate the remaining small intensity at the red and focused on the photodiode by the lens (252). The monitoring of the intensity of the red light is not critical, since the signal-processing algorithm of the laser Doppler measurement normalizes the detected AC signal, that is correlated to the Doppler, with the total light intensity of the DC signal. Therefore the exact absolute value of the red laser excitation intensity is not absolutely necessary for the Doppler measurements. In any case, this intensity can be measured from the LD internal photodiode that is incorporated in each LD by the manufacturer for monitoring of laser intensity and for stabilization purposes.

The light from both sources (210), (220) enters the fiber optic connector (224), which typically forms part of a fiber optic coupler comprising the optical connectors (224), (234) and (280) along with the optical fibers. The purpose of this fiber optic combiner is to combine the light from all four light sources to the excitation fiber (16).

The third light source (240) is preferably an ultraviolet LED, Hg spectral lamp with appropriate filter for 366 nm, UV laser or laser diode that may be utilized for NADH fluorescence excitation and for Reflectance measurements as will be explained hereinafter. This UV LED can be such as NSHU550 LED manufactured by Nichia Chemical Industries Ltd., Anan, Japan, for example. This LED emits ultraviolet radiation at a wavelength of 375 nm which is inside the excitation spectrum of the NADH. Another possible light source for the third light source (240) is NLHV500 laser diode, manufactured by the same manufacturer. This laser diode is available at several wavelengths from 390 to 410 nm. The LD with wavelength of 390 nm, since being inside the excitation band of the NADH, is also suitable for light source (240). A further example for light source (240) is a LED BP200CUV750-250 at 370 nm or L200CUV395-12D LED at 390 nm both from Ledtronics Inc. Torrance Calif.

The light from light source (240) is collimated by the suitable lens (242) and reflected by the dichroic mirror (244). The dichroic mirror (244) reflects wavelengths lower then 400 nm and allow pass through wavelengths higher then 400 nm.

Figure 13A:
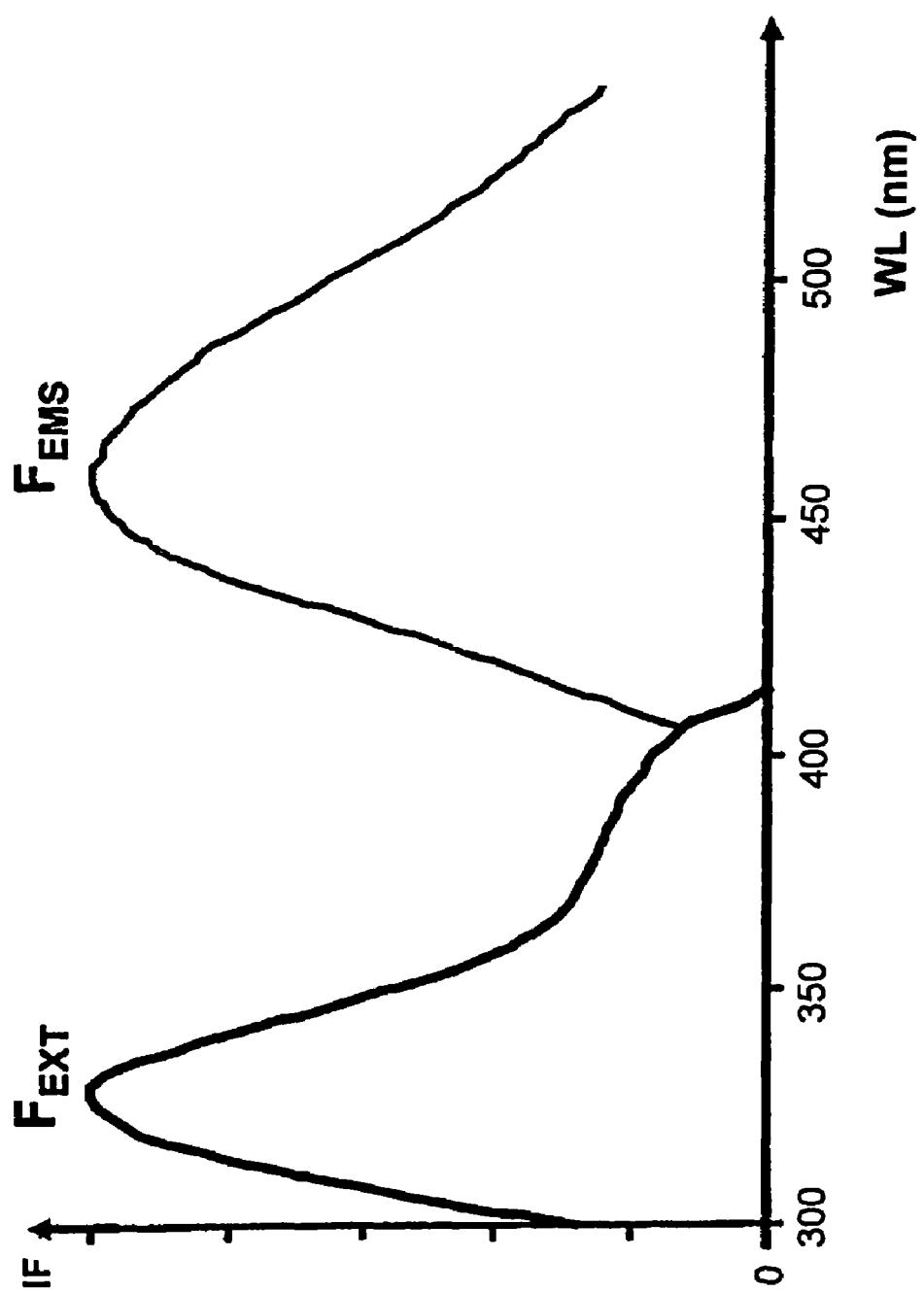
FIG. 13(a) shows the excitation fluorescence spectrum ($F_{EXT}$) and emission fluorescence spectrum ($F_{EMS}$) for NADH in terms of the corresponding fluorescence intensities (IF) as a function of wavelength (WL).
Figure 13B:
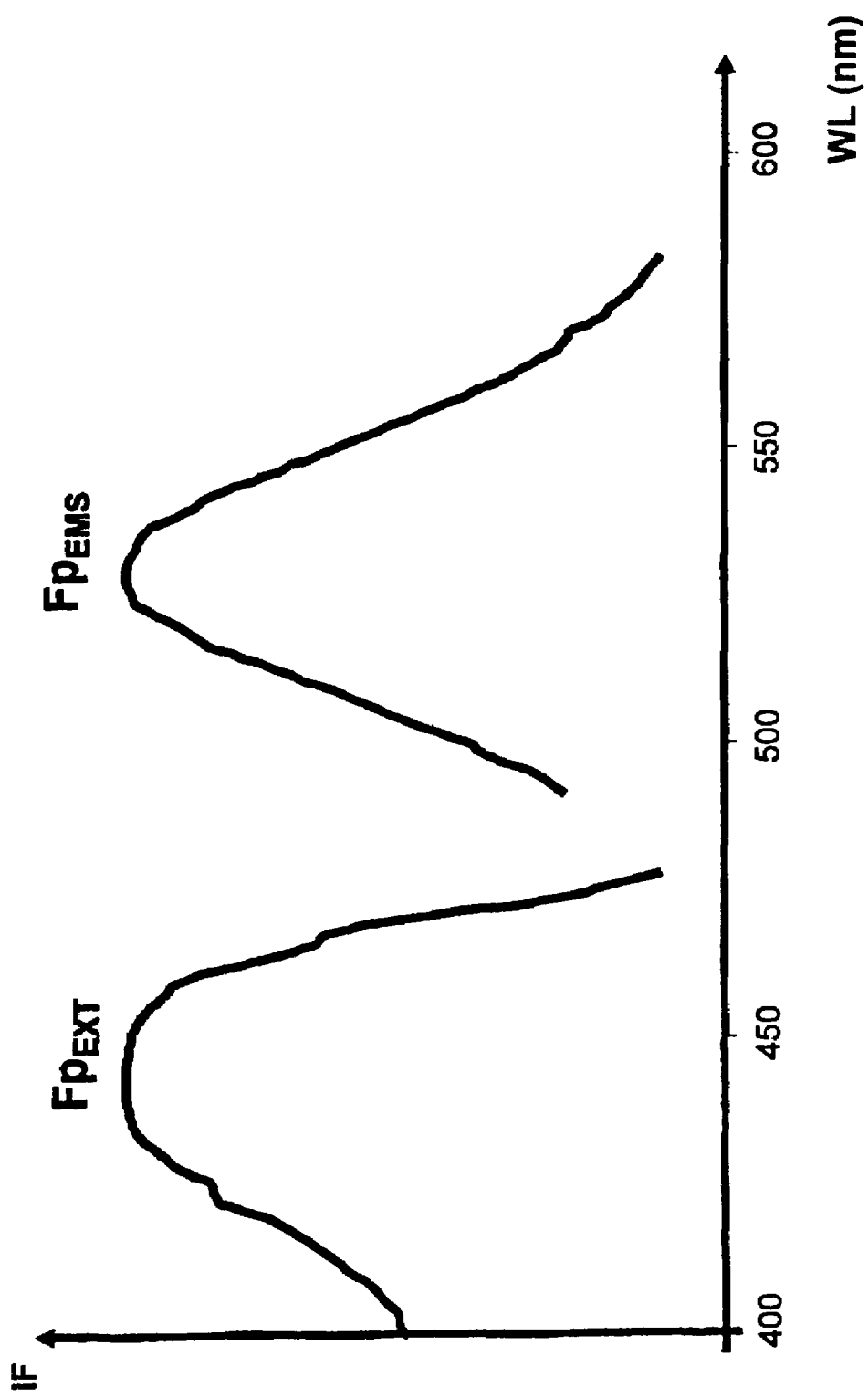
FIG. 13(b) shows the excitation fluorescence spectrum ($Fp_{EXT}$) and emission fluorescence spectrum ($Fp_{EMS}$) for Fp in terms of the corresponding fluorescence intensities (IF) as a function of wavelength (WL).

The fourth light source (230) may comprise a blue LED, blue laser or laser diode with light emission around 430 to 470 nm. This excitation source is used for measurement of two parameters. This blue light situated inside the excitation spectrum of the Fp as can be seen at FIG. 13(b). Therefore it is useful for the excitation of the Fp fluorescence. The same excitation light is used for Reflectance measurement at the excitation wavelength. This signal is used for two purposes; first, to correct the Fp fluorescence signal for hemodynamic artifact as will be described hereinafter for NADH, second, the reflectance at this wavelength along with the reflectance at 525 nm is used in order to measure the tissue blood oxygenation as will be described later.

This blue light source (230) may be, for example, a NDHB500APAE1 laser diode manufactured by Nichia Chemical Industries Ltd., Anan, Japan, which emits at a wavelength of 440 nm which is inside the excitation spectrum of the Fp.

The light from the fourth light source (230) passes through the dichroic mirror (244). Both rays of 440 nm and 375 nm pass through the beam splitter (264) and focused by lens (232) on the optical connector (234) of the fiber optic combiner consisting of optical fibers and optical connectors (224), (234) and (280). This light is coupled to the excitation fiber (16) of the fiber optic probe. On their way towards the connector (234) each of the two radiations originating from light sources (230), (240) are split, and the split components are directed towards the intensity monitoring photodiode (260) by the beam splitter (264), and is focused on the detector active area by the lens (262).

The light at the connector (280) of the fiber optic coupler thus may comprise four wavelengths namely UV light at about 370 nm, blue light at 440 nm, green light at about 525 nm and red light at about 655 nm. These different radiations are not emitted to the excitation fiber (14) simultaneously, but rather separately, but according to some appropriate time sharing arrangement that will be described later.

The light at the connector (280) is coupled to excitation connector (16) of the excitation fiber (14) of the fiber optic probe (1). The various types of the fiber optic probes will be described hereinafter. The light of the various wavelengths is guided to the tissue being monitored by the optical excitation fiber (14). At the distal end of the fiber optic probe (1) the excitation optical fiber (14) and the collection fibers (15) are in optical contact with the tissue being monitored. By "optical contact" it is meant that there is sufficient proximity, and even physical contact, between the distal end of the fibers (14), (15) and the tissue such as to enable the light from the excitation fibers (14) to penetrate the tissue, and for light emanating from the tissue to be detected by the detection fibers (15). Thus, the excitation light penetrates the tissue via the distal end of the excitation fiber (14), while some small part of the original photons or new photons originated form the tissue auto-fluorescence are reach the tissue surface and collected by the collection fibers (15). The collected light is guided back toward the device by the collection optical fibers (15). These fibers are connected to the Detection Unit (DTU) (3) by the optical connector (17).

Figure 15:
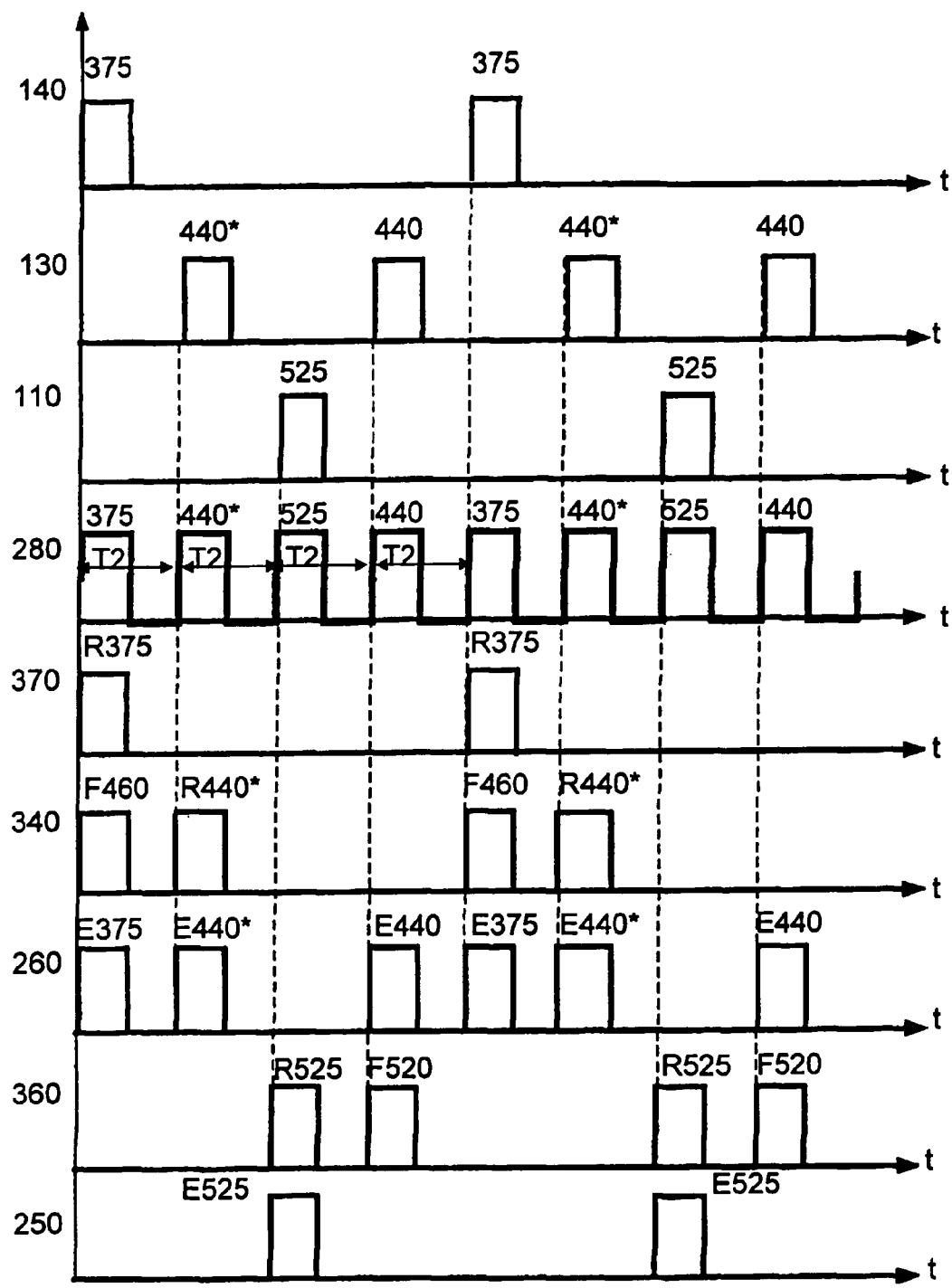
FIG. 15 shows the clock sequence of the system that enables the time sharing operation scheme. The numbers on left side indicate the corresponding light source or detector number. The numbers over the waveforms indicate the appropriate light source wavelengths or detectors wavelengths.

Referring also to FIG. 15, the light that enters the DTU (3) via the detection fibers (15) may comprise six wavelengths: the reflectance at 370 nm (R370), the NADH fluorescence at 460 nm (F460), the reflectance at 440 nm (R440), the Fp fluorescence at 520 nm (F520), the reflectance at 525 nm (R525) and the Doppler signal at 655 nm (D655). Since these six wavelengths are separated in the time domain the detection of these light signals can be accomplished by four detectors, which are synchronized with the operation timing of the appropriate light sources as will be described later.

The light from the collection fibers (15) of the fiber optic probe is channeled to the DTU (3) via the optical connector (17). The collimating lens (378) collimates the light emerging from the fibers and directs it to the first dichroic beam splitter (376). This dichroic beam splitter reflects wavelengths shorter then 400 nm towards the photodetector (370). Before reaching the photodetector (370) the light is additionally filtered to the 370 nm±10 nm by interference filter. In order to fill the active area of the detector the light is focused by the focusing lens (372). The detector (370) is particularly adapted for measuring the reflectance R370.

All wavelengths higher than 400 nm pass through the dichroic beam splitter (376) and reach the second dichroic beam splitter (346). This dichroic beam splitter reflects all wavelengths shorter then 490 nm and allows all higher wavelengths to pass therethrough. The reflectance at 440 nm (R440) and fluorescence at 460 nm (F460) pass through additional interference filter (344), which pass the wavelength of 450 nm ±15 nm, and additionally the light is focused on the photodetector (340) active area by the lens (342). The detector (340) is utilized to measure the NADH fluorescence (F460) and the reflectance (R440). These two wavelengths can be monitored by the same detector, due to time sharing, which will be described later.

The light that passes the dichroic beam splitter (346) consists of the wavelengths higher then 490 nm i.e. (D655), (R525) and (F520). The light reaches the dichroic beam splitter (386) that reflects wavelengths lower then 600 nm and transmits all wavelengths higher then 600 nm. Therefore the R525 and F520 are reflected towards the detector (360). This light pass additional filtering by the interference filter (364) that is centered at 520 nm ±20 nm. The lens (362) focuses the light on the active area of the detector.

The light that passes the dichroic filter (386) is the red light utilized for Doppler measurement—(R655). This light passes through additional interference filter (374) centered at 655 nm±10 nm and is focused on the active area of the detector (380) by the lens (382)

The signal detectors (380), (360), (340), (370) and all normalization detectors (260) and (250) are operatively connected to the Electronics Unit (EU) (4), and thus the outputs of all these detectors are channeled to the EU (4).

The EU (4) includes five functional sub units: the Analog to Digital (A/D) and Digital to Analog D/A converter (401), the LED driver electronics (430), the Laser Diode current and temperature (not shown) driver (420) and the detector's signal processing and conditioning electronics (410). The whole system works according to synchronous detection principle while the clock sequences determined by the computer PC (5), which operatively connected to the EU (4) via the D/A (401).

The apparatus (98) preferably operates according to the time sharing scheme. The light sources (240), (230) and (210) are enabled and disabled according to predefined time sequence. The red light source (220) that emits 655 nm red light for laser Doppler measurements is in ON mode during operation of the apparatus (98). This constant operation of light source (220) is due to the relative simplicity of discrimination of this red wavelength from all another wavelengths present in the device. Additionally as the result of the required bandwidth and natural fluctuations with time of the laser Doppler signal, it is more convenient to perform Doppler measurements continuously in CW mode. Therefore the light source (220) is working continuously in CW mode, while all optical system is designed to direct this red light to the appropriate Doppler detector (380), and all other parts of the optical detection system discriminate these signals.

Referring now to the FIG. 15. This time diagram illustrates the relationship between the enabling signals of the light sources and of the corresponding detectors. While each light source is in an enabling period, it generates a train of light pulses at the appropriate wavelength. This train of pulses is of exact predefined frequency and predefined ON and OFF period within each cycle, and it is different for each light source. By way of example, the apparatus (98) can operate at main sequence frequency of 4 Hz, i.e. each parameter is measured 4 times each second. This time cycle is indicated on FIG. 15 as T1, with a duration is 250 msec. Each light source has its predefined time period consisting of enable ON mode and OFF mode. This time period indicated by T2, which is of duration 62.5 msec, while the enable ON period is 50 msec and the OFF period is 12.5 msec (the Figure not in scale for simplicity). During the 50 msec of the enable ON each light source operates in pulse mode with its predefined frequency and duty cycle.

The UV light source (240) operates at 2400 Hz frequency. Each cycle duration is 417 usec, while the light is ON during 40 usec and off during 377 usec, this emerges in less then 0.1 duty cycle that ensures total duty cycle of light exposure less then 0.02, since this light source is enabled only for 50 msec in each T1 period. This very low duty cycle is important in order to low as possible the amount of UV irradiation on tissue.

The green light source (210) operates at 2800 Hz frequency. Each cycle duration is 375 usec, while the light is ON during 100 usec and OFF during 275 usec, this emerges in duty cycle of less then 0.3. There is no special requirements from this duty cycle since the total amount of irradiation that can be applied to tissue in visible region of spectrum is much higher than needed for reliable detection.

The blue light source (230) may be utilized for two different measurements as described above. When the light source (230) is utilized as excitation light source for Fp fluorescence measurements (F520) the intensity should be higher then than the same light source utilized for reflectance measurement (R440) in order to deduce the tissue oxygenation state. The light source (230) is enabled twice each cycle T1. Once for R440 measurements, indicated on the FIG. 15 as 440* and once for F520 measurements, indicated as 440 on the same Figure. When light source (230) enabled for R440 measurements it operates at 2600 Hz. The light ON period is 100 usec while the light OFF period is 285 usec. When the same light source (230) enabled for F520 measurements it operates at 2000 Hz. The light ON period is 150 usec and the light OFF period is 350 usec.

The intensity sensing photodetectors (250) and (260) also receive the pulses from the light sources according to their enabling sequence and the corresponding frequencies. The time chart on FIG. 15 shows the timing of signal appearance at the detectors (250) and (260). As shown on the diagram the detector (260) receives light from light source (240)—indicated by E375 and from the light source (230)—indicated by E440* and E440. Each excitation sequence can be determined by it's own specific frequency of light pulses appearance.

All photodetectors are operatively connected to the conditioning electronics unit (410). The signals from the detectors are amplified and converted to digital data. A suitable synchronous detection scheme is utilized in order to achieve detection of small signals in noisy environment. The electronics sub unit (410) comprises all necessary electronics hardware components and circuitry in order to perform the synchronous detection of the signals. The light sources drivers receive their appropriate conditioning signals from the A/D unit (401). This unit also provides the synchronization from the computer programmable clock for the chopping trains of all light sources and for the synchronous detectors, which analyze the detectors outputs.

Each one of the light sources enabled at different time period and operates at different frequency in order to enable discrimination of each one of the signals and it's correct detection by the appropriate detector.

Figure 16:
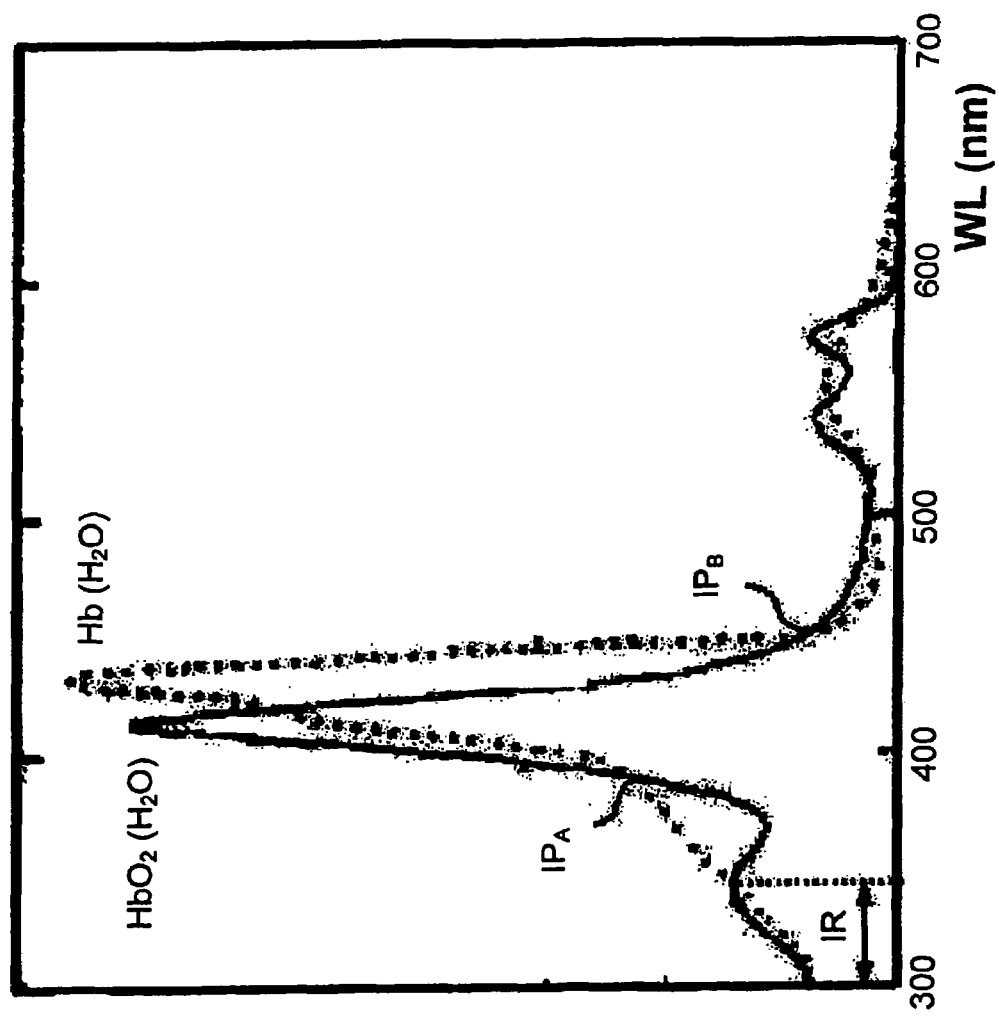
FIG. 16 illustrates light absorption of blood oxy-haemoglobin and blood deoxy-haemoglobin in terms of the Extinction parameter (E) as a function of wavelength (WL).

The oxygenation measurements designed to be performed according to the well-known method of measuring the reflectance at two different wavelengths. This method described thoroughly in scientific literature for example one of such systems (Rampil et. al. 1992) comprised a Hg lamp with a rotating filter wheel. The rotating wheel placed a correct filter into the excitation light path and additional appropriate filter into the emission light path. The system therefore measured reflectance at two wavelengths according to time sharing scheme. The wavelengths that utilized in that system where 585 nm for isosbestic point and 577 nm for non-isosbestic reflectance. The reflectance changes at 577 nm indicate changes in tissue blood oxygenation. As can be seen on FIG. 16 the oxy haemoglobin absorption at 577 nm is higher then the absorption of the deoxy haemoglobin. Therefore as the tissue blood became more oxygenated the reflectance at 577 nm became lower and vise versa. The additional measurement at isosbestic 585 nm is needed in order to compensate changes due to increase or decrease of total blood volume. Rise in total blood volume will also cause decrease of reflectance at 577 nm. Therefore measurement at 585 nm-isosbestic point is used to normalize these artifact changes.

Figure 17:
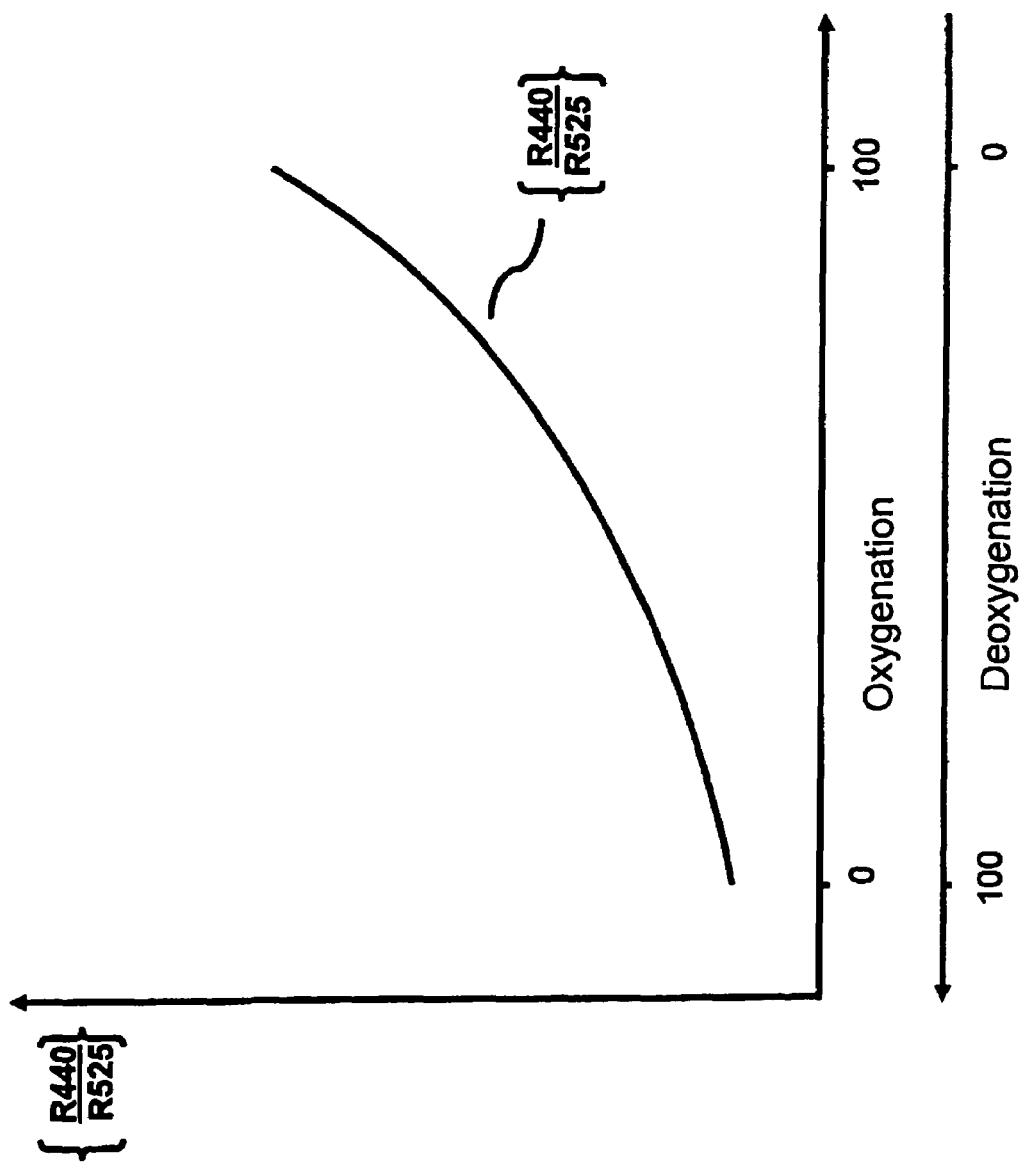
FIG. 17 illustrates schematically the ratio of reflectance at non-isosbestic wavelength to reflectance at isosbestic wavelength, as a function of oxygenation level of blood in tissue.

Similar concept is utilized in current device but with different wavelengths. The reflectance at isosbestic wavelength of 525 nm (see FIG. 16) is measured by the excitation light from light source (210) (see FIG. 14) and the photodetector (360). The reflectance at non-isosbestic wavelength of 440 nm is measured by the excitation light source (230) and the photodetector (340). The tissue blood oxygenation values can be measured after appropriate calibration according to the calibration curve at FIG. 17. The X axis of this graph is the oxygenation ratio while the Y axis of the graph is the ratio of the reflectances at the two wavelengths. The calibration should be performed against standard tissue blood oxygenation method such as pulse oximetry.

The NADH fluorescence F460 is measured by the detector (340) and the fluorescence signals are corrected by the reflectance signals R375, which measured by the detector (370). The correction algorithm is simply subscription of the normalized reflectance from the normalized fluorescence. This correction algorithm is well established in literature (Jobsis et al. Neurophysiology 3465, 735-749, 1971; Rampil et. al. 1992).

The Fp fluorescence correction algorithm is similar to that of NADH. The Fp fluorescence F520 is measured at 520 nm by the photodetector (360), the correction signal of reflectance R440 is measured by the photodetector (340).

The normalized reflectance signal is subtracted for the normalized fluorescence signal to obtain the corrected Fp signal.

The photodetectors (340) and (360) are each utilized for two different measurements. The photodetector (340) used for NADH fluorescence F460 measurements and for reflectance R440 measurements. The photodetector (360) is used for Fp fluorescence F520 measurements and for reflectance R525 measurements. The reflectance light is obviously much more intensive then the fluorescence light. Therefore these two photodetectors have two different gains. While the fluorescence measurements are performed the both photodetectors work at high gain and therefore both became very sensitive to the low intensity fluorescence light. When the reflectance measurement is performed the photodetector work with low gain therefore the relative high light intensities does not saturate the photodetectors output. The conditioning electronics (410) of the EU (4) performs the control on the photodetectors gain according to the main system clock sequence. Additionally, in order to get better S/N in Fp fluorescence measurements the Fp fluorescence excitation light source (230) works in two intensity levels. When this light source (230) is used for Fp fluorescence F520 excitation the intensity is set to HIGH. At this time period the photodetector (360) gain is high and the photodetector (340) gain is switched to OFF in order to protect it from photo-damage. When light source (230) is used for reflectance R440 measurements the intensity is set to LOW. At this time period the gain of photodetector (340) is non zero but low relatively to it's value when F460 is measured. The gain of all another detectors of the DTU (3) is set to zero. The gain of light source intensity monitoring detector (260) is also controlled according to the status of the light sources (230) and (240). The gain control of all the detectors performed by the conditioning electronics (410), which is a part of the EU (4).

The reflectance measurements R525, which is utilized by the photodetector (360) are used for assessment of two parameters, one is the tissue blood oxygenation as described above, second is total blood volume, which correlated to the total back scatter at isosbestic point at oxy-deoxy haemoglobin absorption spectrum.

The time sharing and additional chopping of the excitation light utilized in this device enable significantly reduce the total irradiation of the tissue by UV light. This is very important since the maximal permissible exposure (MPE) of human tissue to the UV light at 315-400 nm is very low (1 mw/cm$^2$) according to the ANSI Z136.1-2000 standard. This very low exposure limit is easily achieved when time sharing and additional chopping excitation scheme is used. As described above the UV light source (240) (see FIG. 14) generates light at lees then 0.02 of the time, while the intensity of the UV light at the probe distal end is less then 1 mW. Therefore the UV exposure on the tissue is about an order of magnitude lower then the MPE.

The present invention is directed to a probe for use in the multiparametric monitoring of an organ, particularly for the purpose of early diagnosis of body metabolic emergency state that may develop in many acute or chronic clinical conditions.

Referring to FIG. 18, and as will become clearer herein, a the fiber-optic probe, generally designated with the numeral (1) is adapted for transmitting light from the apparatus (98) light sources (210), (220), (230) and (240) to the monitored tissue and from the tissue back to the detection unit (3). The probe (1) comprises a fiber-optic cable (12), the proximal end of which is operatively connected to the rest of the apparatus (98), while the distal end of the probe (1) comprises a head (11), which is in secure optical contact with the tissue being monitored. The fiber optic cable (12) comprises two groups of optical fibers, each group having at least one optical fiber. The first group of fibers may be referred to as excitation fibers (14), and transmits light from the apparatus (98) to the monitored tissue. The excitation fibers group is formed from one or more fibers (14) that are bound together into an optical connector (16) at their proximal ends. The second group of optical fibers, referred to as emission fibers (15), are bound together into an optical connector (17) at their proximal ends, and collects the light that is emitted from the tissue and transmits it back to the detection unit (3) of the apparatus (98).

Various types of probes particularly adapted or designed for light irradiation and measurement of low-radiance signals from various tissues are described herein.

Cylindrical Probe for Radial Measurements in Tubular Body Vessels: Urethra, Blood Vessels and Others.

Referring to FIG. 19, a first embodiment of the probe, generally designated (101), comprises all the elements and features of the probe (1) as described herein, mutatis mutandis. In addition, the probe (101) is particularly adapted for optical measurement of low-radiance signals from the inner surface of elastic body vessels, during catheterization. This is achieved by bending the fibers, which are laid along the internal axis of the catheter, at an angle 90 degrees, or close thereto. In this manner, the distal end of the fibers, i.e., the end from which light is emitted or received, comes into direct contact with the tissue, which is typically concentric with the probe (101). This arrangement for the fiber distal ends eliminates the costly and complicated treatment which would otherwise be required to be performed to the fibers ends, to convert these into "side firing" or "side facing" fibers. Moreover, this arrangement is superior to such side facing fibers, in which the coupling efficiency between the side facing fiber and the vessel wall is relatively low. While it is normally sufficient to illuminate a tissue by emitting light into it, (as in Photo-Dynamic Therapy, for example), the poor optical contact between the side firing element and the vessel's wall results in significant losses in collecting signal that emits the vessel's wall.

In this embodiment, the fibers are arranged in one or more clusters of excitation fibers (115) and emission (116) fibers. The bending radius of the fibers is equivalent to the inner diameter of the head (112) of the probe (201), thus enabling a minimum tip diameter of typically about 3 mm ID. The clusters may be arranged in a radial symmetry, in one or more layers.

The distal tip of (113) the head (112) may be shaped as a hemisphere, for easy insertion and navigation through the vessel. The head (112) may optionally further comprise one or more tubes (117) that enable fluid transfer between the vessel interior and outside the body. Fluid transfer may be required for urine drainage, drugs injection, saline flush and other uses, depending on the vessel being monitored. Referring to FIG. 18, the tubes (117) pass from the tip (113) towards a location before the proximal end of the optical cable (12), wherein the tubes (117) emerge therefrom to form a separate manifold (18) with connection ports (19).

Probe for Measurements Upon Neonates' Skin, Gel Attachment Type.

Referring to FIG. 20(a) and FIG. 20(b), a second embodiment of the probe, generally designated (201), comprises all the elements and features of the probe (1) as described herein, mutatis mutandis. In addition, the probe (201) is particularly adapted for surface attachment to neonates' skin, using adhesive gels. Such gels (such as Ten20, by DO Weaver and Co. CO, USA, for example) are widely used with non-disposable neurodiagnostic electrodes. Thus, the head (21) is in the form of a cylindrical button, typically made from a suitable plastic, and comprises a fiber optic bundle (23). The distal end of the fiber bundle (23) is located at the center of the contact face (30) of the head (21), which also comprises two concentric open channels (25), (27). After slightly overfilling the outermost channel (25) with adhesive gel, the head (21) is pressed towards the skin and adhered thereto. The bundle (23) and plastic guide (28) which projects distally at the distal tip thereof form the contact surface (A2), which is the first to come in contact with the tissue, blocking gel that overflows from obscuring or screening the fibers. Excessive gel is forced out from the channel (25) and into the inner channel (27). The inner channel (27) acts as a "moat" that accumulates excessive gel in order to block the gel from approaching the fibers and potentially obscuring them. Thin holes (29) are drilled from the back of the head (21) into the channel (25), enabling addition of supplementary fresh gel via a syringe needle in order to reinforce the fixation when the gel dissolves.

The fiberoptic bundle (23) is sheathed within flexible tubing (22), and secured to the tip by means of epoxy mold (24). The bundle (23) may also include a deformable member such as a short non-flexible plastic or metal wire (22a), in order to enable the user to shape the bundle cable by fingers, to maintain best or lowest profile.

Probe for Measurements on Skin, Adhesive Type

Referring to FIG. 21(a) and FIG. 21(b), a third embodiment of the probe, generally designated (301), comprises all the elements and features of the probe (1) as described herein, mutatis mutandis. In addition, the probe (301) is particularly adapted for surface attachment to neonates' skin, using adhesive tape or the like. Thus, the head (31) is in the form of a mouse, and made of relatively soft (30 to 40 Shore A) RTV Silicone or silicone rubber, such that its contact surface (A3) may easily adapt to the skin contour of the patient. A fiberoptic bundle (34) is embedded into the head (31), forming an internal bend (35) of obtuse angle. Since the silicone is elastic with respect to the fibers, it can not force the required additional sharp angled bend upon the fibers. Thus, the head (31) comprises a pre-molded stiff kernel (32), made from medical grade epoxy for example, wherein to form and maintain the bend (35). The kernel (32) is then embedded into a silicone body, thereby positioning the fibers perpendicular to the surface (A3) which is to be attached to the skin (A3). The rest of the fiberoptic bundle (34) is sheathed within flexible tubing (33), wherein its distal end is cast in the head (31). The bundle (34) may also include a deformable member such as a short non-flexible plastic or metal wire (36), in order to enable the user to shape the bundle cable by fingers, to maintain best or lowest profile.

Adhesive (37) is pre-applied to the distal contact surface (A3) of the probe (301) in order to adhere the same with the skin. Such adhesive may be in the form of an adhesive tape, many examples of which are widely used upon skin for various medical applications, such as securing dressings and IV (Intravenous) tubing. In case of neonatal or fragile skin, the preferred adhesive is hydrocolloid gel (such as 9943 and 9944, by 3M, MN, USA), since this has the lowest impact upon the skin (Lund, C. et al.). In case of normal, adult skin, standard adhesives (such as acrylic or urethane adhesives) may be used.

Additional securing may be achieved by dressing over the probe (301) with external adhesive tape or hydrocolloid gel strip.

Hook Type Probe, for Fetal Distress Monitoring

Referring to FIG. 22(a) and FIG. 22(b), a fourth embodiment of the probe, generally designated (401), comprises all the elements and features of the probe (1) as described herein, mutatis mutandis. In addition, the probe (401) is particularly adapted for surface attachment of the optical fibers to the skin of a fetus, during labor. The fiberoptic bundle (44) is embedded in a heart rate electrode (41), which is commonly used for fetal monitoring after rupturing the woman's membranes. The electrode anchors must keep the fibers distal end (42) in a direct contact with the fetus skin. Thus, a dual spiral electrode (45) (such as type 15133c, by Cetro AB, Sweden, for example), of the type that was initially demonstrated in U.S. Pat. No. 3,750,650 (Ruttgers, 1973) is preferred due to its excellent anchoring characteristics. The distal end of the fiberoptic bundle (44) is fixed within the plastic tip of the electrode, forming a uniform contact surface (A4).

The fiberoptic bundle (44) is sheathed within flexible tubing (43), which is permanently secured to the tip.

Needle Type Probe, for Soft Tissue Insertion

Figure 23A:
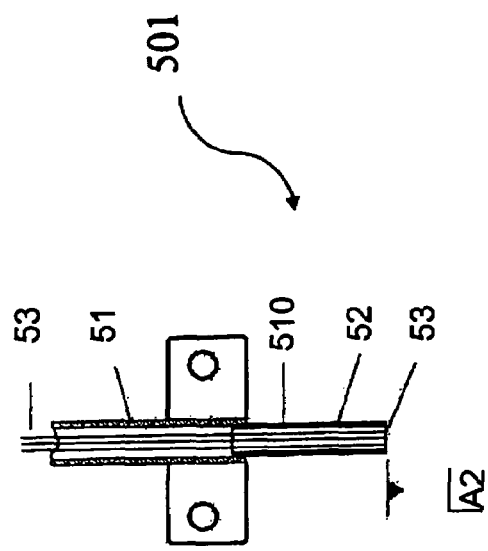
FIG. 23(a) and FIG. 23(b) illustrate, in transverse cross-sectional view and perspective view, respectively, the main components of a fifth embodiment of the probe of the present invention.
Figure 23B:
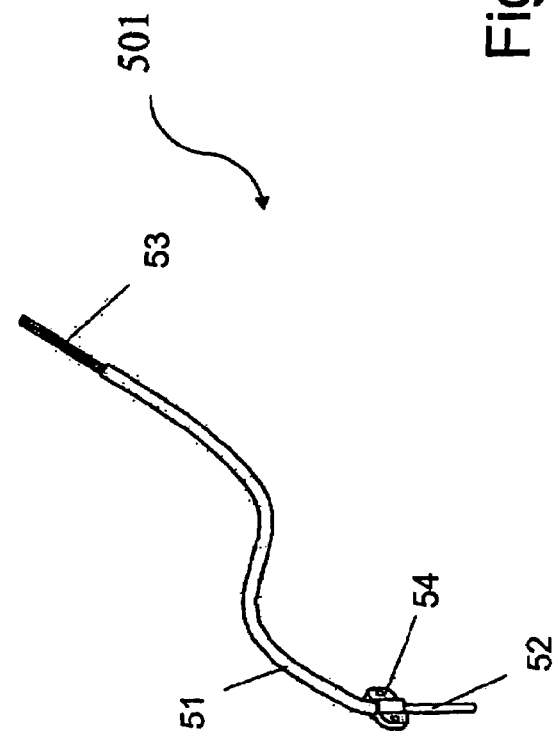

Referring to FIG. 23(a) and FIG. 23(b), a fifth embodiment of the probe, generally designated (501), comprises all the elements and features of the probe (1) as described herein, mutatis mutandis. In addition, the probe (501) is particularly adapted for insertion into soft tissues, such as muscles, internal organs and subcutaneous tissues. The head (510) is in the form of a stainless steel needle (52) embedding the optical fibers (53) that are glued into it. The fiberoptic bundle (53) is sheathed within flexible tubing (51) that overlaps the upper portion of the needle.

A small, perforated plastic plate (54), enables taping or stitching the probe (501) to an adjunct tissue to achieve additional securing.

Figure 24:
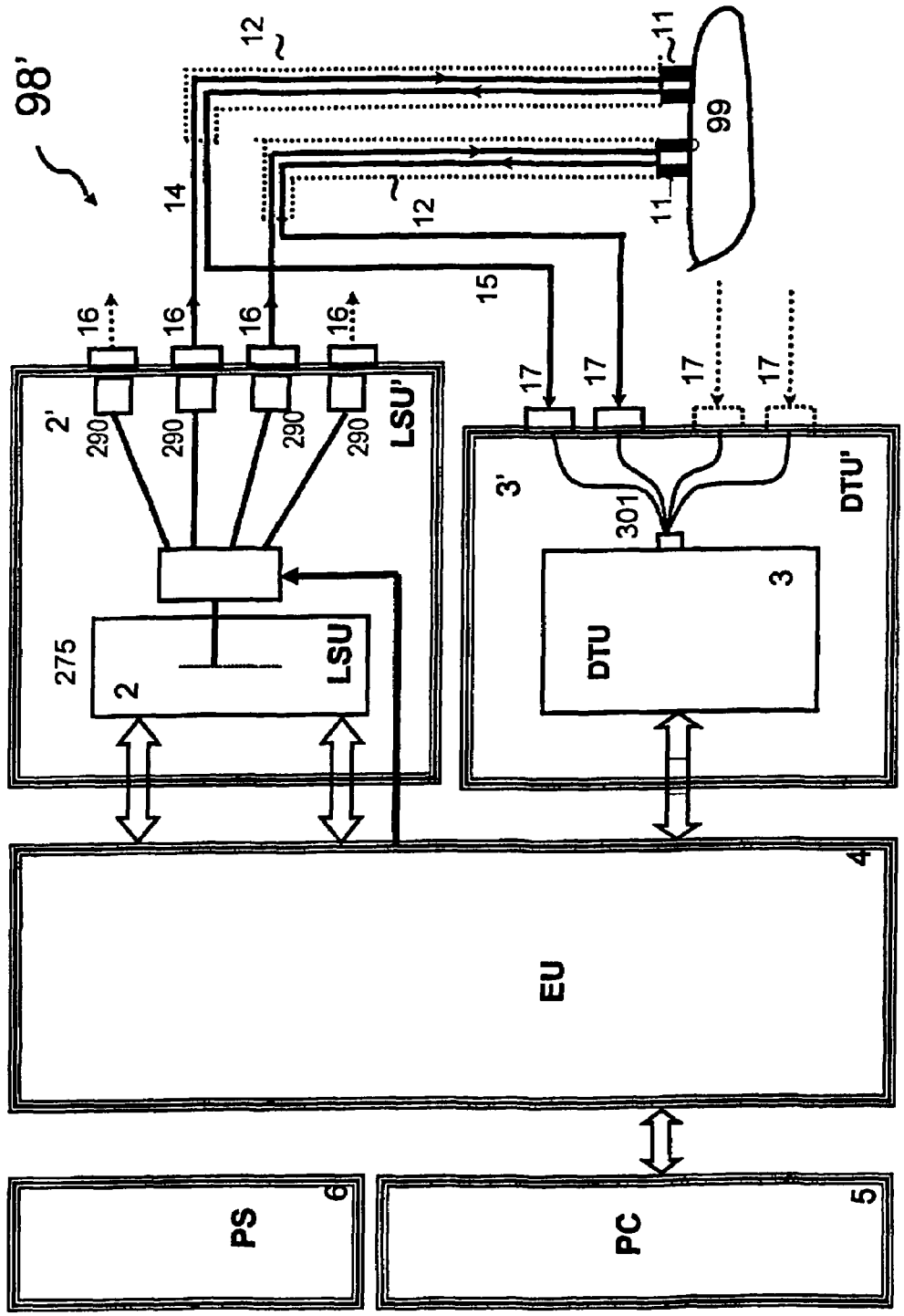
FIG. 24 illustrates schematically the main components of the second embodiment of the apparatus of the present invention

In some clinical procedures it is desirable to monitor the tissue vitality parameters in several organs of at several points of the same organ. In these situations, a multiple probe system is desirable. By way of example, a second embodiment of the present invention, consisting of a multi-probe system is shown in FIG. 24. This embodiment as illustrated, uses a plurality of probes, each probe being substantially the same as any one of those described in respect of the first embodiment, mutatis mutandis.

The time sharing feature, which provides advantages in measurements of several different parameters by single probe from same tissue, also facilitates a diversion of the irradiation light to any one of the plurality of probes and subsequent detection of the return signals therefrom, by effectively time-sharing the DTU between the probes. In other words, the multiprobe detection system essentially multiplexes the signals obtained from each of the plurality of probes, situated in different parts of the tissue or organs.

The second embodiment of the present invention, generally designated (98) comprises similar components as the first embodiment, viz LSU (2) probes (1), DTU (3), EU (4), PC (5) and PS (6) as described with respect to the first embodiment, *mutatis mutandis*, with the following exceptions. The LSU (2') of the second embodiment, as shown in FIG. 24, though substantially similar to the LSU (1) of the first embodiment (FIG. 14), further comprises the additional feature that the excitation light is passed through deflector (275) before being coupled to a plurality of the excitation fibers (14), which are each connected to a corresponding one of plurality of the adapters (290) by the optical connectors (16). This deflector (275) can be designed according to various schemes such as acousto-optic deflector, microelectromechanical system (MEMS) switch rotating mirror or prism and so on. The choice of the specific solution typically depends on availability and price performance of the system.

In the second embodiment, each collecting fiber (15) is connected to the DTU (3') by an optical connectors (17) that is essentially similar to that used in the first embodiment. The radiation received via the optical connectors (17) is coupled to a common optical coupler (301). From this optical coupler (301) the light passes through a collimating lens (378) and on to the detection equipment of the DTU (3) as described for the first embodiment *mutatis mutandis*. The electronics unit EU (4) incorporates additional outputs that control and synchronize the deflector (275) with the main clock sequence of the system.

The computer PS (5) and power supply (6) are substantially similar to those of the first embodiment. The main difference with respect to the computer PS (5) of the first embodiment lies in the system operation software, which must be adopted for multi-probe measurements. The main clock sequence form measurement of several parameters is distributed in the second embodiment between several probes. The software operates on the appropriate measured data points from each probe separately. The graphical user interface of the software shows separate data graphs for each probe or display mean value of each parameter for all probes according to the user decision.

According to the invention, then, a method is provided for diagnosing the degree of body metabolic emergency state, comprising:—

(a) choosing a non-vital organ with respect to the said metabolic emergency state;

(b) monitoring in said non-vital organ at least one tissue viability parameter including at least one of NADH and Flavoprotein (Fp) concentration; and (c) determining the degree of body metabolic emergency state based on said at least one tissue viability parameter monitored in (b).

In step (c), said determination is preferably correlated to the direction of change in the value of said at least one tissue viability parameter. Preferably, in step (c) said degree of body metabolic emergency state is correlated to the amplitude and duration of a change in said value of said at least one tissue viability parameter.

Optionally, the at least one tissue viability parameter is NADH concentration, and an increase in the value thereof is indicative of the presence of a said body metabolic emergency state.

Optionally or additionally, the at least one tissue viability parameter is Flavoprotein concentration, and a reduction in the value thereof is indicative of the presence of a said body metabolic emergency state.

Optionally or additionally, the at least one tissue viability parameter is Blood flow rate, and a reduction in the value thereof is indicative of the presence of a said body metabolic emergency state.

Optionally or additionally, the at least one tissue viability parameter is blood volume, and a reduction in the value thereof is indicative of the presence of a said body metabolic emergency state.

Optionally or additionally, the at least one tissue viability parameter is blood oxygenation level, and a reduction in the value thereof is indicative of the presence of a said body metabolic emergency state.

Typically, the non-vital organ is an organ chosen from among the skin, muscles, gastrointestinal tract and urogenital system.

Typically the body metabolic emergency state includes any one of sepsis, respiratory distress syndrome, hypoxemia, hypotension, dysoxia and cardiac arrest.

Typically, the body metabolic emergency state arises from at least one clinical situation including respiratory ICU, Neurosurgical ICU, intrapartum, neonatal ICU, cardiac surgeray operative as well as post-operative period thereof, neuro surgery operative as well as post-operative period thereof, organ transplantation operative as well as post-operative period thereof, elderly and critical ill clinical situations.

While in the foregoing description describes in detail only a few specific embodiments of the invention, it will be understood by those skilled in the art that the invention is not limited thereto and that other variations in form and details may be possible without departing from the scope and spirit of the invention herein disclosed or exceeding the scope of the claims.

REFERENCES

Bloechle, C., Strate, T., Emmermann, A., Schneider, C., Mack, D., Wolf, M., Zornig, C., Broelsch, C. E., Izbicki, J. R. (1999). Gastric tonometry accurately predicts mortality in experimental peritonitis in both laparoscopic and conventional surgery. Langenbecks Arch. Surg., 384:76-83.

Boekstegers, P., Weidenhofer, S., Kapsner, T., Werdan, K. (1994). Skeletal muscle partial pressure of oxygen in patients with sepsis. Crit. Care Med., 22:640-650.

Bratslavsky, G., Kogan, B., Levin, R. M. (2001). Urethra is more sensitive to ischemia than bladder: evidence from an in vitro rat study. J Urol., 165:2086-2090.

Cairns, C. B., Moore, F. A., Haenel, J. B., Gallea, B. L., Ortner, J. P., Rose, S. J., Moore, E. E. (1997). Evidence for early supply independent mitochondrial dysfunction in patients developing multiple organ failure after trauma. J. Trauma, 42:532-536.

Chance, B. and Williams, G. R. (1955). Respiratory enzymes in oxidative phosphorylation (III— The steady state). J. Biol. Chem., 217:409-427.

Clavijo, J. A., Sims, C., Menconi, M., Shim, I., Ochoa, C., Puyana, J. C. (2002). Multiparameter monitoring of bladder wall mucosa as a surrogate of gut tissue perfusion in hemorrhagic shock. Paper in preparation.

Dubin, A., Estenssoro, E., Murias, G., Canales, H., Sottile, P., Badie, J., Baran, M., Palizas, F., Laporte, M., Rivas Diaz, M. (2001). Effects of hemorrhage on gastrointestinal oxygenation. Intensive Care Med., 27:1931-1936.

Fiddian-Green, R. G., Baker, S. (1987). Predictive value of the stomach wall pH for complications after cardiac operations: comparison with other monitoring. Crit. Care Med. 15:153-156.

Fink, M. P. (1991). Gastrointestinal mucosal injury in experimental models of shock, trauma, and sepsis. Crit. Care Med., 19:627-641.

Hasibeder, W., Germann, R., Wolf, H. J., Haisjackl, M., Hausdorfer, H., Riedmann, B., Bonatii, J., Gruber, E., Schwarz, B., Waldenberger, P., Friesenecker, B., Furtner, B. (1996). Effects of short-term endotoxemia and dopamine on mucosal oxygenation in porcine jejunum. Am. J. Physiol., 270:G667-G675.

Hotchkiss, R. S., Karl, I. E. (1992). Reevaluation of the role of cellular hypoxia and bioenergetic failure in sepsis. JAMA, 267:1503-1510.

Ince, C., Sinaasappel, M. (1999). Microcirculatory oxygenation and shunting in sepsis and shock. Crit. Care Med., 27:1369-1377.

Guery, B. P., Mangalaboyi, J., Menager, P., Mordon, S., Vallet, B., Chopin, C. (1999). Redox status of cytochrome a,a3: a noninvasive indicator of dysoxia in regional hypoxic or ischemic hypoxia. Crit. Care Med., 27:576-582.

Jakob, M., Takala, J. (2001). Variability of splanchnic blood flow measurements in patients with sepsis—physiology, pathophysiology or measurement errors? Intensive Care Med. 27:1692-1695.

Knichwitz, G., Rotker, J., Mollhoff, T., Richter, K. D., Brussel, T. (1998). Continuous intramucosal $PCO_2$ measurement allows the early detection of intestinal malperfusion. Crit. Care Med., 26:1550-1557.

Koivisto, T., Vapalahti, M., Parviainen, I., Takala, J. (2001). Gastric tonometry after subarachnoid hemorrhage. Intensive Care Med., 27:1614-1621.

Lang, J. D., Evans, D. J, deFigueiredo, L. P., Hays, S., Mathru, M., Kramer, G. C. (1999). A novel approach to monitor tissue perfusion: bladder mucosal $PCO2$, $PO_2$, and pHi during ischemia and reperfusion. J. Crit. Care, 14:93-98.

Marik, P. E. (2001). Sublingual capnography: a clinical validation study. Chest, 120:923-927.

Marik, P. E., Varon, J. (1998). The hemodynamic derangements in sepsis: implications for treatment strategies. Chest, 114:854-860.

McKinley, B. A., Butler, B. D. (1999). Comparison of skeletal muscle $PO_2$ pH with gastric, $PCO_2$, and tonometric $PCO_2$ and pH in hemorrhagic shock. Crit. Care Med, 27:1869-1877.

McKinley, B. A., Marvin, R. G., Cocanour, C. S., Moore, F. A. (2000). Tissue hemoglobin $O_2$ saturation during resuscitation of traumatic shock monitored using near infrared spectrometry. J. Trauma, 48:637-642.

McKinley, B. A., Parmley, C. L., Butler, B. D. (1998). Skeletal muscle $PO_2$, $PCO_2$, and pH in hemorrhage, shock, and resuscitation in dogs. J. Trauma, 44:119-127.

McKinley, B. A., Ware, D. N., Marvin, R. G., Moore, F. A. (1998). Skeletal muscle pH, $PCO_2$, and $PO_2$ during resuscitation of severe hemorrhagic shock. J. Trauma, 45:633-636.

Meier-Hellmann, A., Reinhart, K. (1995). Effects of catecholamines on regional perfusion and oxygenation in critically ill patients. Acta Anaesthesiol. Scand. Suppl., 107:239-48.

Morgan, T. J., Venkatesh, B., Endre, Z. H. (1997). Continuous measurement of gut luminal $PCO_2$ in the rat: responses to transient episodes of graded aortic hypotension. Crit. Care Med., 25:1575-1578.

Nordin, A., Makisalo, H., Mildh, L., Hockerstedt, K. (1998). Gut intramucosal pH as an early indicator of effectiveness of therapy for hemorrhagic shock. Crit. Care Med. 26:1110-1117.

Pernat, A., Weil, M. H., Tang, W., Yamaguchi, H., Pernat, A. M., Sun, S., Bisera, J. (1999). Effects of hyper- and hypoventilation on gastric and sublingual $PCO_2$. J. Appl. Physiol., 87:933-937.

Povoas, H. P., Weil, M. H., Tang, W., Moran, B., Kamohara, T., Bisera, J. (2000). Comparisons between sublingual and gastric tonometry during hemorrhagic shock. Chest, 118:1127-1132.

Povoas, H. P., Weil, M. H., Tang, W., Sun, S., Kamohara, T., Bisera, J. (2001). Decreases in mesenteric blood flow associated with increases in sublingual PCO2 during hemorrhagic shock. Shock, 15:398-402.

Powell, C. C., Schultz, S. C., Burris, D. G., Drucker, W. R., Malcolm, D. S. (1995). Subcutaneous oxygen tension: a useful adjunct in assessment of perfusion status. Crit. Care Med., 23:867-873.

Puyana, J. C., Soller, B. R., Parikh, B., Heard, S. O. (2000). Directly measured tissue pH is an earlier indicator of splanchnic acidosis than tonometric parameters during hemorrhagic shock in swine. Crit. Care Med. 28:2557-2562.

Rosser, D. M., Stidwill, R. P., Millar, C. G., Singer, M. (1995). The effect of norepinephrine and dobutamine on bladder epithelial oxygen tension. Chest, 108:1368-1372.

Rozenfeld, R. A., Dishart, M. K, Tonnessen, T. I., Schlichtig, R. (1996). Methods for detecting local intestinal ischemic anaerobic metabolic acidosis by PCO2. J. Appl. Physiol., 81:1834-1842.

Ruffolo, D. C. (1998). Gastric tonometry: early warning of tissue hypoperfusion. Crit. Care Nurs. Q., 21:26-32.

Sakka, S. G., Reinhart, K., Wegscheider, K., Meier-Hellmann, A. (2001). Variability of splanchnic blood flow in patients with sepsis. Intensive Care Med., 27:1281-1287.

Sato, Y., Weil, M. H., Tang, W., Sun, S., Xie, J., Bisera, J., Hosaka, H. (1997). Esophageal $PCO_2$ as a monitor of perfusion failure during hemorrhagic shock. J. Appl. Physiol., 82:558-562.

Schlichtig, R, Heard, S. O. (1999). Sublingual $PCO_2$ measurement: the nitroglycerin of monitoring? Crit. Care Med., 27:1380-1381.

Shoemaker, W. C., Fink, S., Ray, C. W., McCartney, S. (1984). Effect of hemorrhagic shock on conjunctival and transcutaneous oxygen tensions in relation to hemodynamic and oxygen transport changes. Crit. Care Med., 12:949-952.

Sims, C., Seigne, P., Menconi, M., Monarca, J., Barlow, C., Pettit, J., Puyana, J. C. (2001). Skeletal muscle acidosis correlates with the severity of blood volume loss during shock and resuscitation. J. Trauma, 51:1137-1146.

Singer, M., Millar, C., Stidwill, R., Unwin, R. (1996). Bladder epithelial oxygen tension—a new means of monitoring regional perfusion? Preliminary study in a model of exsanguination/fluid repletion. Intensive Care Med., 22:324-328.

Singer, M., Rosser, D., Stidwill, R. (1995). Bladder epithelial oxygen tension as a marker of organ perfusion. Acta Anaesthesiol. Scand. Suppl., 107:77-80.

Soller, B. R., Heard, S. O., Cingo, N. A., His, C., Favreau, J., Khan, T., Ross, R. R., Puyana, J. C. (2001). Application of fiberoptic sensors for the study of hepatic dysoxia in swine hemorrhagic shock. Crit. Care Med., 29:1438-1444.

Third European Consensus Conference in Intensive Care Medicine (1996). Tissue hypoxia: how to detect, how to correct, how to prevent? Am. J. Crit. Care Med., 154:1573-1578.

Vallet, B., Lund, N., Curtis, S. E., Kelly, D., Cain, S. M. (1994). Gut and muscle tissue PO2 in endotoxemic dogs during shock and resuscitation. J. Appl. Physiol., 76:793-800.

Venkatesh B, Clutton Brock T H, Hendry S P. (1994). A multiparameter sensor for continuous intra-arterial blood gas monitoring: a prospective evaluation. Crit. Care Med., 22:588-594.

Venkatesh, B., Morgan, T. J., Lipman, J. (2000). Subcutaneous oxygen tensions provide similar information to ileal luminal $CO_2$ tensions in an animal model of haemorrhagic shock. Intensive Care Med., 26:592-600.

Walley, K. R., Friesen, B. P., Humer, M. F., Phang, P. T. (1998). Small bowel tonometry is more accurate than gastric tonometry in detecting gut ischemia. J. Appl. Physiol., 85:1770-1777.

Weil, M. H. (2000). Tissue $PCO_2$ as universal marker of tissue hypoxia. Minerva Anestesiol. 66:343-347. Minerva Anestesiol. 66:343-347.

Weil, M. H., Nakagawa, Y., Tang, W., Sato, Y., Ercoli, F., Finegan, R., Grayman, G., Bisera, J. (1999). Sublingual capnometry: a new noninvasive measurement for diagnosis and quantitation of severity of circulatory shock. Crit. Care Med., 27:1225-1229.

Lund, C., Kuller, J., Lane, A., Lott, J. W., Raines, D. A. (1999). Neonatal skin care: the scientific basis for practice. Neonatal Netw., 18(4):15-27.

The invention claimed is:

1. Apparatus which monitors in a non-vital organ at least one tissue viability parameter of a body tissue, the apparatus comprising:
 a) a light source for illuminating a first part of said tissue with at least one illuminating radiation via at least one illumination location;
 b) a light collector for receiving radiation from a second part of said tissue, the same as or different from the first part, as a result of an interaction between said illuminating radiation and said tissue, the light collector comprising a filter which preferentially admits a range of wavelengths comprising a portion of, but not all of, the fluorescent emission spectrum of NADH or Fp;
 c) a correlator adapted for correlating at least a part of said received radiation with said at least one tissue viability parameter; and
 d) an analyzer adapted for generating an indication of a degree of body metabolic emergency state based on said correlating;
wherein the at least one tissue viability parameters comprise at least one of NADH or flavoprotein (Fp) concentration, and the received radiation comprises at least one of NADH and Fp fluorescence emitted by said tissue.

2. Apparatus as claimed in claim 1, wherein the at least one tissue viability parameter comprises an NADH concentration, and the received radiation comprises NADH fluorescence emitted by said tissue.

3. Apparatus as claimed in claim 1, wherein the at least one tissue viability parameter comprises an Fp concentration, and the received radiation comprises Fp fluorescence emitted by said tissue.

4. Apparatus as claimed in claim 1, wherein the at least one tissue vitality parameter also comprises at least one of blood flow rate, blood volume, and oxy-deoxy state.

5. Apparatus as claimed in claim 1, wherein said illuminating radiation comprises a plurality of wavelengths corresponding to the number of different tissue viability parameters being monitored.

6. Apparatus as claimed in claim 1, wherein said at least one tissue viability parameter comprises NADH concentration, arid said illuminating radiation comprises radiation having a wavelength in the range of between about 315 nm to about 400 nm, for monitoring NADH concentration.

7. Apparatus as claimed in claim 6, wherein said light source comprises a suitable LED for providing an illuminating radiation of said wavelength.

8. Apparatus of claim 7, wherein the wavelength is selected from the group consisting of about 366 nm, about 375 nm, about 380 nm, and about 390 nm.

9. Apparatus of claim 6, wherein the wavelength is selected from the group consisting of about 366 nm, about 375 nm, about 380 nm, and about 390 nm.

10. Apparatus as claimed in claim 1, wherein said at least one tissue viability parameter comprises flavoprotein concentration and said illuminating radiation comprises radiation having a wavelength between about 430 nm and about 470 nm for monitoring flavoprotein concentration.

11. Apparatus as claimed in claim 1, wherein said at least one tissue viability parameter also comprises blood oxygenation, and said illuminating radiation comprises radiation peaked around an isosbestic wavelength, and radiation having a non-isosbestic wavelength, for monitoring blood oxygenation.

12. Apparatus as claimed in claim 11, wherein said radiation peaked around an isosbestic wavelength is green.

13. Apparatus as claimed in claim 10, wherein the isosbestic wavelength is about 525 nm.

14. Apparatus as claimed in claim 9, wherein the radiation of non-isosbestic wavelength has wavelength between about 430 nm and 470 nm.

15. Apparatus as claimed in claim 1, wherein said at least one tissue viability parameter also comprises blood flow rate, and said illuminating radiation comprises radiation having a wavelength between about 550 nm and 800 nm, for monitoring blood flow.

16. Apparatus as claimed in claim 15, wherein said illuminating radiation is of a wavelength and a coherence suitable for laser Doppler flowmetry, and said correlator is adapted to correlate said received radiation to said blood flow rate tissue viability parameter by applying a laser Doppler flowmetry technique to said received radiation.

17. Apparatus of claim 15, wherein the wavelength is about 655 nm or about 785 nm.

18. Apparatus as claimed in claim 1, wherein said illumination location is provided by at least one excitation optical fiber having a free end capable of being brought into registry with said first part of said tissue.

19. Apparatus as claimed in claim 18, wherein said light collector comprises at least one suitable receiving optical fiber having a free end capable of being brought into registry with said second part of said tissue.

20. Apparatus as claimed in claim 19, wherein said at least one excitation optical fiber and said at least one receiving optical fiber are housed in a suitable probe head.

21. Apparatus as claimed in claim 20, wherein said at least one excitation fiber comprises a suitable first connector at an end thereof opposed to said free end thereof, said first connector capable of selectively coupling and decoupling said excitation fiber from the rest of the said apparatus.

22. Apparatus as claimed in claim 21, wherein said at least one collection fiber comprises a suitable second connector at an end thereof opposed to said free end thereof, said second connector capable of selectively coupling and decoupling said collection fiber from the rest of the said apparatus.

23. Apparatus as claimed in claim 22, wherein said probe is disposable.

24. Apparatus as claimed in claim 22, wherein said probe is sterilizable.

25. Apparatus as claimed in claim 20, wherein said probe bead is adapted for optical measurement in organs comprising tubular vessels.

26. Apparatus as claimed in claim 25, wherein said probe head is adapted for optical measurement in at least one of the esophagus, urethra, blood vessels, stomach and bladder.

27. Apparatus as claimed in claim 26, wherein said probe is incorporated in a suitable urethral catheter including a Foley catheter.

28. Apparatus as claimed in claim 20, wherein said probe bead is adapted for optical measurement on organs comprising skin.

29. Apparatus as claimed in claim 28, wherein said probe bead is adapted to be attached to the skin via a suitable gel.

30. Apparatus as claimed in claim 28, wherein said probe head is adapted to be attached to the skin via a suitable adhesive.

31. Apparatus as claimed in claim 20, wherein said probe head is adapted for fetal distress monitoring.

32. Apparatus as claimed in claim 20, wherein said probe head is adapted for soft tissue insertion.

33. Apparatus as claimed in claim 1, further comprising a first detector for detecting said received radiation received by said light collector.

34. Apparatus as claimed in claim 1, wherein said at least one tissue viability parameter also comprises blood volume, and said radiation received by said light collector comprises a reflectance from said tissue in response to illumination thereof by said illuminating radiation, the said blood volume being provided by the intensity of said reflectance.

35. Apparatus as claimed in claim 34, wherein said illuminating radiation is peaked around an isosbestic wavelength.

36. Apparatus as claimed in claim 35, wherein said radiation received by said light collector comprises two separate reflectances from said tissue in response to illumination thereof by two different illuminating radiations, the blood volume being provided by the intensity of each said reflectance, wherein each said illuminating radiation is peaked around a different isosbestic wavelength.

37. Apparatus as claimed in claim 1, wherein said first part and said second part are at the same location of said tissue.

38. Apparatus as claimed in claim 1, wherein said first part of said tissue is different from said second part of said tissue.

39. Apparatus as claimed in claim 1, wherein said body metabolic emergency state is sepsis.

40. A system for selectively monitoring in a plurality of organs at least one tissue viability parameter including at least one of NADH and Flavoprotein (Fp) concentration corresponding to each said organ being monitored, for the early diagnosis of body metabolic emergency state, said system comprising a plurality of monitoring probes, each said probe comprising an apparatus as claimed in claim 1.

41. A system as claimed in claim 40, wherein said plurality of organs are different organs within the same organism.

42. A system as claimed in claim 40, wherein said plurality of organs are different organs within different organisms.

43. A system as claimed in claim 40, wherein said plurality of organs include donor organs.

44. A system for selectively monitoring in a plurality of locations in the same organ at least one tissue viability parameter including at least one of NADH and Flavoprotein (Fp) concentration corresponding to each said location of the organ being monitored, for the early diagnosis of body metabolic emergency state, said system comprising a plurality of monitoring probes, each said probe comprising an apparatus as claimed in claim 1.

45. Apparatus as claimed in claim 1, wherein the correlator uses a measurement of reflectance of the illuminating radiation from the tissue to calibrate the intensity of the fluorescence.

46. Apparatus according to claim 1, wherein the filter preferentially admits substantially only a single contiguous band of optical wavelengths.

47. A method for diagnosing a degree of body metabolic emergency state, comprising:
  a) choosing a non-vital organ to monitor;
  (b) exciting at least one of NADH and Flavoprotein (Fp) fluorescence in tissue of said non-vital organ by radiation in the fluorescent excitation spectrum of at least one of NADH and Fp;
  (c) monitoring in said non-vital organ at least one tissue viability parameter including at least one of NADH and Flavoprotein (Fp) concentration, by measuring radiation emitted from said excited tissue that passes through a filter that preferentially admits wavelengths in a range comprising a portion of, but not all of, the fluorescent emission spectrum of NADH or Fp;
  (d) determining the degree of body metabolic emergency state based on said at least one tissue viability parameter monitored in (c); and
  (e) indicating to a user the degree of body metabolic emergency state, at least when the degree is greater than a threshold.

48. A method as claimed in claim 47, wherein determining the degree of body metabolic emergency state is correlated to the direction of change in the value of said at least one tissue viability parameter.

49. A method as claimed in claim 47, wherein said degree of body metabolic emergency state is correlated to the amplitude and duration of a change in said value of said at least one tissue viability parameter.

50. A method as claimed in claim 47, wherein the at least one tissue vitality parameter includes NADH concentration, and an increase in the value thereof is indicative of the presence of a said body metabolic emergency state.

51. A method as claimed in claim 47, wherein said at least one tissue viability parameter includes Flavoprotein concentration, and a reduction in the value thereof is indicative of the presence of a said body metabolic emergency state.

52. A method as claimed in claim 47, wherein said at least one tissue viability parameter comprises blood flow rate, and a reduction in the value thereof is indicative of the presence of a said body metabolic emergency state.

53. A method as claimed in claim 47, wherein said at least one tissue viability parameter also comprises blood volume, and a reduction in the value thereof is indicative of the presence of a said body metabolic emergency state.

54. A method as claimed in claim 47, wherein said at least one tissue viability parameter also comprises blood oxygenation level, and a reduction in the value thereof is indicative of the presence of a said degree of body metabolic emergency state.

55. A method as claimed in claims 47, wherein said non-vital organ is chosen from among the skin, muscles, gastrointestinal tract and urogenital system.

56. A method as claimed in claims 47, wherein said body metabolic emergency state includes any one of sepsis, respiratory distress syndrome, hypoxemia, hypotension, dysoxia and cardiac arrest.

57. A method as claimed in claims 47, wherein said body metabolic emergency state arises from at least one clinical situation including those that develop in a respiratory ICU, Neurosurgical ICU, delivery room both for a mother and her neonate, neonatal ICU, cardiac surgery operative room as well as post-operative period thereof, neuro surgery operative as well as post-operative period thereof, organ transplantation operative as well as post-operative period thereof, elderly and critical ill clinical situations.

58. A method as claimed in claim 47, wherein monitoring comprises calibrating said emitted radiation by measuring reflection of radiation in the excitation spectrum from said tissue.

59. A method as claimed in claim 40, wherein determining a given degree of body emergency metabolic state comprises determining whether the at least one tissue viability parameter has changed by an amplitude exceeding a threshold for a duration exceeding a threshold.

60. A method as claimed in claim 59, wherein monitoring comprises monitoring a hospitalized patient in a clinical situation sufficiently continuously so as to be unlikely to miss a change in the at least one tissue viability parameter exceeding said thresholds in amplitude and duration, during the time the clinical situation persists.

* * * * *